(12) United States Patent
Ding et al.

(10) Patent No.: US 8,785,634 B2
(45) Date of Patent: Jul. 22, 2014

(54) SPIROPIPERIDINE PROLYLCARBOXYPEPTIDASE INHIBITORS

(75) Inventors: Fa-Xiang Ding, Staten Island, NY (US); JinLong Jiang, Scotch Plains, NJ (US); Dong-Ming Shen, Edison, NJ (US); Hong Shen, West Windsor, NJ (US); Zhi-Cai Shi, Monmouth Junction, NJ (US)

(73) Assignee: Merck Sharp & Dohme Corp, Rahway, NJ (US)

( * ) Notice: Subject to any disclaimer, the term of this patent is extended or adjusted under 35 U.S.C. 154(b) by 0 days.

(21) Appl. No.: 13/638,976

(22) PCT Filed: Apr. 21, 2011

(86) PCT No.: PCT/US2011/033407
§ 371 (c)(1),
(2), (4) Date: Oct. 2, 2012

(87) PCT Pub. No.: WO2011/137024
PCT Pub. Date: Nov. 3, 2011

(65) Prior Publication Data
US 2013/0023515 A1    Jan. 24, 2013

Related U.S. Application Data

(60) Provisional application No. 61/327,989, filed on Apr. 26, 2010.

(51) Int. Cl.
*C07D 401/00* (2006.01)

(52) U.S. Cl.
USPC .......................................................... 546/17

(58) Field of Classification Search
USPC .......................................................... 546/17
See application file for complete search history.

(56) References Cited

U.S. PATENT DOCUMENTS

| | | | |
|---|---|---|---|
| 3,959,475 A * | 5/1976 | Bauer et al. | 514/278 |
| 3,980,787 A | 9/1976 | Klioze et al. | |
| 4,024,263 A * | 5/1977 | Klioze et al. | 514/278 |
| 4,031,224 A * | 6/1977 | Martin et al. | 514/278 |
| 7,332,501 B2 * | 2/2008 | Bissantz et al. | 514/278 |
| 2008/0108080 A1 | 5/2008 | Chissoe | |

FOREIGN PATENT DOCUMENTS

| | | |
|---|---|---|
| EP | 1 498 424 A2 | 1/2005 |
| EP | 1 498 424 A3 | 5/2005 |
| WO | 2004/072265 A2 | 8/2004 |
| WO | 2004/072265 A3 | 8/2004 |
| WO | 2005/115446 A2 | 12/2005 |
| WO | 2005/115446 A3 | 12/2005 |
| WO | WO2007041052 A2 | 4/2007 |
| WO | WO 2007047496 * | 4/2007 |
| WO | 2007/140896 A1 | 12/2007 |
| WO | 2011/137012 A1 | 11/2011 |
| WO | 2011/143057 A1 | 11/2011 |
| WO | 2011/146300 A1 | 11/2011 |
| WO | 2011/146354 A1 | 11/2011 |
| WO | 2011/156220 A1 | 12/2011 |
| WO | 2011/156246 A1 | 12/2011 |

OTHER PUBLICATIONS

Klioze et al. Journal of Medicinal Chemistry (1978), 21(4), 400-3.*
Bray, G. A. et al., "Sibutramine Produces Dose-Related Weight Loss", Obesity Research, 1999, p. 189-, vol. 7. No. 2.
Davidson, M. H. et al., "Weight Control and Risk Factor Reduction in Obee Subjects Treated for 2 Years With Orlistat", JAMA, 1999, p. 235-, vol. 281, No. 3.
Douglas, A. et al., Plasma Phentermine Levels, Weight Loss and Side-Effects, International Journal of Obesity, 1983, p. 591-595, vol. 7.
Encinosa, W. E. et al., "Recent Improvements in Bariatric Surgery Outcomes", Medical Care, 2009, p. 531-, vol. 47, No. 5.
Flum, D. R. et al., "Early Mortality Among Medicare Beneficiaries Undergoing Bariatric Surgical Procedures", JAMA, 2005, p. 1903-, vol. 294, No. 15.
Bauer, V. J. et al., Synthesis of Spiro [isobenzofuran-1 (3H), 4-piperidines] as Potential Central Nervous System Agents, Journal of Medicinal Chemistry, 1976, p. 1315-1324, vol. 19, No. 11.

* cited by examiner

*Primary Examiner* — Nizal Chandrakumar
(74) *Attorney, Agent, or Firm* — Baerbel R. Brown; Catherine D. Fitch

(57) ABSTRACT

Compounds of structural formula (I) are inhibitors of prolylcarboxypeptidase (PrCP). The compounds of the present invention are useful for the prevention and treatment of conditions related to enzymatic activity of PrCP such as abnormal metabolism, including obesity; diabetes; metabolic syndrome; obesity related disorders; and diabetes related disorders.

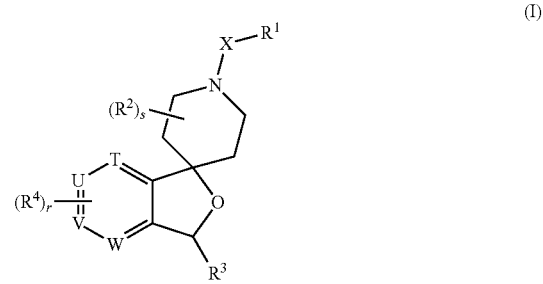

15 Claims, No Drawings

SPIROPIPERIDINE PROLYLCARBOXYPEPTIDASE INHIBITORS

CROSS-REFERENCE TO RELATED APPLICATIONS

This application is a U.S. National Phase application under 35 U.S.C. §371 of PCT Application No. PCT/US2011/033407, filed 21 Apr. 2011, which claims priority from and the benefit of U.S. Provisional Application No. 61/327,989, filed Apr. 26, 2010.

FIELD OF THE INVENTION

The present invention relates to compounds which are inhibitors of the prolylcarboxy-peptidase (PrCP) enzyme and the use of such compounds to control, prevent and/or treat conditions or diseases mediated by prolylcarboxypeptidase activity. The compounds of the present invention are useful for the control, prevention and treatment of conditions and diseases related to abnormal metabolism, including obesity; diabetes; metabolic syndrome, obesity related disorders and diabetes related disorders.

BACKGROUND OF THE INVENTION

Obesity, which can be defined as a body weight more than 20% above the ideal body weight, is a major health concern in Western societies. It is estimated that about 97 million adults in the United States are overweight or obese. Obesity is the result of a positive energy balance, as a consequence of increased ratio of caloric intake to energy expenditure. Epidemiological studies have shown that increasing degrees of overweight and obesity are important predictors of decreased life expectancy. Obesity causes or exacerbates many health problems, both independently and in association with other diseases. The medical problems associated with obesity, which can be serious and life-threatening, include hypertension; type 2 diabetes mellitus; elevated plasma insulin concentrations; insulin resistance; dyslipidemias; hyperlipidemia; endometrial, breast, prostate and colon cancers; osteoarthritis; respiratory complications, such as obstructive sleep apnea; cholelithiasis; gallstones; arteriosclerosis; heart disease; abnormal heart rhythms; and heart arrythmias (Kopelman, P. G., Nature 404, 635-643 (2000)). Obesity is further associated with premature death and with a significant increase in mortality and morbidity from stroke, myocardial infarction, congestive heart failure, coronary heart disease, and sudden death.

Pro-opiomelanocortin (POMC) derived peptides are known to affect food intake. Several lines of evidence support the notion that the G-protein coupled receptors (GPCRs) of the melanocortin receptor (MC-R) family, several of which are expressed in the brain, are the targets of POMC derived peptides involved in the control of food intake and metabolism. A specific single MC-R that may be targeted for the control of obesity has not yet been identified, although evidence has been presented that MC-4R signalling is important in mediating feed behavior (S. Q. Giraudo et al., "Feeding effects of hypothalamic injection of melanocortin-4 receptor ligands," Brain Research, 80: 302-306 (1998)).

The prohormone pro-opiomelanocortin (POMC) plays a critical role in the regulations of energy metabolism, and is processed by proteases to produce several peptide hormones, including alpha-melanocyte-stimulating hormone (α-MSH or α-MSH$_{1-13}$). α-MSH is a major regulator of feeding and body weight homeostasis. Studies have shown that α-MSH$_{1-13}$ is a critical anorexigenic neuromodulator found in the hypothalamus, which inhibits food intake by binding target neurons expressing melanocortin receptors 3 and 4 (MC3R and MC4R) (see Vaisse et al., J. Clin. Invest., 106, 253-62 (2000); and Williams et al., Am. J. Physiol. Regul. Integr. Comp. Physiol., 289:R2-R3 (2005). MC-3R is expressed in the brain, gut, and placenta and may be involved in the control of food intake and thermogenesis. MC-4R is uniquely expressed in the brain, and its inactivation was shown to cause obesity (A. Kask, et al., "Selective antagonist for the melanocortin-4 receptor (HS014) increases food intake in free-feeding rats," Biochem. Biophys. Res. Commun., 245: 90-93 (1998)).

The enzyme prolylcarboxypeptidase (PRCP, Lysosomal Pro-X carboxypeptidase, angiotensinase C) is a serine protease that cleaves small, biologically active peptides at carboxyl termini linked to a penultimate proline group. α-MSH is a substrate of PRCP due to its C-terminal amino acid sequence, Pro-Val. Recent studies have shown that PRCP initiates the degradation of α-MSH$_{1-13}$ into inactive extracellular α-MSH$_{1-12}$, which is effective in reducing food intake and in regulating neuronal functions via melanocortin receptors. In overnight fasted animals, 2.5 ug of α-MSH$_{1-13}$ induced a 40% reduction in food intake relative to control animals, however, overnight fasted animals treated with 2.5 ug of α-MSH$_{1-12}$ did not significantly affect food intake compared to the controls. (Wallingford et al., J. Clinical Investigation, Vol. 119, No. 8, August 2009).

Further it has been shown, that PRCP inhibition by small molecule protease inhibitors administered peripherally or centrally decreased food intake in wild type and genetically obese animals. Specifically, both the intracerebroventricular to rats and systemic administration to obese, leptin deficient mice of t-butyl carbamate-prolyl prolinal (BPP), which is an inhibitor of PRCP, resulted in a suppression of overnight food intake (Wallingford et al., J. Clinical Investigation, Vol. 119, No. 8, August 2009).

A recent study also showed that PrCP null mice had elevated hypothalamic levels of α-MSH$_{1-13}$ and were leaner compared with wild-type controls when fed regular chow, and were also resistant to high fat diet induced obesity. Specifically, on a high fat diet, PrCP gt/gt mice also showed a significant reduction in body weight and a reduction in food intake (Wallingford et al., J. Clinical Investigation, Vol. 119, No. 8, August 2009).

These studies suggest that PRCP inhibitors influence food intake and weight maintenance via melanocortin receptors and the control of active α-MSH$_{1-13}$ levels, and that targeting PRCP activity with central or peripheral administration of inhibitors can reduce food intake.

WO 2005/115446 discloses the role of prolylcarboxypeptidase inhibitors in weight control, control of body fat and food intake; and specific prolylcarboxypeptidase inhibitors, including t-butyl carbamate (BOC)-prolyl prolinal (BPP), N-benzyloxycarbonyl-prolyl-prolinal, diisopropyl fluorophosphates, PMSF, antipain, leupeptin, corn trypsin and mercuric chloride, useful to treat obesity and obesity related disorders. WO 2005/115446 also discloses the association of PRCP with hypertension, dyslipidemia, diabetes, stroke, gallbladder disease, cardiovascular disease, osteoarthritis, rheumatoid arthritis, hypercholesterolemia, angina, atherosclerosis, sleep apnea, respiratory problems, and cancer.

US 2008-0108080 discloses the utility of small molecule compounds with activity against the gene products encoded by PRCP for use in treating obesity.

WO 2007/140896 discloses the association of human PRCP with cardiovascular diseases, hematological diseases, neurological diseases and cancer based upon tissue distribution of PrCP.

The prolylcarboxypeptidase (PRCP) enzyme is disclosed in EP 1498424 and WO 2004/072265.

The present invention is concerned with novel spiroether compounds as inhibitors of prolylcarboxypeptidase which are useful in the treatment and/or prevention of various conditions and diseases mediated by prolylcarboxypeptidase activity including, but not limited to, abnormal metabolism, obesity, diabetes, metabolic syndrome, obesity and diabetes related disorders, such as hypertension, dyslipidemia, stroke, gallbladder disease, cardiovascular disease, osteoarthritis, rheumatoid arthritis, hypercholesterolemia, stable angina, unstable angina, artherosclerosis, sleep apnea, respiratory problems, cancer, stroke, hematological diseases and neurological diseases.

Weight loss drugs that are currently used to treat obesity have limited efficacy and significant side effects. Studies of the weight loss medications orlistat (Davidson, M. H. et al. (1999) JAMA 281:235-42), dexfenfluramine (Guy Grand, B. et al. (1989) Lancet 2:1142-5), sibutramine (Bray, G. A. et al. (1999) Obes. Res. &: 189-98) and phentermine (Douglas, A. et al. (1983) Int. J. Obes. 7:591-5) have demonstrated a limited weight loss of about 5%-10% of body weight for drug compared to placebo. The side effects of these drugs and anti-obesity agents further limit their use, Dexfenfluramine was withdrawn from the market because of suspected heart valvulopathy; orlistat is limited by gastrointestinal side effects; the use of topiramate is limited by central nervous system effects; and the use of sibutramine is limited by its cardiovascular side effects which have led to reports of deaths and its withdrawal from the market in Italy. Obese patients generally respond well to surgical interventions that modify the gastrointestinal tract and limit food intake. However, one out of fifty bariatric surgery patients dies within the first 30 days post surgery, and 4.6% of bariatric surgery patients die within the first year (*J. Amer. Med. Assoc.,* 2005, 294, 1903). Another study indicated that 33% of patients that undergo bariatric surgery have complications that require re-hospitalization within the first 6 months post operation (*Medical Care,* 2009, 47, 531).

There is a need for a weight loss treatment with enhanced efficacy, increased safety, and fewer undesirable side effects. The instant invention addresses this problem by providing prolylcarboxypeptidase inhibitors useful in the treatment and prevention of obesity, diabetes, and related disorders.

SUMMARY OF THE INVENTION

The present invention relates to spiroether compounds of structural formula I:

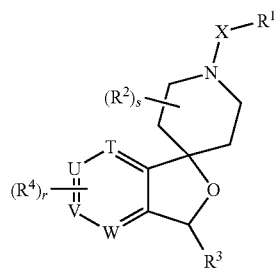

Compounds of formula I are inhibitors of prolylcarboxypeptidase (PrCP) and as such are useful in the treatment, control or prevention of diseases, disorders or conditions responsive to the modulation of the prolylcarboxypeptidase (PrCP) enzyme. In particular, the compounds of formula I act as inhibitors of the prolylcarboxypeptidase (PrCP) enzyme useful in the treatment, control or prevention of diseases, disorders or conditions responsive to the inhibition of prolylcarboxypeptidase (FRCP), such as eating disorders due to excessive food intake, and the resulting obesity and complications associated therewith, including diabetes, obesity related disorders and diabetes related disorders.

The present invention also relates to pharmaceutical compositions comprising the compounds of the present invention and a pharmaceutically acceptable carrier.

The present invention also relates to methods for the treatment, control, or prevention of disorders, diseases, or conditions responsive to inhibition of prolylcarboxypeptidase in a subject in need thereof by administering the compounds and pharmaceutical compositions of the present invention.

The present invention also relates to methods for the treatment, control, or prevention of obesity, Type 2 diabetes, metabolic syndrome, obesity related disorders and diabetes related disorders by administering the compounds and pharmaceutical compositions of the present invention.

DETAILED DESCRIPTION OF THE INVENTION

The present invention is concerned with spiroether compounds useful as inhibitors of prolylcarboxypeptidase. Compounds of the present invention are described by structural formula I:

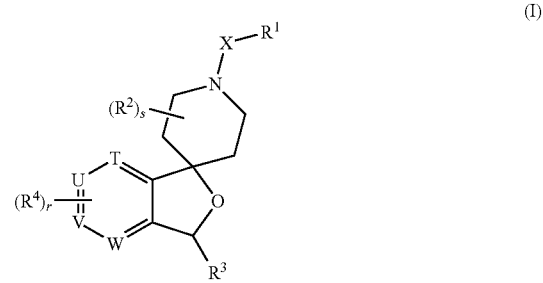

or a pharmaceutically acceptable salt thereof; wherein
each T, U, V and W is independently selected from the group consisting of:
 (1) CH, and
 (2) N,
provided that at least two of T, U, V and W are CH;
each X is independently selected from the group consisting of:
 (1) —$CH_2$—,
 (2) —$CH_2CH_2$—,
 (3) —$SO_2$—,
 (4) —C(O)—, and
 (5) —C(O)$CH_2$—,
wherein each $CH_2$ is unsubstituted or substituted with one or two substituents selected from $R^a$;
each $R^1$ is independently selected from the group consisting of:
 (1) —$C_{3-7}$cycloalkyl,
 (2) —$C_{3-7}$cycloalkenyl,
 (3) —$C_{2-6}$cycloheteroalkyl, (4) —$C_{3-7}$cycloheteroalkenyl,
(5) -aryl, and
(6) -heteroaryl, wherein each cycloalkyl, cycloalkenyl, cycloheteroalkyl, cycloheteroalkenyl, aryl and heteroaryl is unsubstituted or substituted with one to three groups independently selected from $R^b$;

each $R^2$ is independently selected from the group consisting of
(1) hydrogen,
(2) —$C_{1-6}$ alkyl,
(3) —$C_{1-6}$ alkoxy,
(4) halogen,
(5) oxo, and
(6) —OH;

each $R^3$ is independently selected from the group consisting of:
(1) —$(CH_2)_m$—$C_{3-7}$cycloalkyl,
(2) —$(CH_2)_m$—$C_{3-7}$cycloalkenyl,
(3) —$(CH_2)_m$—$C_{2-6}$cycloheteroalkyl,
(4) —$(CH_2)_m$—$C_{3-7}$cycloheteroalkenyl,
(5) —$(CH_2)_m$-aryl, and
(6) —$(CH_2)_m$-heteroaryl, wherein each $CH_2$, cycloalkyl, cycloalkenyl, cycloheteroalkyl, cycloheteroalkenyl, aryl and heteroaryl is unsubstituted or substituted with one, two or three groups independently selected from $R^c$;

each $R^4$ is independently selected from the group consisting of:
(1) hydrogen,
(2) halogen,
(3) —CN,
(4) —$CF_3$,
(5) —$OCF_3$,
(6) —OH,
(7) —$OC_{1-6}$ alkyl, and
(8) —$C_{1-6}$ alkyl, wherein alkyl is unsubstituted or substituted with one to three substituents selected from the group consisting of —OH, halogen, —$C_{1-6}$alkyl, —CN, —$OC_{1-6}$ alkyl, —$CO_2H$, and —$CO_2C_{1-6}$ alkyl;

each $R^a$ is independently selected from the group consisting of:
(1) —$C_{1-6}$ alkyl,
(2) —$(CH_2)_n CO_2 H$,
(3) —$(CH_2)_n CO_2 C_{1-6}$ alkyl,
(4) —$(CH_2)_a$—OH,
(5) oxo,
(6) —$(CH_2)_n$—O—$C_{1-6}$ alkyl,
(7) —$(CH_2)_n$—$N(R^d)_2$, and
(8) —$(CH_2)_n$—S—$C_{1-6}$ alkyl, wherein each $CH_2$, and alkyl is unsubstituted or substituted with one or two groups independently selected from: —OH, —$C_{1-6}$ alkyl, halogen, —CN, —$OC_{1-6}$ alkyl, —$CO_2H$, and —$CO_2C_{1-6}$ alkyl;

each $R^b$ is independently selected from the group consisting of:
(1) hydrogen,
(2) halogen,
(3) —CN,
(4) —$CF_3$,
(5) —$OCF_3$,
(6) —OH,
(7) —$OC_{1-6}$ alkyl,
(8) —$C_{1-6}$ alkyl,
(9) —$SO_2$—$C_{1-6}$ alkyl,
(10) —$(CH_2)_q$—$C_{3-7}$cycloalkyl,
(11) —$(CH_2)_q$—$C_{3-7}$cycloalkenyl,
(12) —$(CH_2)_q$—$C_{2-6}$cycloheteroalkyl,
(13) —$(CH_2)_q$—$C_{2-7}$cycloheteroalkenyl,
(14) —$(CH_2)_q$-aryl, and
(15) —$(CH_2)_q$-heteroaryl, wherein each $CH_2$, alkyl, cycloalkyl, cycloalkenyl, cycloheteroalkyl, cycloheteroalkenyl, aryl and heteroaryl is unsubstituted or substituted with one to three substituents selected from the group consisting of: —OH, —$C_{1-6}$ alkyl, halogen, —CN, —$OC_{1-6}$ alkyl, —$CO_2H$, and —$CO_2C_{1-6}$ alkyl;

each $R^c$ is independently selected from the group consisting of:
(1) hydrogen,
(2) halogen,
(3) —$C_{1-6}$ alkyl,
(4) —CN,
(5) oxo,
(6) —OH,
(7) —$OC_{1-6}$ alkyl,
(8) —$CF_3$, and
(9) —$OCF_3$, wherein alkyl is unsubstituted or substituted with one to three substituents selected from the group consisting of —OH, —$C_{1-6}$ alkyl, halogen, —CN, —$OC_{1-6}$ alkyl, —$CO_2H$, and —$CO_2C_{1-6}$ alkyl;

each $R^d$ is independently selected from the group consisting of:
(1) hydrogen, and
(2) —$C_{1-6}$ alkyl;

m is selected from 0, 1, 2, 3 and 4;
n is selected from 0, 1, 2, 3 and 4;
q is selected from 0, 1, 2, 3 and 4;
r is selected from 0, 1, 2, and 3; and
s is selected from 0, 1, 2 and 3.

In one embodiment of the present invention, each T, U, V and W is independently selected from the group consisting of: CH, and N, provided that at least two of T, U, V and W are CH.

In another embodiment, each T, U, V and W is independently selected from the group consisting of: CH, and N, provided that at least three of T, U, V and W are CH.

In another embodiment, each T is N; and U, V and W are CH.

In another embodiment, each U is N; and T, V and W are CH.

In another embodiment, each V is N; and U, T and W are CH.

In another embodiment, each W is N; and U, V and T are CH.

In another embodiment, T is N and U, V and W are CH, or T, U, V and W are CH.

In another embodiment of the present invention, each X is independently selected from the group consisting of: —$CH_2$—, —$CH_2CH_2$—, —$SO_2$—, —C(O)—, and —C(O)$CH_2$—, wherein each $CH_2$ is unsubstituted or substituted with one or two substituents selected from $R^a$.

In another embodiment of the present invention, each X is selected from the group consisting of: —C(O)—, and —C(O)$CH_2$—, wherein $CH_2$ is unsubstituted or substituted with one or two substituents selected from $R^a$. In a class of this embodiment, X is —C(O)—. In another class of this embodiment, X is —C(O)$CH_2$—, wherein $CH_2$ is unsubstituted or substituted with one or two substituents selected from $R^a$. In a class of this embodiment, X is —C(O)—. In another class of this embodiment, X is —C(O)$CH_2$—. In another embodiment of the present invention, each X is independently selected from the group consisting of: —$CH_2$—, —$CH_2CH_2$—, and —$SO_2$—, wherein each $CH_2$ is unsubstituted or substituted with one or two substituents selected from $R^a$. In a class of this embodiment, each X is independently selected from the group consisting of: —$CH_2$—, —$CH_2CH_2$—, and —$SO_2$—. In another embodiment of the present invention, each X is —$CH_2CH_2$—, wherein each $CH_2$ is unsubstituted or substituted with one or two substituents selected from $R^a$. In a class of this embodiment, X is —$CH_2CH_2$—. In another embodiment of the present invention, each X is independently selected from the group consisting of: —$CH_2$—, and —$SO_2$—, wherein $CH_2$ is unsubstituted or substituted with one or two substituents selected from $R^a$. In a class of this embodiment, each X is independently selected from the group consisting of: —$CH_2$—, and —$SO_2$—. In another embodiment of the present invention, X is —$CH_2$—, wherein $CH_2$ is unsubstituted or substituted with one or two substituents selected from $R^a$. In another embodiment of the present invention, X is —$SO_2$—.

In another embodiment of the present invention, each $R^1$ is independently selected from the group consisting of: —$C_{3-7}$cycloalkyl, —$C_{3-7}$cycloalkenyl, —$C_{2-6}$cycloheteroalkyl, —$C_{3-7}$cycloheteroalkenyl, -aryl, and -heteroaryl, wherein each cycloalkyl, cycloalkenyl, cycloheteroalkyl, cycloheteroalkenyl, aryl and heteroaryl is unsubstituted or substituted with one to three groups independently selected from $R^b$. In another embodiment of the present invention, each $R^1$ is independently selected from the group consisting of: —$C_{3-7}$cycloalkyl, —$C_{2-6}$cycloheteroalkyl, aryl, and heteroaryl, wherein each cycloalkyl, cycloheteroalkyl, aryl and heteroaryl is unsubstituted or substituted with one to three groups independently selected from $R^b$. In a class of this embodiment, each $R^1$ is independently selected from the group consisting of: cyclopropyl, cyclobutyl, cyclohexyl, pyrrolidine, azabicyclo[2.2.1]heptane, phenyl, pyridine, pyrazine, pyridazine, pyrimidine, thiophene, benzodioxole, naphthalene, benzofuran, oxazole, thiazole, triazole, benzisoxazole, and imidazopyrimidine, wherein each cycloalkyl, cycloheteroalkyl, aryl and heteroaryl is unsubstituted or substituted with one to three groups independently selected from $R^b$.

In another embodiment of the present invention, each $R^1$ is independently selected from the group consisting of: —$C_{3-7}$cycloalkyl, aryl, and heteroaryl, wherein each cycloalkyl, aryl and heteroaryl is unsubstituted or substituted with one to three groups independently selected from $R^b$. In a class of this embodiment, each $R^1$ is independently selected from the group consisting of cyclopropyl, cyclobutyl, cyclohexyl, phenyl, pyridine, pyrazine, pyridazine, pyrimidine, thiophene, benzodioxole, naphthalene, benzofuran, oxazole, thiazole, triazole, benzisoxazole, and imidazopyrimidine, wherein each cycloalkyl, aryl and heteroaryl is unsubstituted or substituted with one to three groups independently selected from $R^b$. In another class of this embodiment, each $R^1$ is independently selected from the group consisting of: cyclopropyl, cyclobutyl, cyclohexyl, phenyl, pyridine, pyridazine, pyrimidine, naphthalene, thiazole, benzisoxazole, and imidazopyrimidine, wherein each cycloalkyl, aryl and heteroaryl is unsubstituted or substituted with one to three groups independently selected from $R^b$.

In another embodiment of the present invention, each $R^1$ is independently selected from the group consisting of aryl, and heteroaryl, wherein each aryl and heteroaryl is unsubstituted or substituted with one to three groups independently selected from $R^b$. In a class of this embodiment, each $R^1$ is independently selected from the group consisting of phenyl, and pyridine, wherein each phenyl and pyridine is unsubstituted or substituted with one to three groups independently selected from $R^b$.

In another embodiment of the present invention, $R^1$ is aryl, wherein aryl is unsubstituted or substituted with one to three groups independently selected from $R^b$. In a class of this embodiment, $R^1$ is phenyl, wherein phenyl is unsubstituted or substituted with one to three groups independently selected from $R^b$. In another embodiment of the present invention, $R^1$ is heteroaryl, wherein heteroaryl is unsubstituted or substituted with one to three groups independently selected from $R^b$. In a class of this embodiment, $R^1$ is pyridine, wherein pyridine is unsubstituted or substituted with one to three groups independently selected from $R^b$.

In another embodiment of the present invention, each $R^2$ is independently selected from the group consisting of: hydrogen, —$C_{1-6}$ alkyl, —$CH_3$, —$C_{1-6}$ alkoxy, halogen, oxo, and —OH. In a class f this embodiment, each $R^2$ is independently selected from the group consisting of: hydrogen, —$C_{1-6}$ alkyl, oxo, and —OH. In a subclass of this class, each $R^2$ is independently selected from the group consisting of hydrogen, —$CH_3$, oxo, and —OH. In another class of this embodiment, each $R^2$ is independently selected from the group consisting of —$C_{1-6}$ alkyl, oxo, and —OH. In a subclass of this class, each $R^2$ is independently selected from the group consisting of: —$CH_3$, oxo, and —OH. In another class f this embodiment, $R^2$ is hydrogen.

In another embodiment of the present invention, each $R^3$ is independently selected from the group consisting of: —$(CH_2)_m$—$C_{3-7}$cycloalkyl, —$(CH_2)_m$—$C_{3-7}$cycloalkenyl, —$(CH_2)_m$—$C_{2-6}$cycloheteroalkyl, —$(CH_2)_m$—$C_{3-7}$cycloheteroalkenyl, —$(CH_2)_m$-aryl, and —$(CH_2)_m$-heteroaryl, wherein each $CH_2$, cycloalkyl, cycloalkenyl, cycloheteroalkyl, cycloheteroalkenyl, aryl and heteroaryl is unsubstituted or substituted with one, two or three groups independently selected from $R^c$.

In a class of this embodiment, each $R^3$ is independently selected from the group consisting of: —$(CH_2)_m$-aryl, and —$(CH_2)_m$-heteroaryl, wherein each $CH_2$, aryl and heteroaryl is unsubstituted or substituted with one, two or three groups independently selected from $R^c$.

In another class of this embodiment, each $R^3$ is independently selected from the group consisting of: -aryl, and -heteroaryl, wherein each aryl and heteroaryl is unsubstituted or substituted with one to three groups independently selected from $R^c$. In another class of this embodiment, each $R^3$ is independently selected from the group consisting of: -phenyl, and -pyridine, wherein each phenyl and pyridine is unsubstituted or substituted with one to three groups independently selected from $R^c$. In another class of this embodiment, each $R^3$ is independently selected from the group consisting of: phenyl, pyridine, pyridine N-oxide, and pyridine N-hydroxide, wherein each phenyl and pyridine is unsubstituted or substituted with one to two groups independently selected from $R^c$. In another class of this embodiment, each $R^3$ is independently selected from the group consisting of: phenyl, pyridine, and pyridine N-oxide; wherein each phenyl and pyridine is unsubstituted or substituted with one to two groups independently selected from $R^c$.

In another class of this embodiment, each $R^3$ is -aryl, wherein aryl is unsubstituted or substituted with one to three groups independently selected from $R^c$. In another class of this embodiment, each $R^3$ is phenyl, wherein phenyl is unsubstituted or substituted with one to two groups independently selected from $R^c$. In another class of this embodiment, each $R^3$ is -heteroaryl, wherein heteroaryl is unsubstituted or substituted with one to three groups independently selected from $R^c$. In another class of this embodiment, each $R^3$ is pyridine, wherein pyridine is unsubstituted or substituted with one to two groups independently selected from $R^c$.

In another embodiment of the present invention, each $R^4$ is independently selected from the group consisting of hydrogen, halogen, —CN, —$CF_3$, —$OCF_3$, —OH, —$OC_{1-6}$ alkyl, and —$C_{1-6}$ alkyl, wherein alkyl is unsubstituted or substituted with one to three substituents selected from the group consisting of: —OH, halogen, —$C_{1-6}$alkyl, —CN, —$OC_{1-6}$ alkyl, —$CO_2H$, and —$CO_2C_{1-6}$ alkyl. In a class of this embodiment, each $R^4$ is independently selected from the group consisting of: hydrogen, halogen, —CN, —$CF_3$, —$OCF_3$, —OH, —$OC_{1-6}$ alkyl, and —$C_{1-6}$ alkyl, wherein alkyl is unsubstituted or substituted with one to three substituents selected from the group consisting of: halogen and —$C_{1-6}$alkyl.

In another class of this embodiment, each $R^4$ is independently selected from the group consisting of: hydrogen, halogen, and —$C_{1-6}$ alkyl, wherein alkyl is unsubstituted or substituted with one to three substituents selected from the group consisting of —OH, halogen, —$C_{1-6}$alkyl, —CN, —$OC_{1-6}$ alkyl, —$CO_2H$, and —$CO_2C_{1-6}$ alkyl. In another class of this embodiment, each $R^4$ is independently selected from the group consisting of: hydrogen, halogen, and —$C_{1-6}$ alkyl, wherein alkyl is unsubstituted or substituted with one to three substituents selected from the group consisting of: halogen and —$C_{1-6}$alkyl. In a subclass of this class, each $R^4$ is independently selected from the group consisting of: hydrogen, halogen, and —$C_{1-6}$ alkyl, wherein alkyl is unsubstituted or substituted with one to three substituents selected from the group consisting of: halogen and —$C_{1-6}$alkyl. In a subclass of this class, each $R^4$ is independently selected from the group consisting of: hydrogen, Cl, F and —$CH_3$, wherein alkyl is unsubstituted or substituted with one to three substituents selected from the group consisting of halogen and —$C_{1-6}$alkyl. In a subclass of this class, each $R^4$ is independently selected from the group consisting of: hydrogen, Cl and —$CH_3$.

In another class of this embodiment, each $R^4$ is independently selected from the group consisting of: halogen, and —$C_{1-6}$ alkyl, wherein alkyl is unsubstituted or substituted with one to three substituents selected from the group consisting of halogen and —$C_{1-6}$alkyl. In a subclass of this class, each $R^4$ is independently selected from the group consisting of: Cl, F and —$CH_3$, wherein alkyl is unsubstituted or substituted with one to three substituents selected from the group consisting of: halogen and —$C_{1-6}$alkyl. In a subclass of this class, each $R^4$ is independently selected from the group consisting of: Cl and —$CH_3$. In another class of this embodiment, each $R^4$ is hydrogen.

In another embodiment of the present invention, each $R^a$ is independently selected from the group consisting of —$C_{1-6}$ alkyl, —$(CH_2)_nCO_2H$, —$(CH_2)_nCO_2C_{1-6}$ alkyl, —$(CH_2)_n$—OH, oxo, —$(CH_2)_n$—O—$C_{1-6}$ alkyl, —$(CH_2)_n$—$N(R^d)_2$, and —$(CH_2)_n$—S—$C_{1-6}$ alkyl, wherein each $CH_2$, and alkyl is unsubstituted or substituted with one or two groups independently selected from: —OH, —$C_{1-6}$ alkyl, halogen, —CN, —$OC_{1-6}$ alkyl, —$CO_2H$, and —$CO_2C_{1-6}$ alkyl. In a class of this embodiment, each $R^a$ is independently selected from the group consisting of: —$C_{1-6}$ alkyl, —$(CH_2)_nCO_2H$, —$(CH_2)_nCO_2C_{1-6}$ alkyl, —$(CH_2)_n$—OH, oxo, —$(CH_2)_n$—O—$C_{1-6}$ alkyl, —$(CH_2)_n$—$N(R^d)_2$, and —$(CH_2)_n$—S—$C_{1-6}$ alkyl, wherein each $CH_2$, and alkyl is unsubstituted or substituted with one or two groups independently selected from: —OH, —$C_{1-6}$ alkyl, and halogen.

In another embodiment of the present invention, each $R^a$ is independently selected from the group consisting of: —$C_{1-6}$ alkyl, —$(CH_2)_nCO_2H$, —$(CH_2)_nCO_2C_{1-6}$ alkyl, —$(CH_2)_n$—OH, and oxo, wherein each $C_{1-12}$, and alkyl is unsubstituted or substituted with one or two groups independently selected from: —OH, —$C_{1-6}$ alkyl, halogen, —CN, —$OC_{1-6}$ alkyl, —$CO_2H$, and —$CO_2C_{1-6}$ alkyl. In a class of this embodiment, each $R^a$ is independently selected from the group consisting of: —$C_{1-6}$ alkyl, —$(CH_2)_nCO_2H$, —$(CH_2)_nCO_2C_{1-6}$ alkyl, —$(CH_2)_n$—OH, and oxo, wherein each $CH_2$, and alkyl is unsubstituted or substituted with one or two groups independently selected from: —OH, —$C_{1-6}$ alkyl, and halogen.

In another embodiment of the present invention, each $R^a$ is independently selected from the group consisting of —$C_{1-6}$ alkyl, —$CO_2H$, —$CO_2C_{1-6}$ alkyl, and —$(CH_2)_n$—OH, wherein each $CH_2$, and alkyl is unsubstituted or substituted with one or two groups independently selected from: —OH, —$C_{1-6}$ alkyl, halogen, —CN, —$OC_{1-6}$ alkyl, —$CO_2H$, and —$CO_2C_{1-6}$ alkyl. In a class of this embodiment, each $R^a$ is independently selected from the group consisting of: —$C_{1-6}$ alkyl, —$CO_2H$, —$CO_2C_{1-6}$ alkyl, and —$(CH_2)_n$—OH, wherein each $CH_2$, and alkyl is unsubstituted or substituted with one or two groups independently selected from: —OH, —$C_{1-6}$ alkyl, and halogen.

In another embodiment of the present invention, each $R^a$ is independently selected from the group consisting of —$CH_3$, —$CH_2F$, —$CO_2H$—$CO_2CH_2CH_3$, —$CH_2OH$, and —$C(CH_3)_2OH$, wherein each $CH_2$, and alkyl is unsubstituted or substituted with one or two groups independently selected from: —OH, —$C_{1-6}$ alkyl, and halogen. In a class of this embodiment, each $R^a$ is independently selected from the group consisting of: —$CH_3$, —$CO_2H$—$CO_2CH_2CH_3$, $CH_2OH$, and —$C(CH_3)_2OH$, wherein each $CH_2$, and alkyl is unsubstituted or substituted with one or two groups independently selected from: —OH, —$C_{1-6}$ alkyl, and halogen.

In another embodiment of the present invention, each $R^a$ is independently selected from the group consisting of: —$CO_2C_{1-6}$ alkyl, and —$(CH_2)_n$—OH, wherein each $CH_2$, and alkyl is unsubstituted or substituted with one or two groups independently selected from: —OH, —$C_{1-6}$ alkyl, halogen, —CN, —$OC_{1-6}$ alkyl, —$CO_2H$, and —$CO_2C_{1-6}$ alkyl. In a class of this embodiment, each $R^a$ is independently selected from the group consisting of: —$CO_2CH_2CH_3$, —$CH_2OH$, and —$C(CH_3)_2OH$, wherein each $CH_2$, and alkyl is unsubstituted or substituted with one or two groups independently selected from: —OH, —$C_{1-6}$ alkyl, and halogen.

In another embodiment of the present invention, each $R^a$ is independently selected from the group consisting of: —$C_{1-6}$ alkyl, and —$CO_2H$, wherein each $CH_2$, and alkyl is unsubstituted or substituted with one or two groups independently selected from: —OH, —$C_{1-6}$ alkyl, halogen, —CN, —$OC_{1-6}$ alkyl, —$CO_2H$, and —$CO_2C_{1-6}$ alkyl. In a class of this embodiment, each $R^a$ is independently selected from the group consisting of: —$CH_3$, —$CH_2F$, and —$CO_2H$, wherein each $CH_2$, and alkyl is unsubstituted or substituted with one or two groups independently selected from: —OH, —$C_{1-6}$ alkyl, and halogen. In another class of this embodiment, each $R^a$ is independently selected from the group consisting of: —$CH_3$, and —$CO_2H$, wherein alkyl is unsubstituted or substituted with one or two groups independently selected from: —OH, —$C_{1-6}$ alkyl, halogen, —CN, —$OC_{1-6}$ alkyl, —$CO_2H$, and —$CO_2C_{1-6}$ alkyl. In another class of this embodiment, each $R^a$ is independently selected from the group consisting of: —$CH_3$, and —$CO_2H$, wherein alkyl is unsubstituted or substituted with one or two groups independently selected from: —OH, —$C_{1-6}$ alkyl, and halogen. In another class of this embodiment, each $R^a$ is independently selected from the group consisting of: —$CH_3$, and —$CO_2H$, wherein alkyl is unsubstituted or substituted with one or two groups independently selected from: —$C_{1-6}$ alkyl, In another class of this embodiment, each $R^a$ is independently selected from the group consisting of —CH$_3$, and —CO$_2$H, wherein alkyl is unsubstituted or substituted with one or two —CH$_3$ groups.

In another embodiment of the present invention, each R$^b$ is independently selected from the group consisting of: hydrogen, halogen, —CN, —CF$_3$, —OCF$_3$, —OH, —OC$_{1-6}$ alkyl, —C$_{1-6}$ alkyl, —SO$_2$—C$_{1-6}$ alkyl, —(CH$_2$)$_q$—C$_{3-7}$cycloalkyl, —(CH$_2$)$_q$—C$_{3-7}$cycloalkenyl, —(CH$_2$)$_q$—C$_{2-6}$cycloheteroalkyl, —(CH$_2$)$_q$—C$_{2-7}$cycloheteroalkenyl, —(CH$_2$)$_q$-aryl, and —(CH$_2$)$_q$-heteroaryl, wherein each CH$_2$, alkyl, cycloalkyl, cycloalkenyl, cycloheteroalkyl, cycloheteroalkenyl, aryl and heteroaryl is unsubstituted or substituted with one to three substituents selected from the group consisting of —OH, —C$_{1-6}$ alkyl, halogen, —CN, —OC$_{1-6}$ alkyl, —CO$_2$H, and —CO$_2$C$_{1-6}$ alkyl.

In another embodiment of the present invention, each R$^b$ is independently selected from the group consisting of: hydrogen, halogen, —CF$_3$, —OCF$_3$, —OC$_{1-6}$ alkyl, —C$_{1-6}$ alkyl, —SO$_2$—C$_{1-6}$ alkyl, —(CH$_2$)$_q$—C$_{2-6}$cycloheteroalkyl, —(CH$_2$)$_q$—C$_{2-7}$cycloheteroalkenyl, —(CH$_2$)$_q$-aryl, and —(CH$_2$)$_q$-heteroaryl, wherein each CH$_2$, alkyl, cycloheteroalkyl, cycloheteroalkenyl, aryl and heteroaryl is unsubstituted or substituted with one to three substituents selected from the group consisting of: —OH, —C$_{1-6}$ alkyl, halogen, —CN, —OC$_{1-6}$ alkyl, —CO$_2$H, and —CO$_2$C$_{1-6}$ alkyl.

In another embodiment of the present invention, each R$^b$ is independently selected from the group consisting of: hydrogen, halogen, —CF$_3$, —OCF$_3$, —OC$_{1-6}$ alkyl, —C$_{1-6}$ alkyl, —SO$_2$—C$_{1-6}$ alkyl, —C$_{2-6}$cycloheteroalkyl, —C$_{2-7}$cycloheteroalkenyl, aryl, and heteroaryl, wherein each alkyl, cycloheteroalkyl, cycloheteroalkenyl, aryl and heteroaryl is unsubstituted or substituted with one to three substituents selected from the group consisting of: —C$_{1-6}$ alkyl, halogen, —CN, and —CO$_2$C$_{1-6}$ alkyl. In a class of this embodiment, each R$^b$ is independently selected from the group consisting of: hydrogen, Br, F, Cl, —CF$_3$, —OCF$_3$, —OCH$_3$, OCHF$_2$, —CH$_3$, —SO$_2$CH$_3$, morpholine, pyrrolidine, piperidine, piperazine, tetrahydropyridine, phenyl, pyridine, pyrazole, and oxazole, wherein each alkyl, cycloheteroalkyl, cycloheteroalkenyl, aryl and heteroaryl is unsubstituted or substituted with one to three substituents selected from the group consisting of: —C$_{1-6}$ alkyl, halogen, —CN, and —CO$_2$C$_{1-6}$ alkyl. In another class of this embodiment, In a class of this embodiment, each R$^b$ is independently selected from the group consisting of: hydrogen, Br, F, Cl, —CF$_3$, —OCF$_3$, —OCH$_3$, OCHF$_2$, —CH$_3$, wherein each alkyl is unsubstituted or substituted with one to three halogen substituents. In another class of this embodiment, each R$^b$ is independently selected from the group consisting of: Br, F, Cl, —CF$_3$, —OCF$_3$, —OCH$_3$, OCHF$_2$, —CH$_3$, wherein each alkyl is unsubstituted or substituted with one to three halogen substituents. In another class of this embodiment, each R$^b$ is independently selected from the group consisting of: hydrogen, F, —CF$_3$, —OCF$_3$, and —OCHF$_2$. In another class of this embodiment, each R$^b$ is independently selected from the group consisting of: F, —CF$_3$, —OCF$_3$, and —OCHF$_2$.

In another embodiment of the present invention, each R$^b$ is independently selected from the group consisting of: hydrogen, halogen, —CF$_3$, —OCF$_3$, —OC$_{1-6}$ alkyl, and —C$_{1-6}$ alkyl, wherein each alkyl is unsubstituted or substituted with one to three substituents selected from the group consisting of: —OH, —C$_{1-6}$ alkyl, halogen, —CN, and —CO$_2$C$_{1-6}$ alkyl. In a class of this embodiment, each R$^b$ is independently selected from the group consisting of: hydrogen, Br, F, Cl, —CF$_3$, —OCF$_3$, —OCH$_3$, —OCHF$_2$, and —CH$_3$.

In another embodiment of the present invention, each R$^b$ is independently selected from the group consisting of halogen, —CF$_3$, —OCF$_3$, —OC$_{1-6}$ alkyl, —C$_{1-6}$ alkyl, wherein each alkyl is unsubstituted or substituted with one to three substituents selected from the group consisting of: —C$_{1-6}$ alkyl, halogen, —CN, and —CO$_2$C$_{1-6}$ alkyl. In a class of this embodiment, each R$^b$ is independently selected from the group consisting of: Br, F, Cl, —CF$_3$, —OCF$_3$, —OCHF$_2$, and —CH$_3$.

In another embodiment of the present invention, each R$^b$ is independently selected from the group consisting of halogen, —OC$_{1-6}$ alkyl, —C$_{1-6}$ alkyl, wherein each alkyl is unsubstituted or substituted with one to three substituents selected from the group consisting of: —OH, —C$_{1-6}$ alkyl, halogen, —CN, —OC$_{1-6}$ alkyl, —CO$_2$H, and —CO$_2$C$_{1-6}$ alkyl. In a class of this embodiment, each R$^b$ is independently selected from the group consisting of: Br, F, Cl, —OCH$_3$, —OCHF$_2$, and —CH$_3$, wherein each alkyl is unsubstituted or substituted with one to three substituents selected from the group consisting of —C$_{1-6}$ alkyl, halogen, —CN, and —CO$_2$C$_{1-6}$ alkyl. In another class of this embodiment, each R$^b$ is independently selected from the group consisting of: Br, F, Cl, —OCH$_3$, —OCHF$_2$, and —CH$_3$.

In another embodiment of the present invention, each R$^b$ is independently selected from the group consisting of: halogen, —CF$_3$, —OCF$_3$, and —OC$_{1-6}$ alkyl, wherein each alkyl is unsubstituted or substituted with one to three substituents selected from the group consisting of: OH, —C$_{1-6}$ alkyl, halogen, —CN, —OC$_{1-6}$ alkyl, —CO$_2$H, and —CO$_2$C$_{1-6}$ alkyl. In a class of this embodiment, each R$^b$ is independently selected from the group consisting of halogen, —CF$_3$, OCF$_3$, and —OC$_{1-6}$ alkyl, wherein each alkyl is unsubstituted or substituted with one to three substituents selected from the group consisting of: halogen. In another class of this embodiment, each R$^b$ is independently selected from the group consisting of: halogen, —CF$_3$, —OCF$_3$, and —OC$_{1-6}$ alkyl, wherein each alkyl is unsubstituted or substituted with one to three fluoro substituents. In another class of this embodiment, each R$^b$ is independently selected from the group consisting of: Br, F, Cl, —CF$_3$, —OCF$_3$, —OCH$_3$, —OCHF$_2$, wherein each alkyl is unsubstituted or substituted with one to three substituents selected from the group consisting of: —C$_{1-6}$ alkyl, halogen, —CN, and —CO$_2$C$_{1-6}$ alkyl. In another class of this embodiment, each R$^b$ is independently selected from the group consisting of: Br, F, Cl, —CF$_3$, —OCF$_3$, —OCH$_3$, —OCHF$_2$, wherein each alkyl is unsubstituted or substituted with one to three substituents selected from the group consisting of: —C$_{1-6}$ alkyl, and halogen. In another class of this embodiment, each R$^b$ is independently selected from the group consisting of: Br, F, Cl, —CF$_3$, —OCF$_3$, and —OCHF$_2$. In another class of this embodiment, each R$^b$ is independently selected from the group consisting of: F, —CF$_3$, —OCF$_3$, and —OCHF$_2$.

In another embodiment of the present invention, each R$^c$ is independently selected from the group consisting of: hydrogen, halogen, —C$_{1-6}$ alkyl, —CN, oxo, —OH, —OC$_{1-6}$ alkyl, —CF$_3$, and —OCF$_3$, wherein alkyl is unsubstituted or substituted with one to three substituents selected from the group consisting of: —OH, —C$_{1-6}$ alkyl, halogen, —CN, —OC$_{1-6}$ alkyl, —CO$_2$H, and —CO$_2$C$_{1-6}$ alkyl. In a class of this embodiment, each R$^c$ is independently selected from the group consisting of: hydrogen, halogen, —C$_{1-6}$ alkyl, —CN, oxo, —OH, —OC$_{1-6}$ alkyl, —CF$_3$, and —OCF$_3$, wherein alkyl is unsubstituted or substituted with one to three substituents selected from the group consisting of: —C$_{1-6}$ alkyl, and halogen. In another class of this embodiment, each R$^c$ is independently selected from the group consisting of: hydrogen, halogen, —C$_{1-6}$ alkyl, oxo, and OH, wherein alkyl is unsubstituted or substituted with one to three substituents selected from the group consisting of —OH, —$C_{1-6}$ alkyl, halogen, —CN, —$OC_{1-6}$ alkyl, —$CO_2H$, and —$CO_2C_{1-6}$ alkyl. In another class of this embodiment, each $R^c$ is independently selected from the group consisting of: hydrogen, halogen, —$C_{1-6}$ alkyl, oxo, and —OH, wherein alkyl is unsubstituted or substituted with one to three substituents selected from the group consisting of: —$C_{1-6}$ alkyl, and halogen. In a subclass of this class, each $R^c$ is independently selected from the group consisting of: hydrogen, Cl, F, —$CH_3$, oxo, and —OH, wherein alkyl is unsubstituted or substituted with one to three substituents selected from the group consisting of: —$C_{1-6}$ alkyl, and halogen. In another subclass of this class, each $R^c$ is independently selected from the group consisting of: halogen, —$C_{1-6}$ alkyl, oxo, and —OH, wherein alkyl is unsubstituted or substituted with one to three substituents selected from the group consisting of: —$C_{1-6}$ alkyl, and halogen. In another subclass of this class, each $R^c$ is independently selected from the group consisting of: Cl, F, —$CH_3$, oxo, and —OH, wherein alkyl is unsubstituted or substituted with one to three substituents selected from the group consisting of: —$C_{1-6}$ alkyl, and halogen. In another subclass of this class, each $R^c$ is independently selected from the group consisting of: F, —$CH_3$, and —OH, wherein alkyl is unsubstituted or substituted with one to three substituents selected from the group consisting of: —$C_{1-6}$ alkyl, and halogen. In another class of this embodiment, each $R^c$ is independently selected from the group consisting of hydrogen, halogen, and oxo. In another subclass of this class, each $R^c$ is independently selected from the group consisting of: hydrogen, Cl, F, and oxo. In another subclass of this class, each $R^c$ is independently selected from the group consisting of: hydrogen, Cl, and oxo. In another subclass of this class, $R^c$ is hydrogen or Cl. In another subclass of this class, $R^c$ is hydrogen or oxo. In another subclass of this class, each $R^c$ is independently selected from the group consisting of: halogen, and oxo. In another subclass of this class, each $R^c$ is independently selected from the group consisting of Cl, F, and oxo. In another subclass of this class, each $R^c$ is independently selected from the group consisting of: Cl, and oxo. In another subclass of this class, $R^c$ is Cl. In another subclass of this class, $R^c$ is oxo.

In another embodiment of the present invention, each $R^d$ is independently selected from the group consisting of: hydrogen, and —$C_{1-6}$ alkyl. In a class of this embodiment, $R^d$ is hydrogen. In another class of this embodiment, $R^d$ is —$C_{1-6}$ alkyl.

In another embodiment of the present invention, m is 0, 1, 2, 3 or 4. In a class of this embodiment, m is 0, 1, 2, or 3. In another class of this embodiment, m is 0, 1 or 2. In another class of this embodiment, m is 0 or 1. In another class of this embodiment, m is 1 or 2.
In another class of this embodiment, m is 0 or 2. In another class of this embodiment, m is 2 or 3. In another class of this embodiment, m is 1 or 3. In another class of this embodiment, m is 0, 1 or 3. In another class of this embodiment, m is 0. In another class of this embodiment, m is 1. In another class of this embodiment, m is 2. In another class of this embodiment, m is 3. In another class of this embodiment, m is 4.

In another embodiment of the present invention, n is 0, 1, 2, 3 or 4. In a class of this embodiment, n is 0, 1, 2, or 3. In another class of this embodiment, n is 0, 1 or 2. In another class of this embodiment, n is 0 or 1. In another class of this embodiment, n is 1 or 2.

In another class of this embodiment, n is 0 or 2. In another class of this embodiment, n is 2 or 3. In another class of this embodiment, n is 1 or 3. In another class of this embodiment, n is 0, 1 or 3. In another class of this embodiment, n is 0. In another class of this embodiment, n is 1. In another class of this embodiment, n is 2. In another class of this embodiment, n is 3. In another class of this embodiment, n is 4.

In another embodiment of the present invention, q is 0, 1, 2, 3 or 4. In a class of this embodiment, q is 0, 1, 2, or 3. In another class of this embodiment, q is 0, 1 or 2. In another class of this embodiment, q is 0 or 1. In another class of this embodiment, q is 1 or 2.

In another class of this embodiment, q is 0 or 2. In another class of this embodiment, q is 2 or 3. In another class of this embodiment, q is 1 or 3. In another class of this embodiment, q is 0, 1 or 3. In another class of this embodiment, q is 0. In another class of this embodiment, q is 1. In another class of this embodiment, q is 2. In another class of this embodiment, q is 3. In another class of this embodiment, q is 4.

In another embodiment of the present invention, r is 0, 1, 2 or 3. In a class of this embodiment, r is 0, 1 or 2. In another class of this embodiment, r is 0 or 1. In another class of this embodiment, r is 1 or 2. In another class of this embodiment, r is 0 or 2. In another class of this embodiment, r is 0. In another class of this embodiment, r is 1. In another class of this embodiment, r is 2. In another class of this embodiment, r is 3.

In another embodiment of the present invention, s is 0, 1, 2 or 3. In a class of this embodiment, s is 0, 1 or 2. In another class of this embodiment, s is 0 or 1. In another class of this embodiment, s is 1 or 2. In another class of this embodiment, s is 0 or 2. In another class of this embodiment, s is 0. In another class of this embodiment, s is 1. In another class of this embodiment, s is 2. In another class of this embodiment, s is 3.

In another embodiment of the present invention, the invention relates to compounds of structural formula I, wherein:
each T, U, V and W is independently selected from the group consisting of:
  (1) CH, and
  (2) N,
provided that at least three of T, U, V and W are CH;
each $R^3$ is independently selected from the group consisting of:
  (1) -aryl, and
  (2) -heteroaryl,
wherein each aryl and heteroaryl is unsubstituted or substituted with one to three groups independently selected from $R^c$;
each X is independently selected from the group consisting of:
  (1) —$CH_2$—,
  (2) —$CH_2CH_2$—, and
  (3) —$SO_2$—,
wherein each $CH_2$ is unsubstituted or substituted with one or two substituents selected from $R^a$;
each $R^4$ is independently selected from the group consisting of:
  (1) hydrogen,
  (2) halogen, and
  (3) —$C_{1-6}$ alkyl, wherein alkyl is unsubstituted or substituted with one to three substituents selected from the group consisting of: —OH, halogen, —$C_{1-6}$alkyl, —CN, —$OC_{1-6}$ alkyl, —$CO_2H$, and —$CO_2C_{1-6}$ alkyl;

each $R^2$ is independently selected from the group consisting of:
(1) hydrogen,
(2) —$C_{1-6}$ alkyl,
(3) oxo, and
(4) —OH;

each $R^1$ is independently selected from the group consisting of:
(1) —$C_{3-7}$cycloalkyl,
(2) -aryl, and
(3) -heteroaryl,
wherein each cycloalkyl, aryl and heteroaryl is unsubstituted or substituted with one to three groups independently selected from $R^b$;
or a pharmaceutically acceptable salt thereof.

In another embodiment of the present invention, the invention relates to compounds of structural formula I, wherein:
T is N and U, V and W are CH, or T, U, V and W are CH;
each $R^3$ is independently selected from the group consisting of:
(1) -phenyl, and
(2) -pyridine,
wherein each phenyl and pyridine is unsubstituted or substituted with one to three groups independently selected from $R^c$;
each X is independently selected from the group consisting of:
(1) —$CH_2$—, and
(2) —$SO_2$—,
wherein $CH_2$ is unsubstituted or substituted with one or two substituents selected from $R^a$;
$R^4$ is hydrogen;
$R^2$ is hydrogen;
each $R^1$ is independently selected from the group consisting of:
(1) phenyl, and
(2) pyridine,
wherein each phenyl and pyridine is unsubstituted or substituted with one to three groups independently selected from $R^b$;
or a pharmaceutically acceptable salt thereof.

In another embodiment of the present invention, the invention relates to compounds of structural formula Ia:

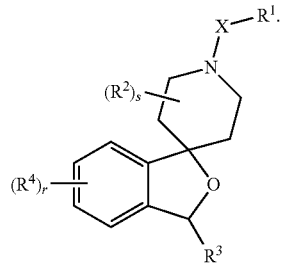

(Ia)

In another embodiment of the present invention, the invention relates to compounds of structural formula Ib:

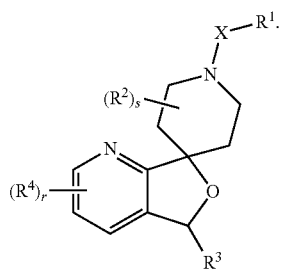

(Ib)

In another embodiment of the present invention, the invention relates to compounds of structural formula Ic:

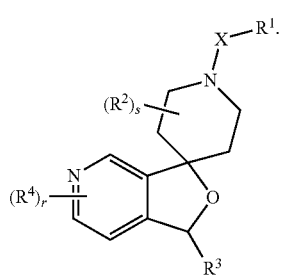

(Ic)

In another embodiment of the present invention, the invention relates to compounds of structural formula Id:

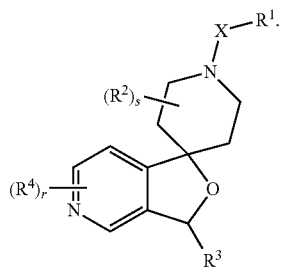

(Id)

In another embodiment of the present invention, the invention relates to compounds of structural formula Ie:

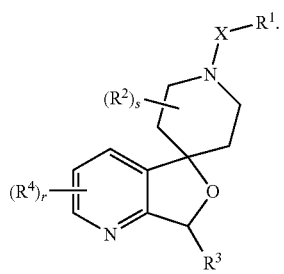

(Ie)

Illustrative, but nonlimiting, examples of compounds of the present invention that are useful as inhibitors of PRCP are the following:

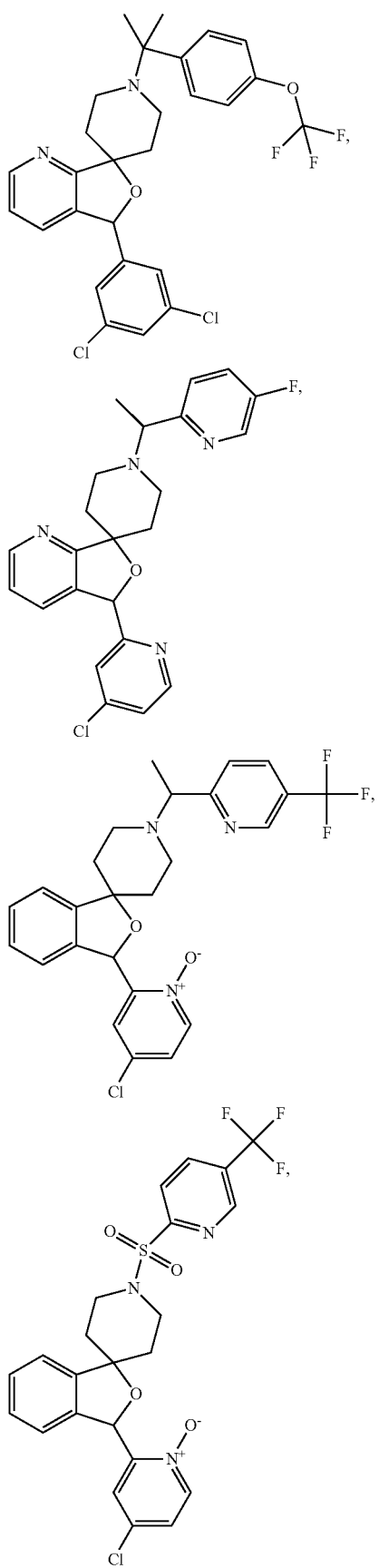 [SMILES: CC(C)(c1ccc(OC(F)(F)F)cc1)N1CCC2(CC1)OC(c1cc(Cl)cc(Cl)c1)c1cccnc12 ; CC(c1ccc(F)cn1)N1CCC2(CC1)OC(c1cc(Cl)ccn1)c1cccnc12 ; CC(c1ccc(C(F)(F)F)cn1)N1CCC2(CC1)OC(c1cc(Cl)cc[n+]1[O-])c1ccccc12 ; O=S(=O)(c1ccc(C(F)(F)F)cn1)N1CCC2(CC1)OC(c1cc(Cl)cc[n+]1[O-])c1ccccc12]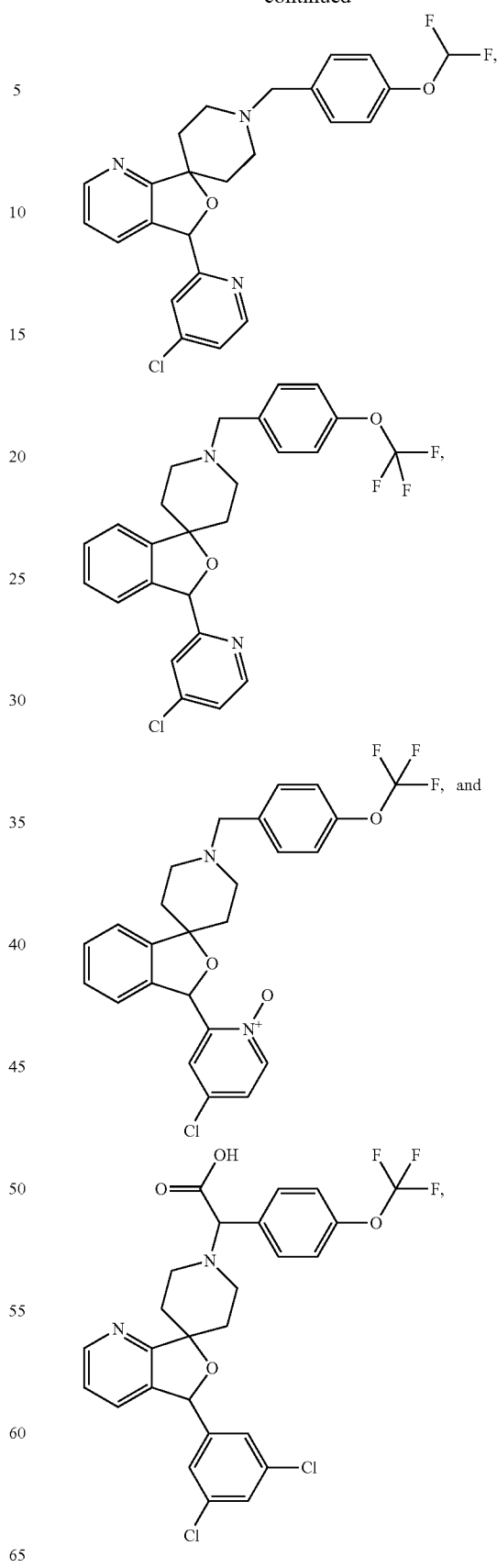
-continued
and pharmaceutically acceptable salts thereof.

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. When no number of carbon atoms is specified, $C_{1-6}$ is intended.

"Alkenyl" means carbon chains up to 10 carbons, unless otherwise specified, which contain at least one carbon-carbon double bond, and which may be linear or branched or combinations thereof. Examples of alkenyl include vinyl, allyl, isopropenyl, pentenyl, hexenyl, heptenyl, 1-propenyl, 1-butenyl, 2-butenyl, 2-methyl-2-butenyl, and the like.

"Alkynyl" means carbon chains up to 10 carbons, if not otherwise specified, which contain at least one carbon-carbon triple bond, and which may be linear or branched or combinations thereof. Examples of alkynyl include ethynyl, propynyl, butynyl, pentynyl, 3-methyl-1-pentynyl, 2-heptynyl and the like.

The term "alkoxy" refers to straight or branched chain alkoxides of the number of carbon atoms specified (e.g., $C_{1-6}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-6}$ alkylthio), or any number within this range [i.e., methylthio (MeS—), ethylthio, isopropylthio, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl ($MeSO_2$—), ethylsulfonyl, isopropylsulfonyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Cycloalkyl" means mono- or bicyclic or bridged saturated carbocyclic rings, each having from 3 to 14 carbon atoms. Examples of cycloalkyl include cyclopropyl, cyclobutyl, cyclopentyl, cyclohexyl, cycloheptyl, cyclobutyl, and decahydronaphthyl, and the like. In one embodiment of the present invention, cycloalkyl is selected from: cyclopropyl, cyclobutyl, cyclopentyl, cyclohexyl and cycloheptyl. In another embodiment of the present invention, cycloalkyl is selected from: cyclopropyl, cyclobutyl, and cyclohexyl.

"Cycloalkenyl" means nonaromatic, mono- or bicyclic or bridged carbocyclic rings, each having from 3 to 14 carbon atoms and containing at least one double bond. Examples of cycloalkyl include cyclopropenyl, cyclobutenyl, cyclopentenyl, cyclohexenyl, cycloheptenyl, cyclooxtenyl, decahydronaphthyl, bicyclo[2.2.1]hept-5-en-2-yl, and the like.

"Cycloheteroalkyl" means nonaromatic, mono- or bicyclic or bridged saturated carbocyclic rings, each having from 2 to 14 carbon atoms and containing 1, 2, 3, 4 or 5 heteroatoms selected from N, NH, O and S. Examples of cycloheteroalkyl include tetrahydrofuranyl, azetidinyl, perhydroazepinyl, dihydrofuranyl, dioxanyl, oxanyl, morpholinyl, 1,4-dithianyl, piperazinyl, piperidinyl, 1,3-dioxolanyl, imidazolidinyl, imidazolinyl, pyrrolinyl, pyrrolidinyl, pyranyl, tetrahydropyranyl, dihydropyranyl, oxathiolanyl, dithiolanyl, 1,3-dithianyl, oxathianyl, thiomorpholinyl, dioxidoisothiazolidinyl, azacycloheptyl, diazobicyclo[3.2.1]-octane, and hexahydroindazolyl. The cycloheteroalkyl ring may be substituted on the ring carbons and/or the ring nitrogens. In one embodiment of the present invention, cycloheteroalkyl is selected from: morpholine, pyrrolidine, piperidine, piperazine, and tetrahydropyridine. In another embodiment of the present invention, cycloheteroalkyl is selected from: pyrrolidine, and azabicyclo[2.2.1]heptane.

"Cycloheteroalkenyl" means nonaromatic mono- or bicyclic or bridged rings each having from 2 to 14 carbon atoms containing at least one double bond and containing 1, 2, 3, 4 or 5 heteroatoms selected from N, NH, O and S. Examples of cycloheteroalkenyl include 1,2,4-oxadiazol-5-one, 1,2,4-thiadiazol-5-one, 1,2,4-triazol-3-one, and 1,2,3,6-tetrahydropyridine, dihydro-1,3,4-oxadiazole, and [1,6]-dihydropyridine and the like. In one embodiment of the present invention, cycloheteroalkenyl is dihydro-1,3,4-oxadiazole. In another embodiment of the present invention, cycloheteroalkenyl is [1,6]-dihydropyridine. In another embodiment of the present invention, cycloheteroalkenyl is tetrahydropyridine.

"Aryl" means a monocyclic, bicyclic or tricyclic ring system containing 5-14 carbon atoms, wherein at least one of the rings is aromatic. Aryl thus includes ring systems in which an aromatic ring is fused to a non-aromatic ring, such as a cycloalkyl or cycloalkenyl ring. Examples of aryl include phenyl, naphthalene, biphenyl, indane and 5,6,7,8-tetrahydronaphthalene, and the like. In one embodiment of the present invention, aryl is phenyl, naphthalene, biphenyl, indane, and 5,6,7,8-tetrahydronaphthalene. In another embodiment of the present invention, aryl is phenyl, naphthalene, indane and 5,6,7,8-tetrahydronaphthalene. In one class of this embodiment, aryl is phenyl and naphthalene. In another class of this embodiment, aryl is phenyl. In another class of this embodiment, aryl is naphthalene.

"Heteroaryl" means a monocyclic, bicyclic or tricyclic ring system containing 5-14 carbon atoms and containing 1, 2, 3, 4 or 5 heteroatoms selected from N, NH, O and S wherein at least one of the heteroatom containing rings is aromatic. Heteroaryls thus includes heteroaryls fused to other kinds of rings, such as aryls, cycloalkyls and heterocycles that are not aromatic. Heteroaryl includes ring systems in which an aromatic heteroatom containing ring is fused to a non-aromatic ring, such as a cycloalkyl, cycloalkenyl, cycloheteroalkyl or cycloheteroalkenyl ring, and also includes ring systems in which an aryl ring is fused to a non-aromatic heteroatom containing ring, such as a cycloheteroalkyl or cycloheteroalkenyl ring. Examples of heteroaryls include: pyrazole, pyridine, pyrazine, pyrrole, pyrimidine, pyridazine, benzoimidazole, quinoline, isothiazole, isoquinoline, indole, indazole, carbazole, benzotriazole, benzofuran, benzothiazole, benzothiophene, benzoisooxazole, oxazole, oxadiazole, furan, benzoxazole, isoxazole, indoline, isoindoline, tetrazole, imidazole, oxadiazole (in particular, 1,3,4-oxadiazol-2-yl and 1,2,4-oxadiazol-3-yl), thiazole, thiophene, thiadiazole, triazole, triazine, tetrazole, thiene, benzothiazole, bernzopyrazole, benzothiadiazole, dihydrobenzofuran, indazole, isoindole, dihydrobenzothiene, indolizine, cinnoline, phthalazine, quinazoline, naphthyridine, carbazole, quinoxaline, purine, isobenzylfuran, benzothiene, isoquinoline, dibenzofuran, isothiazole, imidazopyridine, benzodioxole, dihydropyridine, dihydropyrrolopyridine, dihydrobenzooxazine, benzodioxole, benzodioxine, pyrrolopyridine, triazolopyridine, dihydropyridooxazine, dihydrobenzoxazine, dihydroindole, dihydroisoindole, dihydrobenzoimidazole, dihydroquinoline, tetrahydroisoquinoline, tetrahydrocyclopentaindole, tetrahydroquinoxaline, and tetrahydropyridine. For heterocycloalkyl and heteroaryl groups, rings and ring systems containing from 3-15 atoms are included, forming 1-3 rings. In one embodiment of the present invention, heteroaryl is selected from: pyridine, pyrazole, and oxazole. In another embodiment of the present invention, heteroaryl is selected from: pyridine, pyridine N-oxide; and pyridine N-hydroxide. In another embodiment of the present invention, heteroaryl is selected from: pyridine, pyrazine, pyridazine, pyrimidine, thiophene, benzodioxole, naphthalene, benzofuran, oxazole, thiazole, triazole, benzisoxazole, and imidazopyrimidine.

"Halogen" includes fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$). In one embodiment of the present invention, halogen is selected from fluorine, chlorine, and bromine.

"Oxo" means the functional group "=O" which is an oxygen atom connected to the molecule via a double bond, such as, for example, (1) "C=(O)", that is a carbonyl group; (2) "S=(O)", that is, a sulfoxide group; and (3) "N=(O)", that is, an N-oxide group, such as pyridyl-N-oxide.

In choosing compounds of the present invention, one of ordinary skill in the art will recognize that the various substituents, i.e. $R^1$, $R^2$, etc., are to be chosen in conformity with well-known principles of chemical structure connectivity and stability. When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the functional group adjacent to the point of attachment is described first, with our without a bond "~", followed by the terminal portion of the designated side chain. For example, a $—C_{1-5}$ alkylcarbonylamino $C_{1-6}$ alkyl substituent is equivalent to:

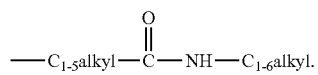

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The terms "compounds of structural formula I" and "formula I" include the compounds of structural formulas I, Ia, Ib, Ic, Id, and Ie, and pharmaceutically acceptable salts thereof.

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration. Alternatively, any stereoisomer of a compound of the general structural formula I may be obtained by stereospecific synthesis using optically pure starting materials or reagents of known absolute configuration.

Compounds of the Formula I may be separated into diastereoisomeric pairs of enantiomers by, for example, fractional crystallization from a suitable solvent, for example MeOH or ethyl acetate or a mixture thereof. The pair of enantiomers thus obtained may be separated into individual stereoisomers by conventional means, for example by the use of an optically active amine as a resolving agent or on a chiral HPLC column. Alternatively, any enantiomer of a compound of the general Formula I may be obtained by stereospecific synthesis using optically pure starting materials or reagents of known configuration.

If desired, racemic mixtures of the compounds may be separated so that the individual enantiomers are isolated. Racemic mixtures can be separated into their individual enantiomers by any of a number of conventional methods, which include chiral chromatography, derivatization with a chiral auxiliary followed by separation by chromatography or crystallization, and fractional crystallization of diastereomeric salts. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Some of the compounds described herein contain olefinic double bonds, and unless specified otherwise, are meant to include both B and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

In the compounds of structural formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations. The compounds of the present invention may be administered in the form of a pharmaceutically acceptable salt.

The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetyl, pivaloyl, benzoyl, and aminoacyl, can be employed. Included are those esters and acyl groups known in the art for modifying the solubility or hydrolysis characteristics for use as sustained-release or prodrug formulations.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The compounds of formula I are effective as inhibitors of prolylcarboxypeptidase (PRCP). The compounds of formula I are therefore useful for the treatment, control and/or prevention of diseases, disorders or conditions responsive to the inhibition of the prolylcarboxypeptidase (PRCP) enzyme, including but not limited to: abnormal metabolism, obesity, diabetes, metabolic syndrome, obesity related disorders, diabetes related disorders, hypertension, dyslipidemia, stroke, gallbladder disease, cardiovascular disease, osteoarthritis, rheumatoid arthritis, hypercholesterolemia, stable angina, unstable angina, artherosclerosis, sleep apnea, respiratory problems, cancer, and stroke.

One aspect of the present invention provides a method for the treatment or prevention of disorders, diseases or conditions responsive to the inhibition of prolylcarboxypeptidase in a subject in need thereof which comprises administering to the subject a therapeutically or prophylactically effective amount of a compound of formula I, or a pharmaceutically acceptable salt thereof.

Another aspect of the present invention provides a method for the treatment or prevention of obesity, diabetes, an obesity related disorder or a diabetes related disorder in a subject in need thereof which comprises administering to said subject a therapeutically or prophylactically effective amount of a prolylcarboxypeptidase inhibitor of formula I. Another aspect of the present invention provides a method for the treatment or prevention of obesity in a subject in need thereof which comprises administering to the subject a therapeutically or prophylactically effective amount of a compound of formula I, or a pharmaceutically acceptable salt thereof. Another aspect of the present invention provides a method for reducing food intake in a subject in need thereof which comprises administering to the subject a therapeutically or prophylactically effective amount of a compound of formula I, or a pharmaceutically acceptable salt thereof. Another aspect of the present invention provides a method for reducing body fat mass in a subject in need thereof which comprises administering to the subject a therapeutically or prophylactically effective amount of a compound of formula I, or a pharmaceutically acceptable salt thereof. Another aspect of the present invention provides a method for losing weight in a subject in need thereof which comprises administering to the subject a therapeutically or prophylactically effective amount of a compound of formula I, or a pharmaceutically acceptable salt thereof.

Another aspect of the present invention provides a method for the treatment or prevention of an obesity-related disorder selected from the group consisting of: overeating, binge eating, hypertension, elevated plasma insulin concentrations, insulin resistance, hyperlipidemia, endometrial cancer, breast cancer, prostate cancer, colon cancer, kidney cancer, osteoarthritis, obstructive sleep apnea, heart disease, abnormal heart rhythms and arrythmias, myocardial infarction, congestive heart failure, coronary heart disease, sudden death, stroke, polycystic ovary disease, craniopharyngioma, metabolic syndrome, insulin resistance syndrome, sexual and reproductive dysfunction, infertility, hypogonadism, hirsutism, obesity-related gastro-esophageal reflux, Pickwickian syndrome, inflammation, systemic inflammation of the vasculature, arteriosclerosis, hypercholesterolemia, hyperuricaemia, lower back pain, gallbladder disease, gout, constipation, irritable bowel syndrome, inflammatory bowel syndrome, cardiac hypertrophy, left ventricular hypertrophy, in a subject in need thereof which comprises administering to the subject a therapeutically or prophylactically effective amount of a compound of formula I, or a pharmaceutically acceptable salt thereof.

Another aspect of the present invention provides a method for the treatment or, prevention of diabetes, in a subject in need thereof which comprises administering to the subject a therapeutically or prophylactically effective amount of a compound of formula I, or a pharmaceutically acceptable salt thereof.

Another aspect of the present invention provides a method for the treatment or prevention of a diabetes related disorder in a subject in need thereof which comprises administering to the subject a therapeutically or prophylactically effective amount of a compound of formula I, or a pharmaceutically acceptable salt thereof.

Another aspect of the present invention provides a method for the treatment or prevention of a diabetes related disorder selected from the group consisting of: hyperglycemia, low glucose tolerance, insulin resistance, obesity, lipid disorders, dyslipidemia, hyperlipidemia, hypertriglyceridemia, hypercholesterolemia, low HDL levels, high LDL levels, atherosclerosis and its sequelae, vascular restenosis, irritable bowel syndrome, inflammatory bowel disease, including Crohn's disease and ulcerative colitis, other inflammatory conditions, pancreatitis, abdominal obesity, neurodegenerative disease, retinopathy, nephropathy, neuropathy, Syndrome X, and ovarian hyperandrogenism (polycystic ovarian syndrome), in a subject in need thereof which comprises administering to the subject a therapeutically or prophylactically effective amount of a compound of formula I, or a pharmaceutically acceptable salt thereof.

The present invention also relates to methods for treating or preventing obesity by administering a compound of formula I in combination with a therapeutically or prophylactically effective amount of another agent known to be useful to treat or prevent the condition. The present invention also relates to methods for treating or preventing diabetes by administering a compound of formula I in combination with a therapeutically or prophylactically effective amount of another agent known to be useful to treat or prevent the condition. The present invention also relates to methods for treating or preventing obesity related disorders by administering a compound of formula I in combination with a therapeutically or prophylactically effective amount of another agent known to be useful to treat or prevent the condition.

Yet another aspect of the present invention relates to the use of a therapeutically effective amount of a compound of formula I, or a pharmaceutically acceptable salt or ester thereof, and a therapeutically effective amount of at least one agent selected from the group consisting of: simvastatin, mevastatin, ezetimibe, atorvastatin, sitagliptin, metformin, sibutramine, orlistat, Qnexa, topiramate, phentermine, losartan, losartan with hydrochlorothiazide, or rimonabant, or a pharmaceutically acceptable salt or ester or prodrug thereof, for the manufacture of a medicament useful for the treatment, control, or prevention of obesity, diabetes, a diabetes related disorder, or an obesity-related disorder in a subject in need of such treatment.

Another aspect of the present invention provides a pharmaceutical composition comprising a compound of formula I, and a pharmaceutically acceptable carrier.

Yet another aspect of the present invention relates to the use of a compound of formula I for the manufacture of a medicament useful for the treatment or prevention, or suppression of a disease mediated by prolylcarboxypeptidase (PRCP) in a subject in need thereof.

Yet another aspect of the present invention relates to the use of a compound of formula I for the manufacture of a medicament useful for the treatment or prevention, or suppression of a disease mediated by prolylcarboxypeptidase (PRCP), wherein the disease is selected from the group consisting of obesity, diabetes, an obesity-related disorder and a diabetes related disorder in a subject in need thereof.

Yet another aspect of the present invention relates to the use of a therapeutically effective amount of a compound of formula I, or a pharmaceutically acceptable salt thereof, and a therapeutically effective amount of an agent selected from the group consisting of an insulin sensitizer, an insulin mimetic, a sulfonylurea, an α-glucosidase inhibitor, a dipeptidyl peptidase 4 (DPP-4) inhibitor, a glucagons like peptide 1 (GLP-1) agonist, a HMG-CoA reductase inhibitor, a serotonergic agent, β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a melanocortin 4 receptor agonist, a bombesin receptor subtype δ agonist, a ghrelin receptor antagonist, PYY, $PYY_{3-36}$, and a NK-1 antagonist, or a pharmaceutically acceptable salt thereof, for the manufacture of a medicament useful for the treatment, control, or prevention of obesity, diabetes or an obesity-related disorder in a subject in need of such treatment. Yet another aspect of the present invention relates to the use of a therapeutically effective amount of a compound of formula I, and pharmaceutically acceptable salts and esters thereof, and a therapeutically effective amount of an agent selected from the group consisting of an insulin sensitizer, an insulin mimetic, a sulfonylurea, an α-glucosidase inhibitor, a dipeptydyl peptidase 4 inhibitor, a glucagon-like peptide 1 agonist, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a melanocortin 4 receptor agonist, a bombesin receptor subtype δ agonist, a ghrelin receptor antagonist, PYY, $PYY_{3-36}$, and a NK-1 antagonist, or a pharmaceutically acceptable salt thereof, for the manufacture of a medicament for treatment or prevention of obesity, diabetes, an obesity related disorder or a diabetes related disorder which comprises an effective amount of a the compound of formula I, and an effective amount of the agent, together or separately. Yet another aspect of the present invention relates to a product containing a therapeutically effective amount of a compound of formula I, or a pharmaceutically acceptable salt thereof; and a therapeutically effective amount of an agent selected from the group consisting of an insulin sensitizer, an insulin mimetic, a sulfonylurea, an α-glucosidase inhibitor, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanocortin 4 receptor agonist, a melanin-concentrating hormone receptor antagonist, a bombesin receptor subtype δ agonist, a ghrelin receptor antagonist, PYY, $PYY_{3-36}$, and a NK-1 antagonist, or a pharmaceutically acceptable salt thereof, as a combined preparation for simultaneous, separate or sequential use in obesity, diabetes, an obesity-related disorder or a diabetes related disorder.

The compounds of formula I can be provided in kit. Such a kit typically contains an active compound in dosage forms for administration. A dosage form contains a sufficient amount of active compound such that a beneficial effect can be obtained when administered to a patient during regular intervals, such as 1, 2, 3, 4, 5 or 6 times a day, during the course of 1 or more days. Preferably, a kit contains instructions indicating the use of the dosage form for weight reduction (e.g., to treat obesity) and the amount of dosage form to be taken over a specified time period.

Compounds of formula I are inhibitors of prolylcarboxypeptidase (PRCP) and as such are useful in the treatment, control or prevention of diseases, disorders or conditions responsive to the modulation of prolylcarboxypeptidase (PRCP). Such diseases, disorders or conditions include, but are not limited to, abnormal metabolism, obesity, diabetes, metabolic syndrome, obesity related disorders, diabetes related disorders, hypertension, dyslipidemia, stroke, gallbladder disease, cardiovascular disease, osteoarthritis, rheumatoid arthritis, hypercholesterolemia, stable angina, unstable angina, artherosclerosis, sleep apnea, respiratory problems, cancer, and stroke. Such diseases, conditions and disorders also include non-obese overweight conditions and normal weight conditions where weight control or management is desired in order to prevent an obese or overweight condition from developing, or to maintain a healthy weight.

The compounds of formula I, and compositions thereof, are useful for the treatment or prevention of disorders associated with excessive food intake, such as obesity and obesity-related disorders. The obesity herein may be due to any cause, whether genetic or environmental.

The obesity-related disorders herein are associated with, caused by, or result from obesity. Examples of obesity-related disorders include overeating, binge eating, bulimia nervosa, hypertension, type 2 diabetes, elevated plasma insulin concentrations, hyperinsulinemia, insulin resistance, glucose intolerance, dyslipidemia, hyperlipidemia, endometrial cancer, breast cancer, prostate cancer, kidney cancer, colon cancer, osteoarthritis, obstructive sleep apnea, cholelithiasis, cholecystitis, gallstones, gout, gallbladder disease, abnormal heart rhythms and arrythmias, myocardial infarction, congestive heart failure, coronary heart disease, angina pectoris, sudden death, stroke, metabolic syndrome, psychological disorders (depression, eating disorders, distorted bodyweight, and low self esteem), and other pathological conditions showing reduced metabolic activity or a decrease in resting energy expenditure as a percentage of total fat-free mass, e.g, children with acute lymphoblastic leukemia. Further examples of obesity-related disorders are sexual and reproductive dysfunction, such as polycystic ovary disease, infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. Additionally, the present compounds are useful in the treatment of any condition in which it is desirable to lose weight or to reduce food intake. Additionally, the present compounds are useful in the treatment of any condition in which it is desirable to enhance cognition and memory, such as Alzheimer's Disease. The compositions of the present invention are also useful for reducing the risk of secondary outcomes of obesity, such as reducing the risk of left ventricular hypertrophy. Therefore, the present invention provides methods of treatment or prevention of such diseases, conditions and/or disorders modulated by prolylcarboxypeptidase (PRCP) in an animal which comprises administering to the animal in need of such treatment a compound of formula I, in particular a therapeutically or prophylactically effective amount thereof.

The term "inhibitor" as used herein means a composition of matter which when administered to a mammal, such as a human, inhibits the biological activity attributable to the level or presence of an endogenous compound in the mammal. Inhibition of PrCP includes, but is not limited to, inhibiting the biological activity of the PrCP molecule or enzyme.

The term "subject" means a mammal. One embodiment of the term "mammal" is a "human," said human being either male or female. The instant compounds are also useful for treating or preventing obesity and obesity related disorders in cats and dogs. As such, the term "mammal" includes companion animals such as cats and dogs. The term "mammal in need thereof" refers to a mammal who is in need of treatment or prophylaxis as determined by a researcher, veterinarian, medical doctor or other clinician.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The term "metabolic syndrome", also known as syndrome X, is defined in the Third Report of the National Cholesterol Education Program. Expert Panel on Detection, Evaluation and Treatment of High Blood Cholesterol in Adults (ATP-III). E. S. Ford et al., JAMA, vol. 287 (3), Jan. 16, 2002, pp 356-359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-III.

The term "diabetes," as used herein, includes both insulin-dependent diabetes mellitus (i.e., IDDM, also known as type I diabetes) and non-insulin-dependent diabetes mellitus (i.e., NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compositions of the present invention are useful for treating both Type I and Type II diabetes. The compositions are especially effective for treating Type II diabetes. The compounds or combinations of the present invention are also useful for treating and/or preventing gestational diabetes mellitus.

Diabetes is characterized by a fasting plasma glucose level of greater than or equal to 126 mg/dl. A diabetic subject has a fasting plasma glucose level of greater than or equal to 126 mg/dl. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of ≥140 mg/dl and <200 mg/dl); or insulin resistance, resulting in an increased risk of developing diabetes.

"Diabetes related disorders" are diseases, disorders and conditions that are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component. In Syndrome X, also known as Metabolic Syndrome, obesity is thought to promote insulin resistance, diabetes, dyslipidemia, hypertension, and increased cardiovascular risk. Therefore, inhibitors of prolylcarboxypeptidase (FRCP) may also be useful to treat hypertension associated with this condition.

Treatment of diabetes mellitus refers to the administration of a compound or combination of the present invention to treat diabetes. One outcome of treatment may be decreasing the glucose level in a subject with elevated glucose levels. Another outcome of treatment may be improving glycemic control. Another outcome of treatment may be decreasing insulin levels in a subject with elevated insulin levels. Another outcome of the treatment of diabetes is to reduce an increased plasma glucose concentration. Another outcome of the treatment of diabetes is to reduce an increased insulin concentration. Still another outcome of the treatment of diabetes is to reduce an increased blood triglyceride concentration. Still another outcome of the treatment of diabetes is to increase insulin sensitivity. Still another outcome of the treatment of diabetes may be enhancing glucose tolerance in a subject with glucose intolerance. Still another outcome of the treatment of diabetes is to reduce insulin resistance. Another outcome of the treatment of diabetes is to lower plasma insulin levels. Still another outcome of treatment of diabetes is an improvement in glycemic control, particularly in type 2 diabetes.

Prevention of diabetes mellitus, in particular diabetes associated with obesity, refers to the administration of a compound or combination of the present invention to prevent or treat the onset of diabetes in a subject in need thereof. A subject in need of preventing diabetes in a pre-diabetic subject.

"Obesity" is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes, non-insulin dependent diabetes mellitus—type II (2), impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders refers to the administration of the compounds or combinations of the present invention to reduce or maintain the body weight of an obese subject. One outcome of treatment may be reducing the body weight of an obese subject relative to that subject's body weight immediately before the administration of the compounds or combinations of the present invention, Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and in weight reduction in subjects in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds or combinations of the present invention to reduce or maintain the body weight of a subject at risk of obesity. One outcome of prevention may be reducing the body weight of a subject at risk of obesity relative to that subject's body weight immediately before the administration of the compounds or combinations of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovary disease, cardiovascular diseases, osteoarthritis, hypertension, dyslipidemia, insulin resistance, hypercholesterolemia, hypertriglyceridemia, and cholelithiasis.

The terms "administration of" and or "administering" a compound should be understood to mean providing a compound of the invention or a prodrug of a compound of the invention to a subject in need of treatment. The administration of the compounds of the present invention in order to practice the present methods of therapy is carried out by administering a therapeutically effective amount of the compound to a subject in need of such treatment or prophylaxis. The need for a prophylactic administration according to the methods of the present invention is determined via the use of well known risk factors.

The term "therapeutically effective amount" as used herein means the amount of the active compound that will elicit the biological or medical response in a tissue, system, subject, mammal, or human that is being sought by the researcher, veterinarian, medical doctor or other clinician, which includes alleviation of the symptoms of the disorder being treated. The novel methods of treatment of this invention are for disorders known to those skilled in the art. The term "prophylactically effective amount" as used herein means the amount of the active compound that will elicit the biological or medical response in a tissue, system, subject, mammal, or human that is being sought by the researcher, veterinarian, medical doctor or other clinician, to prevent the onset of the disorder in subjects as risk for obesity or the disorder. The therapeutically or prophylactically effective amount, or dosage, of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgement.

Administration and Dose Ranges

Any suitable route of administration may be employed for providing a subject or mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally or topically.

The effective dosage of active ingredient employed may vary depending on the particular compound employed, the mode of administration, the condition being treated and the severity of the condition being treated. Such dosage may be ascertained readily by a person skilled in the art.

Generally satisfactory results are obtained when the compounds of formula I are administered at a daily dosage of from about 0.001 milligram to about 50 milligrams per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

In the case where an oral composition is employed, a suitable dosage range is, e.g. from about 0.01 mg to about 1500 mg of a compound of Formula I per day, preferably from about 0.1 mg to about 600 mg per day, more preferably from about 0.1 mg to about 100 mg per day. For oral administration, the compositions are preferably provided in the form of tablets containing from 0.01 to 1,000 mg, preferably 0.01, 0.05, 0.1, 0.5, 1, 2.5, 5, 10, 15, 20, 25, 30, 40, 50, 100, 250, 500, 600, 750, 1000, 1250 or 1500 milligrams of the active ingredient for the symptomatic adjustment of the dosage to the patient to be treated.

For use where a composition for intranasal administration is employed, intranasal formulations for intranasal administration comprising 0.001-10% by weight solutions or suspensions of the compounds of formula I in an acceptable intranasal formulation may be used.

For use where a composition for intravenous administration is employed, a suitable dosage range is from about 0.001 mg to about 50 mg, preferably from 0.01 mg to about 50 mg, more preferably 0.1 mg to 10 mg, of a compound of formula I per kg of body weight per day. This dosage regimen may be adjusted to provide the optimal therapeutic response. It may be necessary to use dosages outside these limits in some cases.

For the treatment of diseases of the eye, ophthalmic preparations for ocular administration comprising 0.001-1% by weight solutions or suspensions of the compounds of formula I in an acceptable ophthalmic formulation may be used.

The magnitude of prophylactic or therapeutic dosage of the compounds of the present invention will, of course, vary depending on the particular compound employed, the mode of administration, the condition being treated and the severity of the condition being treated. It will also vary according to the age, weight and response of the individual patient. Such dosage may be ascertained readily by a person skilled in the art.

Combination Therapy

Compounds of Formula I may be used in combination with other drugs that may also be useful in the treatment or amelioration of the diseases or conditions for which compounds of Formula I are useful. Such other drugs may be administered, by a route and in an amount commonly used therefor, contemporaneously or sequentially with a compound of Formula I. In the treatment of patients who have Type 2 diabetes, insulin resistance, obesity, metabolic syndrome, and co-morbidities that accompany these diseases, more than one drug is commonly administered. The compounds of this invention may generally be administered to a patient who is already taking one or more other drugs for these conditions. Often the compounds will be administered to a patient who is already being treated with one or more antidiabetic compound, such as metformin, sulfonylureas, and/or PPAR agonists, when the patient's glycemic levels are not adequately responding to treatment.

When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) PPAR gamma agonists and partial agonists, including both glitazones and non-glitazones (e.g. troglitazone, pioglitazone, englitazone, MCC-555, rosiglitazone, balaglitazone, netoglitazone, T-131, LY-300512, LY-818, and compounds disclosed in WO02/08188, WO2004/020408, and WO2004/020409.

(b) biguanides, such as metformin and phenformin;

(c) protein tyrosine phosphatase-1B (PTP-1B) inhibitors;

(d) dipeptidyl peptidase-1V (DPP-4) inhibitors, such as sitagliptin, saxagliptin, vildagliptin, and alogliptin;

(e) insulin or insulin mimetics;

(f) sulfonylureas such as tolbutamide, glimepiride, glipizide, and related materials;

(g) α-glucosidase inhibitors (such as acarbose);

(h) agents which improve a patient's lipid profile, such as (i) HMG-CoA reductase inhibitors (lovastatin, simvastatin, rosuvastatin, pravastatin, fluvastatin, atorvastatin, rivastatin, itavastatin, ZD-4522 and other statins), (ii) bile acid sequestrants (cholestyramine, colestipol, and dialkylaminoalkyl derivatives of a cross-linked dextran), (iii) niacin receptor agonists, nicotinyl alcohol, nicotinic acid, or a salt thereof, (iv) PPARα agonists, such as fenofibric acid derivatives (gemfibrozil, clofibrate, fenofibrate and bezafibrate), (v) cholesterol absorption inhibitors, such as ezetimibe, (vi) acyl CoA:cholesterol acyltransferase (ACAT) inhibitors, such as avasimibe, (vii) CETP inhibitors, such as torcetrapib, and (viii) phenolic antioxidants, such as probucol;

(i) PPARα/γ dual agonists, such as muraglitazar, tesaglitazar, farglitazar, and JT-501;

(j) PPARδ agonists, such as those disclosed in WO97/28149;

(k) anti-obesity compounds, such as fenfluramine, dexfenfluramine, phentiramine, subitramine, orlistat, neuropeptide Y Y5 inhibitors, MC4R agonists, cannabinoid receptor 1 (CB-1) antagonists/inverse agonists (e.g., rimonabant and taranabant), and $β_3$ adrenergic receptor agonists;

(l) ileal bile acid transporter inhibitors;

(m) agents intended for use in inflammatory conditions, such as aspirin, non-steroidal anti-inflammatory drugs, glucocorticoids, azulfidine, and cyclooxygenase-2 (Cox-2) selective inhibitors;

(n) glucagon receptor antagonists;

(o) GLP-1;

(p) GIP-1;

(q) GLP-1 analogs and derivatives, such as exendins, (e.g., exenatide and liruglatide);

(r) 11β-hydroxysteroid dehydrogenase-1 (HSD-1) inhibitors;

(s) inhibitors of cholesteryl ester transfer protein (CETP), such as torcetrapib;

(t) SSTR3 antagonists;

(u) other SSTR5 antagonists;

(v) acetyl CoA carboxylase-1 and/or -2 inhibitors;

(w) AMPK activators;

(x) agonists of GPR-119;

(y) glucokinase agonists; and (z) FGF-21 agonists.

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, other PPAR agonists, PTP-1B inhibitors, DPP-4 inhibitors, and cannabinoid receptor 1 (CB1) inverse agonists/antagonists.

Antiobesity compounds that can be combined with compounds described herein include fenfluramine, dexfenfluramine, phentermine, sibutramine, orlistat, neuropeptide $Y_1$ or $Y_5$ antagonists, cannabinoid CB1 receptor antagonists or inverse agonists, melanocortin receptor agonists, in particular, melanocortin-4 receptor agonists, ghrelin antagonists, bombesin receptor agonists, and melanin-concentrating hormone (MCH) receptor antagonists. For a review of anti-obesity compounds that can be combined with compounds described herein, see S. Chaki et al., "Recent advances in feeding suppressing agents: potential therapeutic strategy for the treatment of obesity," *Expert Opin. Ther. Patents*, 11: 1677-1692 (2001); D. Spanswick and K. Lee, "Emerging antiobesity drugs," *Expert Opin. Emerging Drugs*, 8: 217-237 (2003); and J. A. Fernandez-Lopez, et al., "Pharmacological Approaches for the Treatment of Obesity," *Drugs*, 62: 915-944 (2002).

Neuropeptide Y5 antagonists that can be combined with compounds described herein include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

Cannabinoid CB1 receptor antagonists that can be combined with compounds described herein include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. No. 5,532,237; U.S. Pat. No. 5,292,736; PCT Publication WO 03/086288; PCT Publication WO 03/087037; PCT Publication WO 04/048317; PCT Publication WO 03/007887; PCT Publication WO 03/063781; PCT Publication WO 03/075660; PCT Publication WO 03/077847; PCT Publication WO 03/082190; PCT Publication WO 03/082191; PCT Publication WO 03/087037; PCT Publication WO 03/086288; PCT Publication WO 04/012671; PCT Publication WO 04/029204; PCT Publication WO 04/040040; PCT Publication WO 01/64632; PCT Publication WO 01/64633; and PCT Publication WO 01/64634.

Suitable melanocortin-4 receptor (MC4R) agonists include, but are not limited to, those disclosed in U.S. Pat. No. 6,294,534, U.S. Pat. Nos. 6,350,760, 6,376,509, 6,410,548, 6,458,790, U.S. Pat. No. 6,472,398, U.S. Pat. No. 5,837,521, U.S. Pat. No. 6,699,873, which are hereby incorporated by reference in their entirety; in US Patent Application Publication Nos. US 2002/0004512, US2002/0019523, US2002/0137664, US2003/0236262, US2003/0225060, US2003/0092732, US2003/109556, US 2002/0177151, US 2002/187932, US 2003/0113263, which are hereby incorporated by reference in their entirety; and in WO 99/64002, WO 00/74679, WO 02/15909, WO 01/70708, WO 01/70337, WO 01/91752, WO 02/068387, WO 02/068388, WO 02/067869, WO 03/007949, WO 2004/024720, WO 2004/089307, WO 2004/078716, WO 2004/078717, WO 2004/037797, WO 01/58891, WO 02/070511, WO 02/079146, WO 03/009847, WO 03/057671, WO 03/068738, WO 03/092690, WO 02/059095, WO 02/059107, WO 02/059108, WO 02/059117, WO 02/085925, WO 03/004480, WO 03/009850, WO 03/013571, WO 03/031410, WO 03/053927, WO 03/061660, WO 03/066597, WO 03/094918, WO 03/099818, WO 04/037797, WO 04/048345, WO 02/018327, WO 02/080896, WO 02/081443, WO 03/066587, WO 03/066597, WO 03/099818, WO 02/062766, WO 03/000663, WO 03/000666, WO 03/003977, WO 03/040107, WO 03/040117, WO 03/040118, WO 03/013509, WO 03/057671, WO 02/079753, WO 02/092566, WO 03/-093234, WO 03/095474, and WO 03/104761.

Specific compounds of use in combination with a compound of the present invention include: simvastatin, mevastatin, ezetimibe, atorvastatin, sitagliptin, metformin, sibutramine, orlistat, Qnexa, topiramate, naltrexone, bupriopion, phentermine, and losartan, losartan with hydrochlorothiazide.

Examples of other anti-obesity agents that can be employed in combination with a compound of formula I, II, III or IV are disclosed in "Patent focus on new anti-obesity agents," *Exp. Opin. Ther. Patents*, 10: 819-831 (2000); "Novel anti-obesity drugs," *Exp. Opin. Invest. Drugs*, 9: 1317-1326 (2000); and "Recent advances in feeding suppressing agents: potential therapeutic strategy for the treatment of obesity, *Exp. Opin. Ther. Patents*, 11: 1677-1692 (2001). The role of neuropeptide Y in obesity is discussed in *Exp. Opin. Invest. Drugs*, 9: 1327-1346 (2000). Cannabinoid receptor ligands are discussed in *Exp. Opin. Invest. Drugs*, 9: 1553-1571 (2000).

The instant invention also includes administration of a single pharmaceutical dosage formulation which contains both a compound of formula I in combination with a second active ingredient, as well as administration of each active agent in its own separate pharmaceutical dosage formulation. Where separate dosage formulations are used, the individual components of the composition can be administered at essentially the same time, i.e., concurrently, or at separately staggered times, i.e. sequentially prior to or subsequent to the administration of the other component of the composition. The instant invention is therefore to be understood to include all such regimes of simultaneous or alternating treatment, and the terms "administration" and "administering" are to be interpreted accordingly. Administration in these various ways are suitable for the present compositions as long as the beneficial pharmaceutical effect of the combination of the compound of formula I and the second active ingredient is realized by the patient at substantially the same time. Such beneficial effect is preferably achieved when the target blood level concentrations of each active ingredient are maintained at substantially the same time. It is preferred that the combination of the compound of formula I and the second active ingredient be co-administered concurrently on a once-a-day dosing schedule; however, varying dosing schedules, such as the compound of formula I once a day and the second active ingredient once, twice or more times per day or the compound of formula I three times a day and the second active ingredient once, twice or more times per day, is also encompassed herein. A single oral dosage formulation comprised of both a compound of formula I and a second active ingredient is preferred. A single dosage formulation will provide convenience for the patient, which is an important consideration especially for patients with diabetes or obese patients who may be in need of multiple medications.

The compounds in the combinations of the present invention may be administered separately, therefore the invention also relates to combining separate pharmaceutical compositions into a kit form. The kit, according to this invention, comprises two separate pharmaceutical compositions: a first unit dosage form comprising a prophylactically or therapeutically effective amount of the compound of formula I, or a pharmaceutically acceptable salt or ester thereof, and a pharmaceutically acceptable carrier or diluent in a first unit dosage form, and a second unit dosage form comprising a prophylactically or therapeutically effective amount of the second active ingredient or drug, or a pharmaceutically acceptable salt or ester thereof, and a pharmaceutically acceptable carrier or diluent in a second unit dosage form. In one embodiment, the kit further comprises a container. Such kits are especially suited for the delivery of solid oral forms such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days or time in the treatment schedule in which the dosages can be administered.

Pharmaceutical Compositions

Another aspect of the present invention provides pharmaceutical compositions which comprise a compound of formula I, as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations, Because of their ease of administration, tablets and capsules represent the typical oral dosage unit form, in which case solid pharmaceutical carriers are typically employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Preparation of Compounds of the Invention

The compounds of formula I of the present invention can be prepared according to the procedures of the following Schemes and Examples, using appropriate materials and are further exemplified by the following specific examples. Moreover, by utilizing the procedures described herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogencarbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. All temperatures are degrees Celsius unless otherwise noted. Mass spectra (MS) were measured by electrospray ion-mass spectroscopy (ESMS).

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. CBZ and BOC are commonly used protecting groups in organic synthesis, and their removal conditions are known to those skilled in the art. For example, CBZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of CBZ groups can also be achieved by treatment with a solution of hydrogen bromide in acetic acid or by treatment with a mixture of TFA and dimethylsulfide. Removal of BOC protecting groups is carried out with a strong acid, such as trifluoroacetic acid, hydrochloric acid, or hydrogen chloride gas, in a solvent such as methylene chloride, methanol, or ethyl acetate.

The LC/MS analyses were preformed using a MICROMASS ZQ mass spectrometer coupled to an AGILENT 1100 Series HPLC utilizing a XTerra®MS, C18, 3.5 µm, 2.1×20 mm column eluting at 1.5 mL/min with a solvent gradient of 5 to 95% B over 0.75 min, followed by 95-98% B over 0.5 min solvent A=0.05% TFA in water; solvent B=0.05% TFA in acetonitrile. $^1$H-NMR spectra 5 were obtained on a 500 MHz VARIAN Spectrometer in $CDCl_3$ or $CD_3CN$ or as indicated and chemical shifts are reported as δ using the solvent peak as reference and coupling constants are reported in hertz (Hz).

List of Abbreviations:

Ac is acetyl; ACN is acetonitrile; $Ac_2O$ is acetic anhydride; AcOH is acetic acid; act is aqueous; Boc is tert-butyloxycarbonyl; Bu is butyl; n-BuLi is n-butyl lithium; t-BuOH is tert-butanol; t-BuLi is tert-butyl lithium; t-BuONO is tert-butyl nitrite; CAN is eerie ammonium nitrate; Celite™ is diatomaceous earth; Chiral OD is Chiralcel OD column; Chiral AS is Chiralpak AS column; $CuSO_4$ is copper sulfate; DAST is (diethylamino)sulfur trifluoride; DBU is 1,8-diazabicyclo-[5.4.0]undec-7-ene; DCM is dichloromethane or methylene chloride; DEAD: diethyl azodicarboxylate; DIBAL-H is diisobutylaluminumhydride; DIPEA or DIEA is N,N-diisopropyl ethyl amine (Hunig's base); DME is 1,2-dimethoxyethane; DMAP is 4-dimethyl amino pyridine; DMF is N,N-dimethylformamide; DMSO is dimethyl sulfoxide; DPPA is diphenyl phosphoryl azide; dppf is 1,1'-bis(diphenylphosphino)ferrocene; DTBPF is 1,1'-bis(di-tert-butylphosphino)ferrocene; EA is ethyl acetate; Et is ethyl; equiv is equivalent(s); ESI is electrospray ionization; $Et_2AlCN$ is diethylaluminum cyanide; $Et_3N$ is triethylamine; $Et_3SiH$ is triethylsilane; EtOAc is ethyl acetate; EtOH is ethyl alcohol; $Et_2O$ is diethyl ether; g is gram(s); h is hour(s); HATU is (2-(7-Aza-1H-benzotriazole-1-yl)-1,1,3,3-tetramethyluronium hexafluorophosphate); HCl is hydrochloric acid; HMPA is hexamethylphosphoramide; HPLC is high pressure liquid chromatography; in vacuo is rotary evaporation under diminished pressure; i-PrOH or IPA is isopropanol; $K_2CO_3$ is potassium carbonate; LC is liquid chromatography; LC/MS is liquid chromatography/mass spectroscopy; L is liter(s); LiHMDS is lithium hexamethyldisilazide; ml and mL is milliliter; M is molar; mmol is millimole(s); mCPBA is 3-Chloroperoxybenzoic acid; MeOH is methyl alcohol; $MgSO_4$ is magnesium sulfate; min is minute(s); MS is mass spectrum; MOMCl is chloromethyl methyl ether; MTBE is methyl tert-butyl ether; NaOH is sodium hydroxide; $NaN_3$ is sodium azide; NaOAC is sodium acetate; NMP is N-methyl-2-pyrrolidinone; NMR is nuclear magnetic resonance spectroscopy; $Pd_2(dba)_3$ is tris(dibenzylideneacetone)dipalladium(0); PE is petroleum ether; Ph is phenyl; $PPh_3$ is triphenyl phosphine; sat., sat'd., and sat is saturated; SFC is Supercritical Fluid Chromatography; $SiO_2$ is silicon dioxide; RP is reverse phase; rt and RT is room temperature; TEA is triethyl amine; TFA is trifluoroacetic acid; TFAA is trifluoroacetic anhydride; THF is tetrahydrofuran; TMP is 2,2,6,6-tetramethylpiperidine; Tos is 4-toluenesulfonyl; TosCl is 4-toluenesulfonyl chloride; OTs is 4-toluenesulfonate; and wt % is weight percent.

Several methods for preparing the compounds of this invention are illustrated in the following Schemes and Examples. Starting materials are either commercially available or made by known procedures in the literature or as illustrated. The present invention further provides processes for the preparation of compounds of structural formula I as defined above. In some cases the order of carrying out the foregoing reaction schemes may be varied to facilitate the reaction or to avoid unwanted reaction products. The following schemes and examples are provided for the purpose of illustration only and are not to be construed as limitations on the disclosed invention. All temperatures are degrees Celsius unless otherwise noted.

Scheme 1

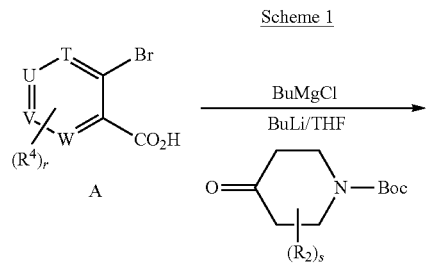

A

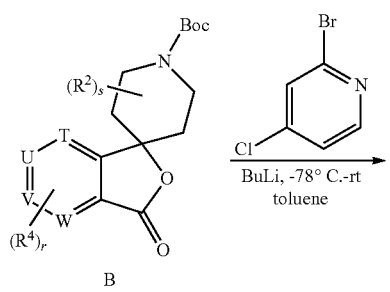

B

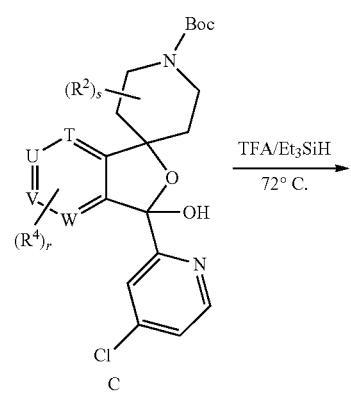

C

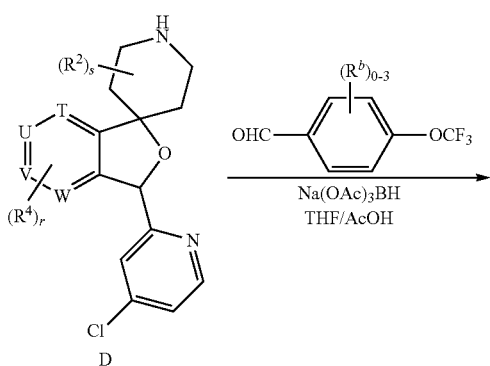

D

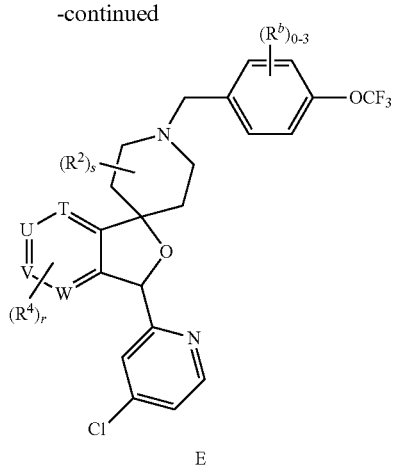

E

Compounds of the present invention may be prepared using procedures analogous to the procedures exemplified in Scheme 1. 2-bromo benzoic acid A was lithiated and reacted with N-Boc-4-piperidone followed by intra molecular cyclization to afford spirolatone B. 4-chloro-2-bromopyridine was lithiated and reacted with 8 to yield the 1,2-adduct C. Dehydroxylation of C by triethylsilane in trifluoroacetic acid gives the unprotected amine D. Reductive amination of D generated the desired product E.

Scheme 2

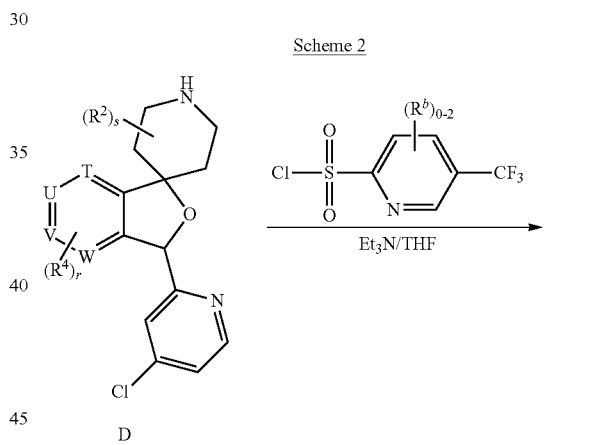

D

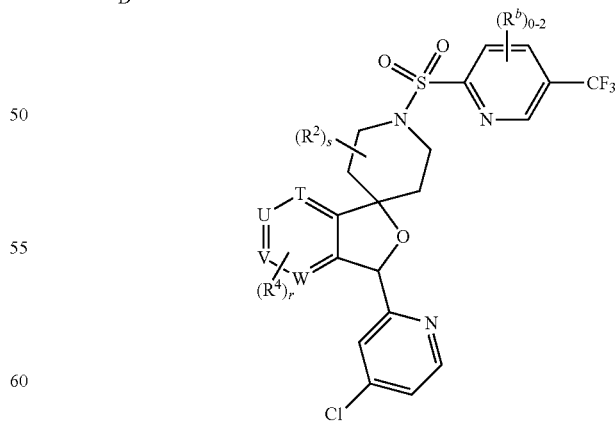

F

Sulfonamides of interest are prepared by the method outlined in Scheme 2. D was reacted with arylsulfonyl chloride in the presence of Et₃N to afford the desired product F.

The following Examples are provided to illustrate the invention and are not to be construed as limiting the scope of the invention in any manner.

Example 1

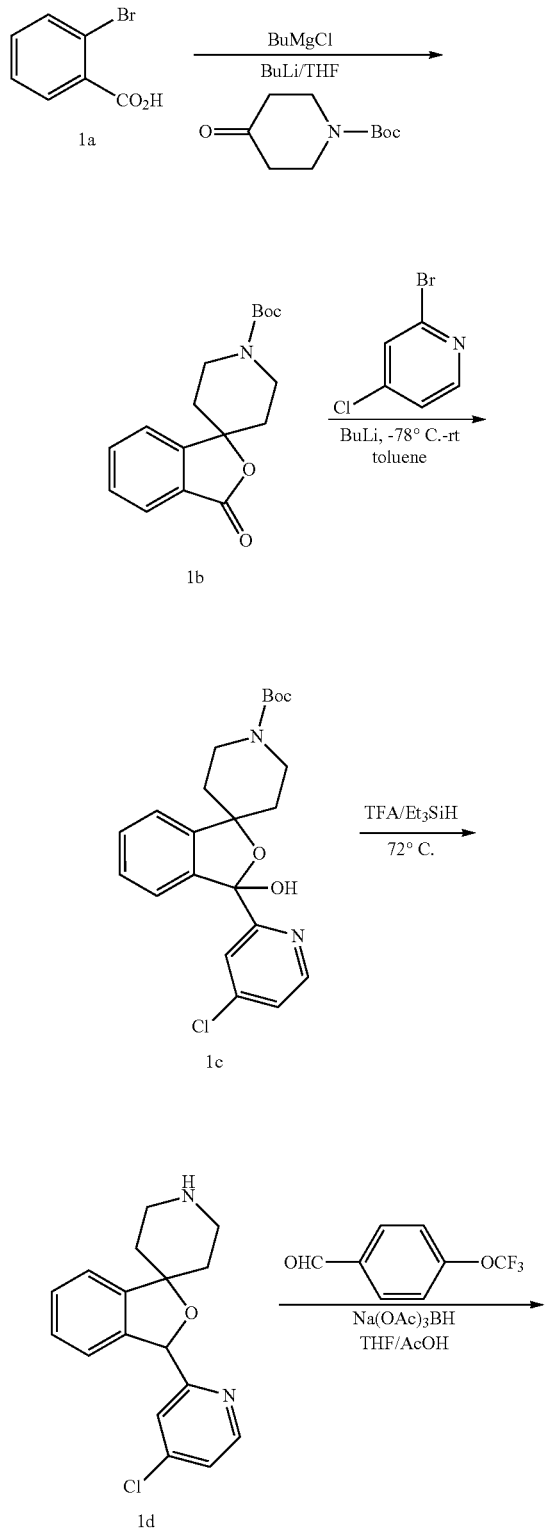

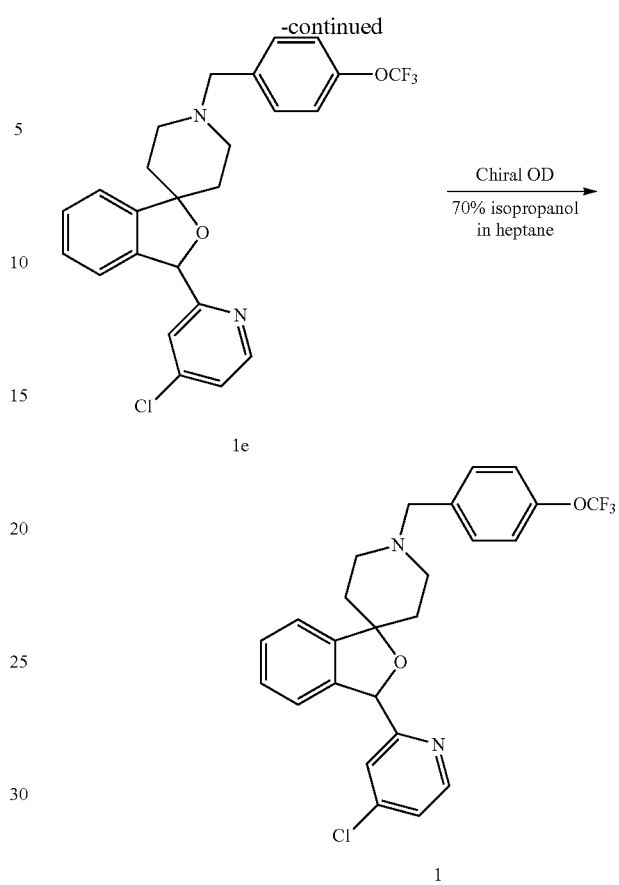

Step 1: To a solution of 1a (9.79 g, 48.7 mmol) in THF (50 mL) at −10° C. was added BuMgCl (21.92 mL, 2.0 M, 43.8 mmol), followed by the dropwise addition of BuLi (25.3 mL, 2.5 M, 63.3 mmol). The resulting solution was stirred at −10° C. for 30 min before 1-Boc-4-piperidone (10.67 g, 53.6 mmol) was added. After stirring at −5° C. for 1 h, acetic acid (15 mL) and water (40 mL) were added. The resulting solution was heated at 40° C. for 16 h. The reaction mixture was extracted with methyl tert-butylether (200 mL×2), and the combined organic phase was washed with NaOH (1N, 400 mL), sat. $K_2CO_3$ (400 mL), brine (400 mL), and dried over $Na_2SO_4$. After evaporating the volatiles, the residue was treated with heptane (100 mL) and the precipitate was collected by filtration to give 1b as white solid.

Step 2: To a solution of 2-bromo-4-chloropyridine (9.96 g, 51.8 mmol) in toluene (150 mL) was added dropwise n-BuLi (21.7 mL, 2.5M, 54.3 mmol) at −78° C. The resulting solution was stirred at −78° C. for 0.5 h before addition of 1b (7.85 g, 25.9 mmol) in one portion. The reaction mixture was stirred from −78° C. to rt for 16 h, and then quenched with sat. $NaHCO_3$ (300 mL). The mixture was extracted with EtOAc (200 mL×3). The combined organic phases were dried over $Na_2SO_4$, concentrated, and the residue was purified on silica gel using 10-40% EtOAc/hexanes to give 1c.

Step 3: A solution of 1c (7.5 g, 17.99 mmol), triethylsilane (5.75 mL, 36.0 mmol) in trifluoroacetic acid (70 mL) was heated at reflux for 3 h. After removing the volatile, the residue was dissolved in $CH_2Cl_2$ (300 mL) and extracted with HCl (1N, 250 mL×4). The acidic phase was then basified to pH 10 with NaOH (5N), and then extracted with CH$_2$Cl$_2$ (500 mL×3). The combined organic phases were dried over Na$_2$SO$_4$, and concentrated to give 1d as an oil.

Step 4: To a solution of 1d (5.54 g, 18.42 mmol) in THF/acetic acid (4/1, 250 mL) was added 4-trifluoromethoxybenzaldehyde (4.20 g, 22.10 mmol) and sodium triacetoxyborohydride (11.71 g, 55.3 mmol). The resulting mixture was stirred at rt for 3 h before quenching with the dropwise addition of water (50 mL). After removing the volatiles, the residue was diluted with CH$_2$Cl$_2$ (300 mL) and washed with NaOH (1N, 300 mL), sat. NaHCO$_3$ (300 mL), and dried over Na$_2$SO$_4$. After concentrating in vacuo, the residue was purified on silica gel using 20-40% EtOAc/hexanes to give 1e as a racemate.

Step 5: Compound 1e (4.8 g, 10.11 mmol) was separated on chiral OD column using 70% isopropanol/heptane to give compound 1 as an oil. $^1$HNMR (acetonitrile-d$_3$, 500 MHz) δ=8.537-8.526 (dd, J=5.4 Hz, 1H), 7.503-7.475 (m, 3H), 7.351-7.245 (m, 7H), 6.205 (s, 1H), 3.622 (s, 2H), 2.872-2.795 (m, 2H), 2.588-2.462 (m, 2H), 2.221-2.160 (m, 2H), 1.963-898 (m, 2H); m/z: calcd. for C$_{25}$H$_{22}$ClF$_3$N$_2$O$_2$: 474.903; found [M+H$^+$]: 475.22; 477.18.

Example 2

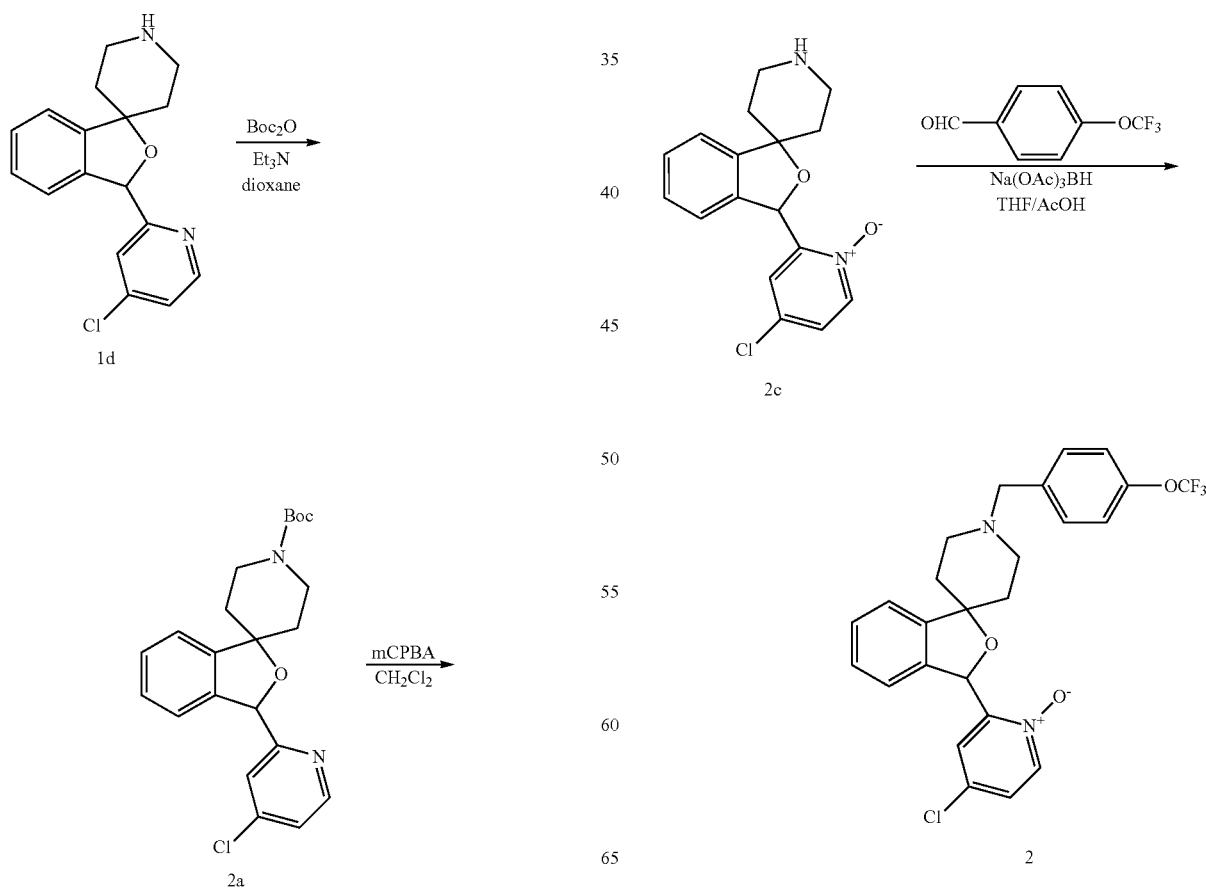

Step 1: To a solution of 1d (2.89 g, 9.6 mmol) and di-tert-butyl dicarbonate (2.51 g, 11.52 mmol) in dioxane (20 mL) and water (5 mL) was added Et₃N (5.35 mL, 38.4 mmol). The resulting solution was stirred at rt for 16 h. Then, after removing the volatiles, the residue was purified on silica gel using 10-40% EtOAc/hexanes to give 2a.

Step 2: To a solution of 2a (2.88 g, 7.18 mmol) in DCM (40 mL) was added mCPBA (2.254 g, 77%, 10.06 mmol) portion wise at 0° C. The resulting solution was stirred from 0° C. to rt for 16 h. The reaction solution was then treated with 10% potassium carbonate (200 mL) and extracted with DCM (150 mL×4). The combined DCM phases were dried over Na₂SO₄, and concentrated under vacuum to give 2b.

Step 3: Compound 2b (400 mg, 0.96 mmol) was separated on a chiral AS column using 20% isopropanol/heptane to give the faster eluting product ent-2b.

Step 4: To a solution of ent-2b (440 mg, 1.055 mmol) in DCM (4 mL) was added TFA (6 mL) and the resulting solution was stirred at rt for 1 h. The volatiles were evaporated under vacuum to give 2c as TFA salt.

Step 4: To a solution of 2c (575 mg, 1.055 mmol), 4-trifluoromethoxybenzaldehyde (284 mg, 1.49 mmol) in THF (6 mL) and acetic acid (1.5 mL) was added sodium triacetoxyborohydride (2.6 g, 12 mmol). The resulting mixture was stirred at rt for 3 h, then quenched by the dropwise addition of water (2 mL). After removing the volatiles, the residue was treated with 10% potassium carbonate (100 mL) and extracted with DCM (3×100 mL). The combined DCM phases were dried over Na₂SO₄, and concentrated under vacuum. The residue was further purified on RP-HPLC using 10-80% acetonitrile (0.1% TFA) over 10 min. The pure fraction was lyophilized to give 2 as the TFA salt, which was dissolved in 5 mL acetonitrile and HCl (0.41 mL, 2N) and lyophilized again to give 2 as the HCl salt. ¹HNMR (acetonitrile-$d_3$, 500 MHz) δ=8.290-8.276 (dd, J=7.0 Hz, 1H), 7.863-7.846 (dd, J=8.7 Hz, 2H), 7.712-7.697 (dd, J=7.5 Hz, 1H), 7.501-7.495 (dd, J=2.9 Hz, 1H), 7.410-7.389 (m, 4H), 7.335-7.305 (J=1.5 Hz, 1H), 7.225-7.239 (J=7.7 Hz, 1H), 6.849 (s, 1H), 4.301-4.4.294 (dd, J=3.7 Hz, 2H), 3.462-3.339 (m, 3H), 3.284-3.261 (m, 1H), 2.968-2.902 (m, 1H), 2.621-2.556 (m, 1H), 2.138-2.023 (m, 2H); m/z: calcd. for $C_{25}H_{22}ClF_3N_2O_3$: 490.902; found [M+H⁺]: 491.12; 493.08.

Example 3

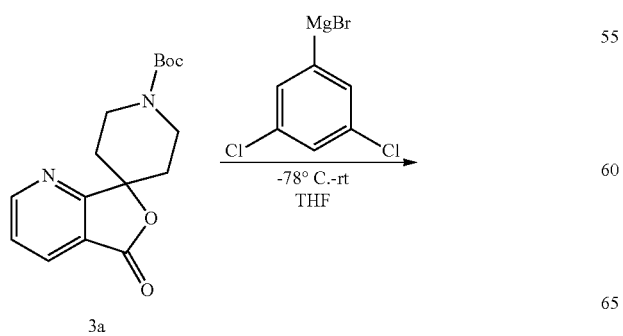

3a

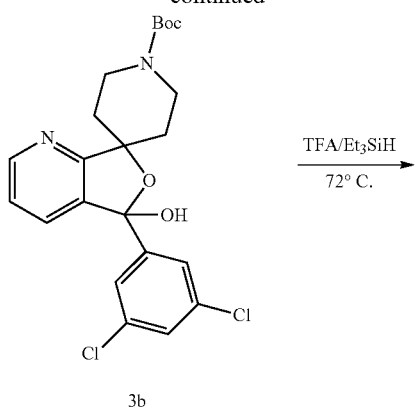

3b

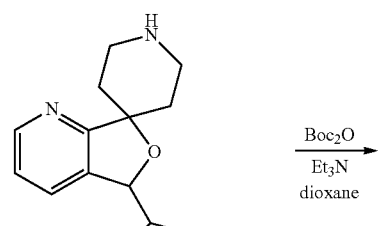

3c

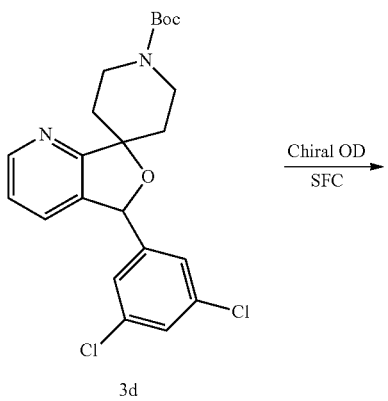

3d

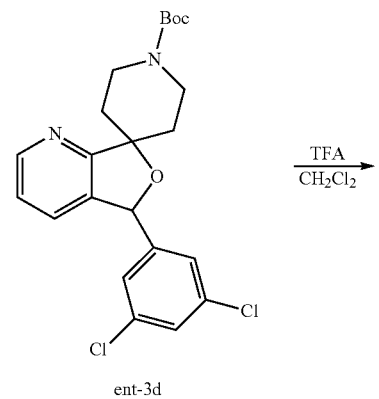

ent-3d

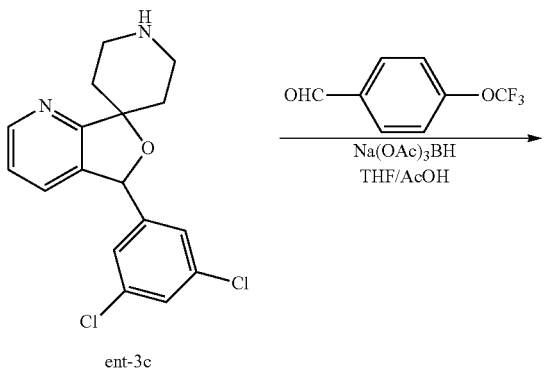

romethoxybenzaldehyde (19 mg, 0.10 mmol), and sodium triacetoxy-borohydride (142 mg, 0.67 mmol). The resulting mixture was stirred at rt for 2 h, and then quenched with water before concentrating under vacuum. The resulting residue was purified on RP-HPLC using 10-100% acetonitrile (0.05% TFA) to give 3 as the TFA salt. $^1$HNMR (acetonitrile-d$_3$, 500 MHz) δ=8.551-8.542 (dd, J=4.60 Hz, 1H), 7.669-7.652 (dd, J=8.5 Hz, 2H), 7.503-7.473 (m, 2H), 7.388 (m, 4H), 7.301-7.276 (m, 1H), 6.197 (s, 1H), 4.331 (s, 2H), 3.529-3.507 (m, 2H), 3.316-3.267 (m, 2H), 2.652-2.645 (m, 2H), 2.321-2313 (m, 2H), 2.067-1.987 (m, 2H); m/z: calcd. for $C_{25}H_{21}Cl_2F_3N_2O_2$: 509.35; found [M+H$^+$]: 508.90; 510.84; 512.05.

Example 4

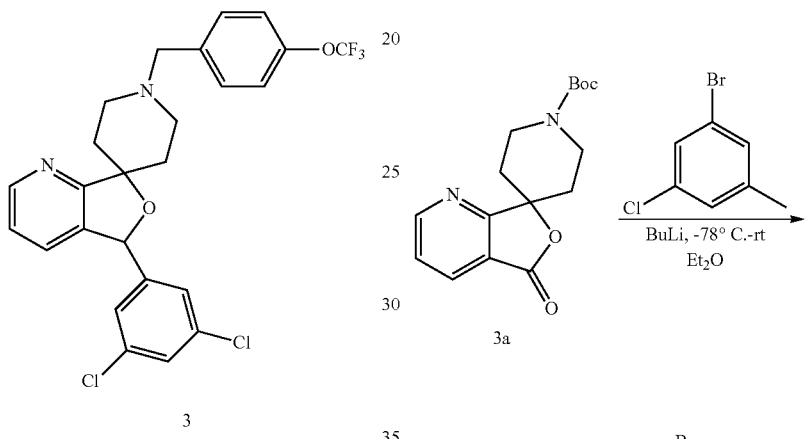

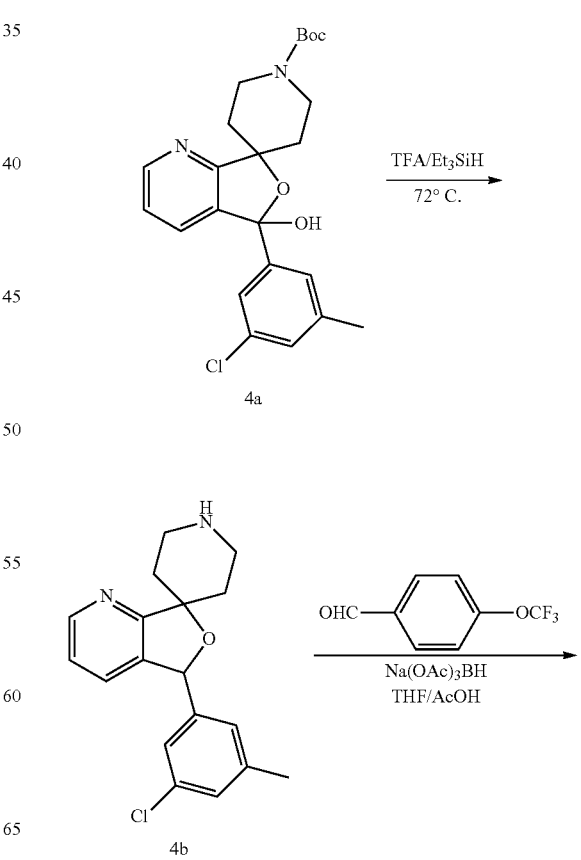

Step 1: To a solution of 3a (1.0 g, 3.29 mmol) in THF (50 mL) at −0° C. was added 3,5-dichlorophenyl magnesium bromide (19.7 mL, 9.86 mmol, 0.5M in THF). The resulting solution was stirred at rt for 16 h, and then quenched with sat. NaHCO$_3$ (20 mL), followed by the addition of ethyl acetate (100 mL). The organic phase was washed with sat. NaHCO$_3$ (3×100 mL), dried over Na$_2$SO$_4$, and concentrated under vacuum to give a residue. The residue was treated with DCM (20 mL), and the resulting solid 3b was collected by filtration. The filtrate was purified on silica gel using 20-100% ethyl acetate/hexanes to give 3b.

Step 2: A solution of 3b (1.12 g, 2.48 mmol) and triethylsilane (1.585 mL, 9.93 mmol) in trifluoroacetic acid (10 mL) was heated at 50° C. for 16 h. After removing the volatiles, the residue 3c was dissolved in dioxane (10 mL) and treated with Et$_3$N (1.73 mL, 12.41 mmol) and di-tert-butyl dicarbonate (0.812 g, 3.72 mmol). The resulting solution was stirred at rt for 4 h. After removing the volatiles, the resulting residue was purified on silica gel using 10-40% ethyl acetate/hexanes to give 3d.

Step 3: The recemate 3d (0.95 g, 2.20 mmol) was separated via chiral HPLC (OD column) to give the faster eluting product ent-3d.

Step 4: To a solution of ent-3d (0.41 g, 0.094 mmol) in DCM (5 mL) was added trifluoroacetic acid (5 mL), and the resulting solution was stirred at rt for 1 h. Then the volatiles were evaporated under vacuum to give ent-3e as the TFA salt.

Step 5: To a solution of ent-3e (45 mg, 0.08 mmol) in THF (1.6 mL) and acetic acid (0.4 mL) were added 4-trifluo- -continued

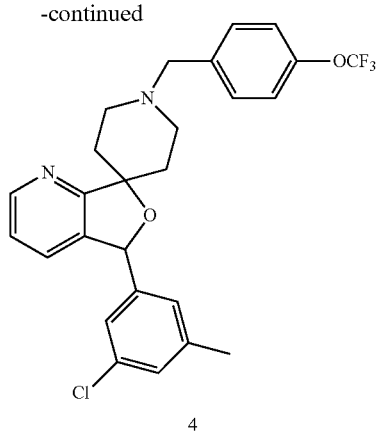

4

Example 5

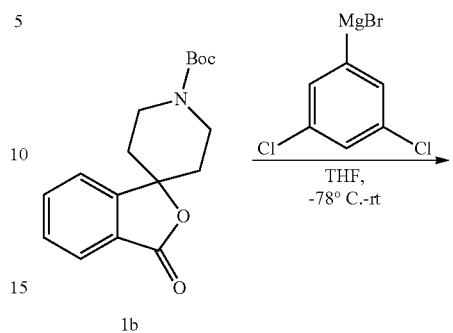

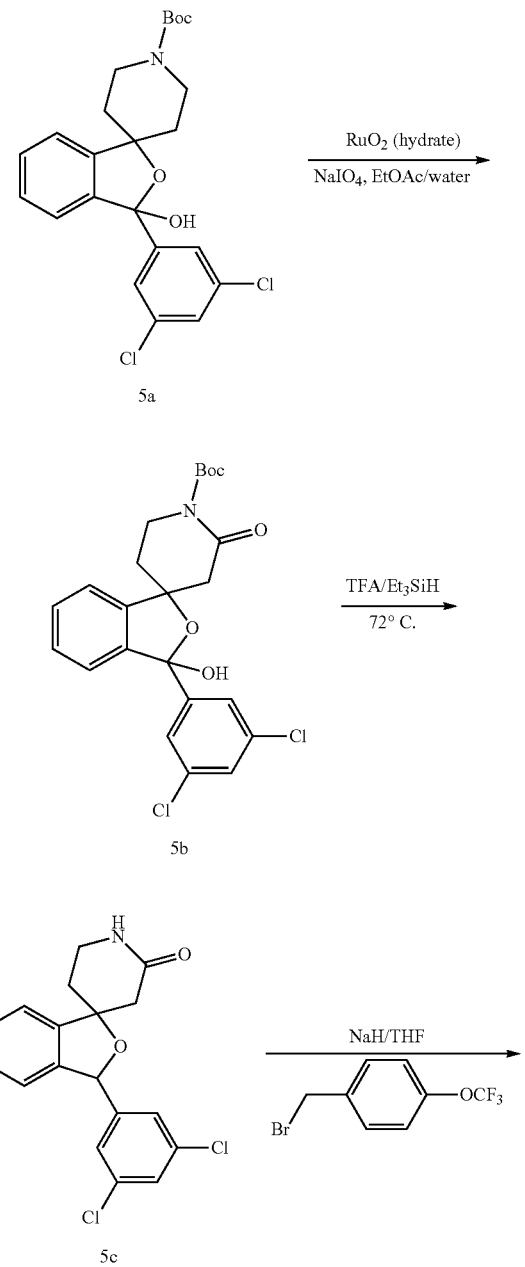

Step 1: To a solution of 3-bromo-5-chlorotoluene (754 mg, 3.67 mmol) in diethyl ether (20 mL) was added dropwise butyllithium (1.5 mL, 3.67 mmol) at −78° C. The resulting solution was stirred at −78° C. for 0.5 h before addition of 3a (558 mg, 1.835 mmol) as one portion. The reaction mixture was stirred from −78° C. to rt over 16 h before quenching with sat. NaHCO$_3$ (100 mL), followed by the addition of diethyl ether (50 mL) and ethyl acetate (100 mL). The organic phase was dried over Na$_2$SO$_4$, and concentrated on a rotary evaporator. The resulting residue was treated with DMSO (10 mL) to give the solid product 4a, which was collected by filtration, followed by washing with ethyl acetate. The filtrate, after removing the volatiles, was purified on RP-HPLC using 20-100% acetonitrile (0.1% TFA) to give 4a as the TFA salt.

Step 2: A solution of 4a (275 mg, 0.638 mmol) and triethylsilane (74.2 mg, 0.638 mmol) in trifluoroacetic acid (2.4 mL) was heated at 72° C. for 3 h. After the volatiles were evaporated on a rotary evaporator, the residue was dissolved in DCM (100 mL), and extracted with hydrochloric acid (3×50 mL, 1N). The combined aqueous layers were basified with sodium hydroxide (5N) to pH 10. The resulting precipitate was extracted with 30% isopropanol/chloroform (3×100 mL), and the combined organic phases were dried (Na$_2$SO$_4$) and concentrated to give 4b.

Step 3: To a solution of 4b (20 mg, 0.064 mmol), 4-trifluoromethoxybenzaldehyde (13.3 mg, 0.070 mmol) in THF (1.5 mL) and acetic acid (0.4 mL) was added sodium triacetoxyborohydride (98 mg, 0.464 mmol). The resulting solution was stirred at rt for 2 h, and then quenched with water. After removing the volatiles, the residue was purified on RP-HPLC using 10-100% acetonitrile (0.05% TFA) to give 4 as the TFA salt. $^1$HNMR (acetonitrile-d$_3$, 500 MHz) δ 8.537-8.528 (dd, J=4.5 Hz, 2H), 7.667-7.650 (dd, J=8.5 Hz, 2H), 7.449-434 (dd, J=7.6 Hz, 1H), 7.389-7.373 (dd, J=8.1 Hz, 2H), 7.284-7.269 (m, 1H), 7.226-7.198 (m, 2H), 7.145 (s, 1H), 6.159 (s, 1H), 4.328 (s, 2H), 3.525-3.503 (m, 2H), 3.292-3.275 (m, 2H), 2.687-2.620 (m, 1H), 2.353-2.288 (m, 1H), 2.057-1.958 (m 2H); m/z: calcd. for C$_{26}$H$_{24}$ClF$_3$N$_3$O$_2$: 488.93; found [M+H$^+$]: 489.16; 491.15.

-continued

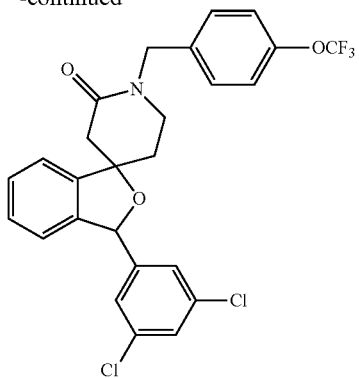

5

Step 1: To a solution of 1b (4 g, 13.2 mmol) in THF (80 mL) at −78° C. was added 3,5-dichlorophenylmagnesium bromide (52.7 mL, 26.4 mmol). The resulting solution was stirred from −78° C. to rt for 18 h before quenching by the addition of sat. NaHCO$_3$ (100 mL), The mixture was then extracted with ethyl acetate (100 mL×3), and the combined organic phases were dried over Na$_2$SO$_4$. After removing the volatiles, the residue was treated with DCM (50 mL) and the resulting precipitate was collected by filtration to give 5a as white solid.

Step 2: To a mixture of sodium periodate (8.79 g, 41.1 mmol) and ruthenium (IV) oxide hydrate (0.219 g, 1.643 mmol) in water (8 mL) was added a suspension of 5a (3.7 g, 8.22 mmol) in ethyl acetate (10 mL). The resulting mixture was stirred at rt for 2 h, then diluted with ethyl acetate (200 mL), washed with brine, and dried over Na$_2$SO$_4$. After removing the volatiles, the residue was purified on silica gel using 20-40% ethyl acetate/hexanes to give 5b.

Step 3: Compound 5b (3.0 g, 6.46 mmol) was treated with trifluoroacetic acid (24.89 mL) at rt for 2 min before the addition of triethylsilane (2.06 mL, 12.92 mmol). The resulting solution was heated at 72° C. for 1 h. After removing the volatiles, the residue was purified on silica gel using 0-10% methanol/DCM to give 5c as white solid.

Step 4: To a solution of 5c (40 mg, 0.115 mmol) in THF (101n L) was added sodium hydride (11.49 mg, 0.287 mmol, 60%) at 0° C. over 20 min, followed by 4-trofluoromethoxy-benzyl bromide (29.3 mg, 0.115 mmol). The resulting mixture was stirred from 0° C. to rt for 18 h. The reaction mixture was then quenched with water at 0° C. before extracting with ethyl acetate (50 mL). The organic phase was dried over Na$_2$SO$_4$. After removing the volatiles, the residue was purified on RP-HPLC using 60-100% acetonitrile (0.1% TFA) to give two sets of diastereomers 5. The more polar set of diastereomers: $^1$HNMR (chloroform-d, 500 MHz) δ 7.413-7.346 (m, 4H), 7.290-7.229 (m, 3H), 7.188-7.173 (dd, J=7.2 Hz, 1H), 7.0576-7.042 (dd, J=7.4 Hz, 1H), 6.239-6.127 (broad, 2H), 6.079 (s, 1H), 5.002-4.972 (dd, J=14.7 Hz, 1H), 4.505-4.476 (dd, J=14.8 Hz, 1H), 3.808-3.751 (m, 1H), 3.419-3.377 (m, 1H), 3.209-3.173 (dd, J=18.2 Hz, 1H), 3.048-3.011 (dd, J=18.2 Hz, 1H), 2.136-2.098 (m, 2H); m/z: calcd. for C$_{26}$H$_{20}$Cl$_2$F$_3$NO$_3$, calc. 522.343; found [M+H$^+$]: 522.01; 524.01. The less polar set of diastereomers: $^1$HNMR (chloroform-d, 500 MHz) δ 7.423-7.340 (m, 4H), 7.245-7.229 (t, J=8.3 Hz, 2H), 7.7.202-7.189 (dd, J=13.2 Hz, 2H), 7.076-7.061 (dd, J=7.4 Hz, 1H), 6.544-6.493 (broad, 2H), 6.168 (s, 1H), 5.023-4.993 (dd, J=4.3 Hz, 1H), 4.478-4.449 (dd, J=4.7 Hz), 3.823-3.765 (t, J=12.3 Hz, 1H), 3.461-3.421 (m, 1H), 2.994-2.954 (dd, J=7.9 Hz, 1H), 2.879-2.843 (dd, J=8.1 Hz, 1H), 2.416-2.352 (m, 1H), 2.148-2.111 (m, 1H); m/z: calcd. for C$_{26}$H$_{20}$Cl$_2$F$_3$NO$_3$, calc. 522.343; found [M+H$^+$]: 522.04; 524.02.

Example 6

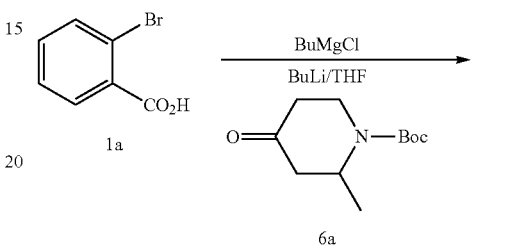

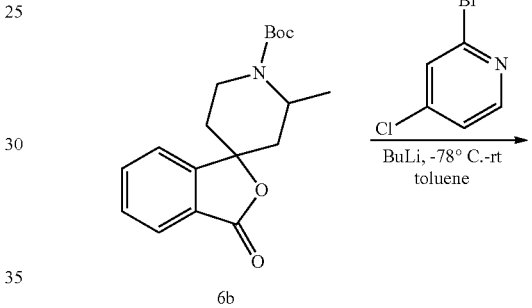

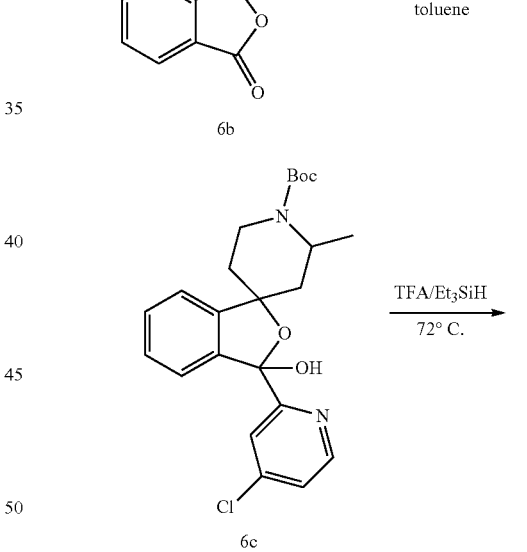

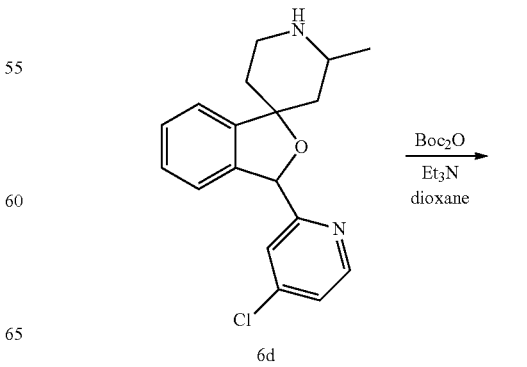

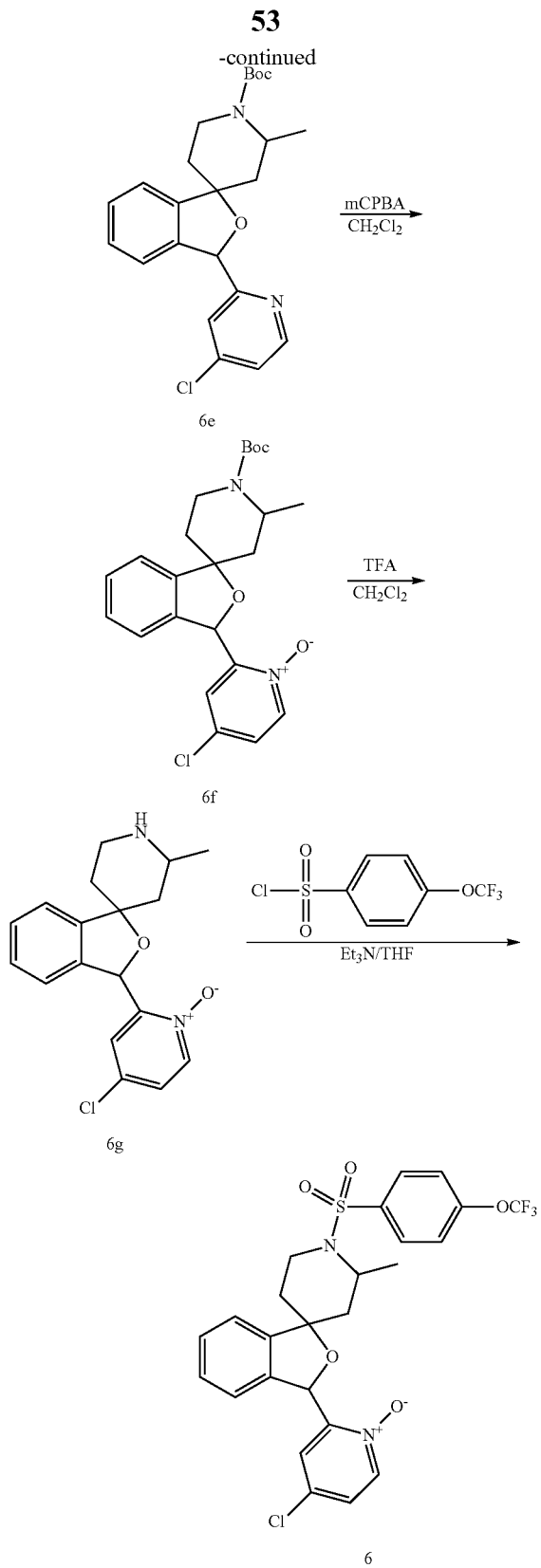

was added dropwise over 15 min. After stirring at −5° C. for 1 h, acetic acid (1.5 mL) and water (3 mL) were added. The resulting solution was heated at 40° C. for 16 h, and then extracted with methyl tert-butylether (30 mL×2). The combined organic phases were washed with NaOH (1N, 50 mL), sat. $K_2CO_3$ (50 mL), brine (50 mL), and dried over $Na_2SO_4$. After evaporating the volatiles, the residue was treated with heptane (20 mL) and the resulting precipitate was collected by filtration to give 6b as white solid.

Step 2: To a solution of 2-bromo-4-chloropyridine (564 mg, 2.93 mmol) in toluene (10 mL) was added dropwise n-BuLi (1.23 mL, 2.5M, 3.08 mmol) at −78° C. The resulting solution was stirred at −78° C. for 0.5 h before the addition of 6b (465 mg, 1.465 mmol) in one portion. The reaction mixture was stirred from −78° C. to rt for 16 h, and then quenched with sat. $NaHCO_3$ (30 mL). The mixture was extracted with EtOAc (20 mL×3), and the combined organic phases were dried over $Na_2SO_4$, and concentrated. The resulting residue was purified on silica gel using 10-40% EtOAc/hexanes to give 6c as an oil.

Step 3: A solution of 6c (0.47 g, 1.091 mmol), and triethylsilane (0.348 mL, 2.18 mmol) in trifluoroacetic acid (5 mL) was heated at reflux for 2 h. Then the volatiles were evaporated to give crude 6d.

Step 4: Crude compound 6d was treated $Et_3N$ (0.608 mL, 4.36 mmol) and di-tert-butyl dicarbonate (262 mg, 1.2 mmol) in dioxane (6 mL) for 17 h. After removal of the organic solvents, the residue was purified on silica gel using 10-40% ethyl acetate/hexanes to give 6e.

Step 5: To a solution of 6e (233 mg, 0.562 mmol) in DCM (10 mL) was added meta-chloroperbenzoic acid (214 mg, 0.955 mmol) at 0° C. and the resulting solution was stirred at rt for 20 h. Then 10% potassium carbonate (50 mL) was added and the mixture was extracted with DCM (4×50 mL). The combined organic phases were dried over $Na_2SO_4$, and concentrated to give 6f.

Step 6: Compound 6f (250 mg, 0.58 mmol) was treated with TFA (2 mL) at rt for 1.5 h. Then the volatiles were evaporated to give 6 g as the TFA salt.

Step 7: Compound 6 g (43 mg, 0.097 mmol) was to treated with $Et_3N$ (0.068 mL, 0.485 mmol) and 4-trifluoromethoxyphenylsulfonyl chloride (30 mg, 0.116 mmol) in THF (1 mL) at rt for 1 h. After removing the volatiles, the residue was purified on RP-HPLC using 20-100% acetonitrile (0.1% TFA) to give compound 6 as a mixture of four diasteromers. $^1$HNMR (chloroform-d, 500 MHz) δ 8.487-8.466 (2 set of dd, J=3.8 Hz, 1H), 7.981-7.963 (dd, J=8.8 Hz, 2H), 7.747-7.695 (2 set of dd, J=7.7 Hz, 1H), 7.547-7.479 (2 set of s, 1H), 7.405-7.388 (dd, J=8.4 Hz, 2H), 7.460-7.341 (m, 2H), 7.300-7.285 (m, 1H), 6.983-6.945 (2 set of dd, J=7.6 Hz, 1H), 6.890-6.878 (2 set of s, 1H), 4.579-4.443 (2 set of t, J=6.7 Hz, 1H), 4.053-3.909 (m, 1H), 3.623-3.473 (m, 1H), 2.377-2.335 (2 set of dd, J=6.4 Hz, 0.5H), 2.233-2.169 (m, 0.5H), 2.003-1.788 (m, 2H), 1.420-1.294 (2 set of dd, J=6.2 Hz, 3H); m/z: calcd. for $C_{25}H_{22}ClF_3N_2O_5S$: 554.966; found [M+H$^+$]: 555.03; 556.94.

Example 7

Step 1: To a solution of 1a (0.952 g, 4.74 mmol) in THF (5 mL) at −20° C. was added BuMgCl (2.249 mL, 2.0 M, 4.50 mmol), followed by the dropwise addition of BuLi (2.65 mL, 2.5 M, 6.63 mmol). The resulting solution was stirred at −10° C. for 30 min before 6a (1.01 g, 4.74 mmol) in THF (1.5 mL)

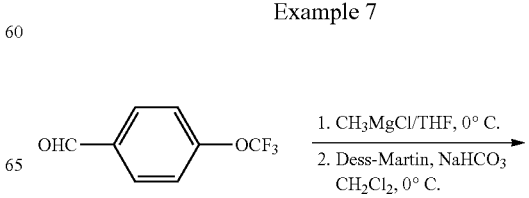

55

-continued

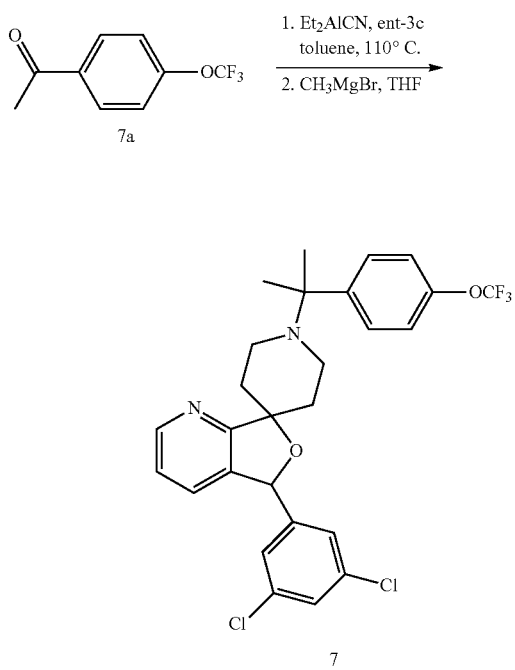

Step 1: To a solution of 4-trifluoromethoxybenzaldehyde (1.58 g, 8.31 mmol) in THF (12 mL) at 0° C. was added methylmagnesium chloride (3.88 mL, 3M, 11.63 mmol), and the resulting solution was stirred at 0° C. for 1 h. Then the reaction was quenched with sat. NaHCO₃ (10 mL) and extracted with ethyl acetate (100 mL). The organic phase was washed with brine (100 mL), dried over Na₂SO₄, and concentrated to give an alcohol. To a solution of the alcohol (0.83 g, 4.03 mmol) in DCM (20 mL) was added NaHCO₃ (0.338 g, 4.03 mmol) and Dess-Martin periodinane (2.56 g, 6.04 mmol) at 0° C. The resulting mixture was stirred for 3 h. After removing 70% of the solvent volume on a rotary evaporator, the mixture was purified on silica gel using 0-10% ethyl acetate/hexanes to give 7a.

Step 2: To a solution of ent-3c (141 mg, 0.422 mmol) and 7a (112 mg, 0.548 mmol) in toluene (3 mL) was added diethylaluminum cyanide (0.84 mL, 0.84 mmol, 1M). The resulting mixture was heated at 110° C. for 4 h. After removing the volatiles, the residue was purified on RP-HPLC using 100% acetonitrile (0.05% TFA). The residue was treated with THF (101n L) and methyl magnesium bromide (1.4 mL, 4.22 mmol, 3M) at rt for 3 h. The reaction was then quenched with sat. NaHCO₃ (50 mL), and extracted with DCM (2×50 mL). The combined organic phases were dried over Na₂SO₄ and concentrated. The resulting residue was purified on RP-HPLC using 20-100% acetonitrile (0.05% TFA) to give 7 as the TFA salt. $^1$HNMR (acetonitrile-$d_3$, 500 MHz) δ=8.537-8.528 (dd, J=4.7 Hz, 1H), 7.853-7.836 (dd, =8.8 Hz, 2H), 7.493-7.409 (m, 5H), 7.357 (s, 2H), 7.334-7.279 (m, 2H), 6.157 (s, 1H), 3.458-3.445 (m, 2H), 3.214-3.211 (m, 2H), 2.804-2.747 (m, 2H), 2.457-2.393 (m, 2H), 2.100-1.963 (m, 2H), 1.901 (s, 6H); m/z: calcd. for $C_{27}H_{25}Cl_2F_3N_2O_2$: 537.401; found [M+H$^+$]: 537.22; 539.24.

56

Example 8

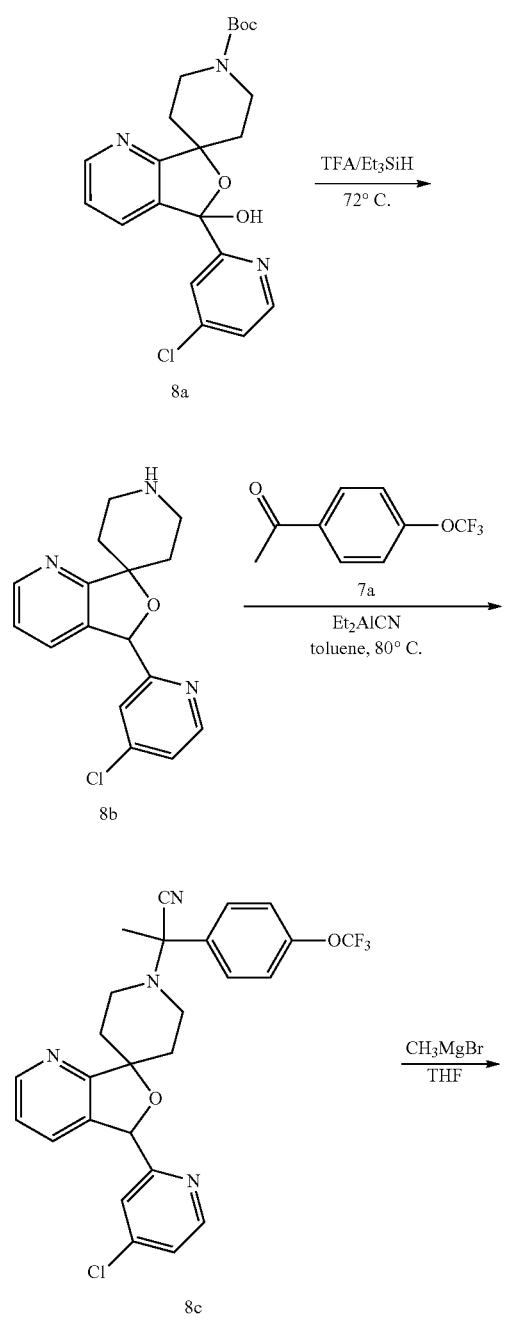

-continued

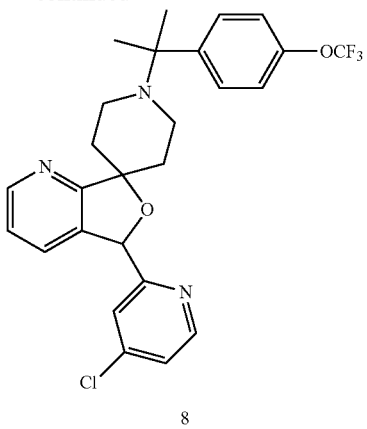

8

Step 1: To a solution of 2-bromo-4-chloropyridine (873 mg, 4.53 mmol) in toluene (20 mL) was added butyllithium (1.9 mL, 4.76 mmol, 2.5 M) at −78° C. The resulting solution was stirred at −78° C. for 0.5 h before the addition of 3a (690 mg, 2.27 mmol) in one portion. The mixture was stirred from −78° C. to rt for 16 h before quenching with sat. NaHCO$_3$. The mixture was extracted with diethyl ether (50 mL) and ethyl acetate (100 mL). The combined organic phases were dried over Na$_2$SO$_4$, and concentrated. The resulting residue was purified on silica gel using 10-40% ethyl acetate/hexanes to give 8a.

Step 2: A solution of 8a (680 mg, 1.627 mmol), and triethylsilane (0.52 mL, 3.25 mmol) in trifluoroacetic acid (6.3 mL, 81 mmol) was heated at 75° C. for 16 h. After removing the volatiles, the residue was dissolved in DCM (100 mL), and washed with hydrochloric acid (2×50 mL, 1N). The combined acidic aqueous phases were basified to pH 10 with 5 N NaOH before extracting with DCM (3×50 mL). The combined DCM phases were dried over Na$_2$SO$_4$, and concentrated to give 8b as the free base.

Step 3: To a solution of 8b (173 mg, 0.573 mmol) and 7a (117 mg, 0.573 mmol) in toluene (2 mL) was added diethylaluminium cyanide (1.15 mL, 1.15 mmol, 1M) and the resulting mixture was heated at 80° C. for 3 h. After cooling to rt, the mixture was partitioned between DCM (50 mL) and 10% potassium tartrate solution (50 mL). The water phase was extracted with DCM (2×50 mL). The combined organic phases were dried over Na$_2$SO$_4$, and concentrated. The resulting residue was purified on RP-HPLC using 10-100% acetonitrile (0.1% TFA) to give 8c as the TFA salt.

Step 4: To a solution of 8c (40 mg, 0.078 mmol) in THF (6 mL) was added methylmagnesium bromide (0.26 mL, 0.78 mmol, 3M) at 0° C. and the resulting solution was stirred at rt for 2 h before quenching with water, followed by extraction with DCM. The organic phase was dried over Na$_2$SO$_4$, and concentrated. The resulting residue was purified on RP-HPLC using 10-100% acetonitrile (0.1% TFA) to give 8 as the TEA salt. $^1$HNMR (acetonitrile-d$_3$, 500 MHz) δ=8.534-8.505 (m, 2H), 7.913-7.854 (dd, J=8.7 Hz, 2H), 7.773-7.758 (m, 1H), 7.549 (s, 1H), 7.434-7.417 (dd, J=8.6 Hz, 2H), 7.386-7.372 (m, 1H), 7.316-7.291 (m, 1H), 6.259 (s, 1H), 3.735-3.583 (m, 2H), 3.340-3.238 (m, 2H), 2.748-2.684 (m, 1H), 2.534-2.469 (m, 1H), 2.114-2.014 (m 1H), 1.984-1.962 (m, 1H), 1.953 (s, 6H); ink: calcd. for C$_{26}$H$_{25}$ClF$_3$N$_3$O$_2$: 503.944; found [M+H$^+$]: 504.16; 506.17.

Example 9

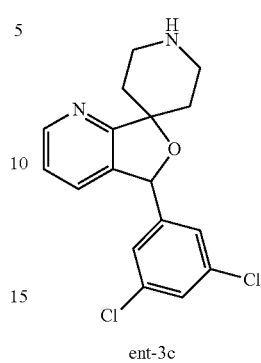
ent-3c

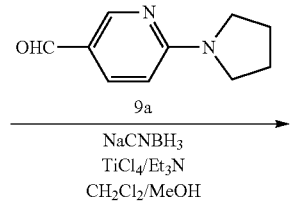
9a

NaCNBH$_3$
TiCl$_4$/Et$_3$N
CH$_2$Cl$_2$/MeOH

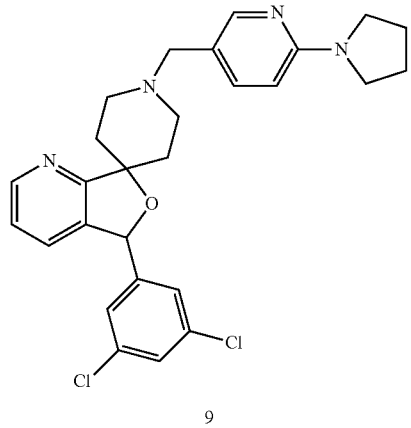
9

To a mixture of ent-3c (40 mg, 0.119 mmol) and 9a (25.2 mg, 0.143 mmol) in DCM (2 mL) were added Et$_3$N (36.2 mg, 0.358 mmol) and titanium tetrachloride (60 μL, 0.060 mmol, 1 M). The resulting solution was stirred at rt for 18 h. Then sodium cyanoborohydride (7.50 mg, 0.119 mmol) in methanol (0.1 mL) was added, and the mixture was stirred at rt for 18 h. After removing the volatiles, the residue was purified on RP-HPLC using 10-100% acetonitrile (0.05% TFA) to give 9 as the TFA salt. $^1$HNMR (acetonitrile-d$_3$, 500 MHz) δ=8.550-8.541 (dd, J=4.3 Hz, 1H), 8.191 (s, 1H), 8.022-8.004 (dd, J=9.0 Hz, 1H), 7.522-7.507 (m, 2H), 7.470 (s, 1H), 7.393 (s, 2H), 7.350-7.302 (m, 1H), 6.998-6.979 (dd, J=9.4 Hz, 1H), 6.213 (s, 1H), 4.255 (s, 2H), 3.580-3.534 (m, 6H), 3.337-3.317 (m, 2H), 2.661-2.587 (m, 1H), 2.330-2.278 (m, 1H), 2.099-2.019 (m, 5H), 1.958-1.953 (m, 1H); m/z: calcd. for C$_{27}$H$_{28}$Cl$_2$N$_4$O: 495.44; found [M+H$^+$]: 495.10; 497.08.

Example 10

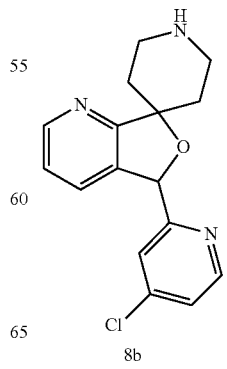
8b

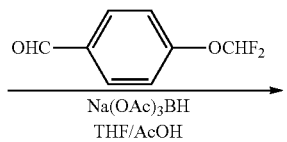

Na(OAc)$_3$BH
THF/AcOH

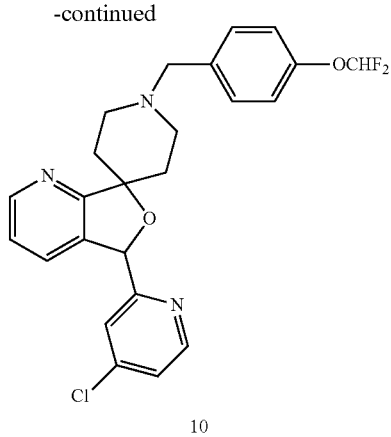

10

To a solution of 8b (20 mg, 0.066 mmol), and 4-difluoromethoxybenzaldehyde (20 mg, 0.116 mmol) in THF (2 mL) and acetic acid (0.5 mL) was added sodium triacetoxyborohydride (98 mg, 0.464 mmol). The resulting solution was stirred at rt for 2 h, and then quenched with 1N HCl. After removing the volatiles, the residue was purified on RP-HPLC using 10-80% acetonitrile (0.05% TFA) to give 10 as the TFA salt. $^1$HNMR (acetonitrile-$d_3$, 500 MHz) δ=8.568-8.539 (m, 2H), 7.822-7.806 (dd, J=7.7 Hz, 1H), 7.619-7.602 (m, 3H), 7.426-7.412 (m, 1H), 7.345-7.319 (m, 1H), 7.262-7.245 (m, 2H), 7.004-6.708 (t, J=73.8 Hz, 1H), 6.324 (s, 1H), 4.354 (s, 2H), 3.573-3.549 (m, 2H), 3.442-3.377 (m, 2H), 2.580-2.571 (m, 1H), 2.380-2.372 (m, 1H), 2.153-2.035 (in 2H); m/z: calcd. for $C_{24}H_{22}ClF_2N_3O_2$: 457.900; found [M+H$^+$]: 458.20; 460.23.

Example 11

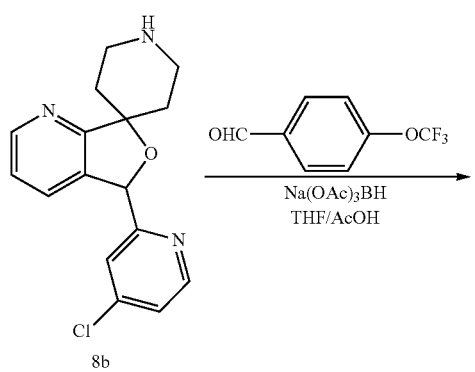

To a solution of 8b (80 mg, 0.265 mmol) and trifluoromethoxybenzaldehyde (65.5 mg, 0.345 mmol) in THF (12 mL) and acetic acid (3 mL) was added sodium triacetoxyborohydride (169 mg, 0.795 mmol). The resulting mixture was stirred at rt for 2 h, and then quenched with water. After removing the volatiles, the residue was purified on RP-HPLC using 20-100% acetonitrile (0.05% TFA) to give 11 as the TFA salt. $^1$HNMR (acetonitrile-$d_3$, 500 MHz) δ=8.572-8.535 (m, 2H), 7.837-7.821 (dd, J=7.7 Hz, 1H), 7.690-7.632 (m, 3H), 7.432-7.387 (m, 3H), 7.353-7.328 (m, 1H), 6.336 (s, 1H), 4.379 (s, 2H), 3.577-3.553 (m, 2H), 3.483-3.370 (m, 2H), 2.613-2.548 (m, 1H), 2.410-2.344 (m, 1H), 2.150-2.042 (m 2H); m/z: calcd. for $C_{24}H_{21}ClF_3N_3O_2$: 475.891; found [M+H$^+$]: 476.14; 478.15.

Example 12

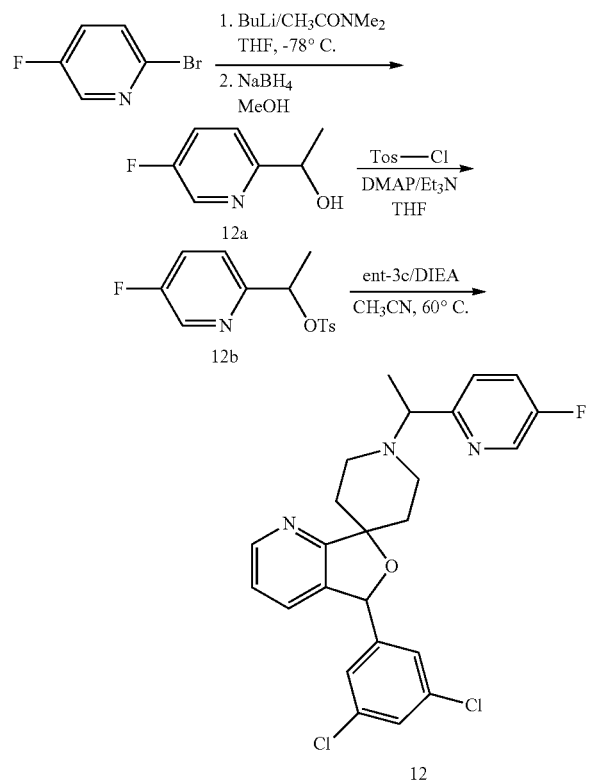

Step 1: To a solution of 2-bromo-5-fluoropyridine (1.911 g, 10.86 mmol) in diethyl ether (20 mL) at −78° C. was added dropwise butyllithium (4.34 mL, 10.86 mmol, 2.5M). The resulting solution was stirred at −78° C. for 0.5 h before the addition of N,N-dimethyl acetamide (1.135 g, 13.03 mmol). The reaction solution was aged at −78° C. for 1 h, and then slowly warm to rt. The reaction was then quenched with hydrochloric acid (20 mL, 1N) at −78° C. The resulting solution was stirred from −78° C. to rt overnight. The reaction solution was then basified with NaOH (1N), and extracted with EtOAc (2×100 mL). The combined organic phases were washed with brine, dried over Na$_2$SO$_4$, and concentrated to give a residue. To the residue was added methanol (20 mL), at 0° C., and sodium borohydride (1.958 g, 51.8 mmol). The resulting mixture was stirred at rt for 20 min before quenching with water. After removing the volatiles, the mixture was extracted with EtOAc (2×100 mL). The combined organic phases were washed with sat. NaHCO$_3$, dried over Na$_2$SO$_4$, and concentrated. The residue was purified on silica gel using 10-40% ethyl acetate/hexanes to give 12a.

Step 2: To a solution of 12a (0.24 g, 1.7 mmol) in THF (5 mL) at 0° C. was added p-toluenesulfonyl chloride (389 mg, 2.040 mmol), Et₃N (0.60 mL, 4.30 mmol), and DMAP (208 mg, 1.7 mmol). The resulting solution was stirred at rt for 2 h. After removing the volatiles, the residue was purified on silica gel using 10% ethyl acetate/hexanes to give 12b.

Step 3: A solution of ent-3c (76 mg, 0.135 mmol), 12b (43.8 mg, 0.148 mmol), and DIEA (0.12 mL, 0.675 mmol) in acetonitrile (2 mL) was heated at 60° C. overnight. The mixture was purified on RP-HPLC using 10-100% acetonitrile (0.05% TFA) to give 12 as the TFA salt. $^1$HNMR (acetonitrile-d₃, 500 MHz) δ=8.573-8.542 (dd, J=5.9 Hz, 1H), 7.677-7.602 (m, 2H), 7.494-7.452 (m, 2H), 7.353 (s, 2H), 7.305-7.280 (m, 1H), 6.161 (s, 1H), 4.677 (m, 1H), 3.745-3.724 (m, 1H), 3.510-3.366 (m, 2H), 3.250-3.201 (m, 1H), 2.401-2.354 (m, 2H), 2.093-1.992 (m, 2H), 1.757-1.747 (dd, J=6.7 Hz, 3H); nm/z: calcd. for $C_{24}H_{22}Cl_2FN_3O$: 458.36; found [M+H⁺]: 457.99; 459.92.

Example 13

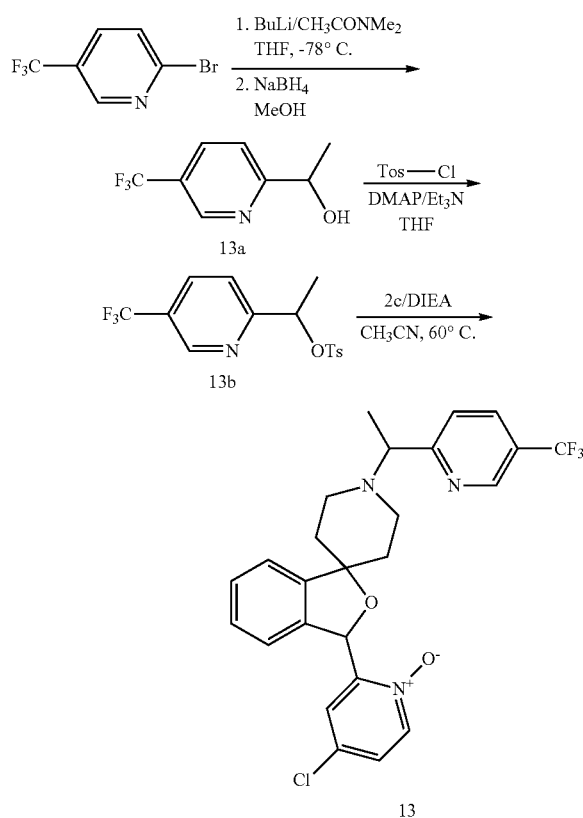

13

Compound 13 was prepared according to the procedure described in Example 12: $^1$HNMR (acetonitrile-d₃, 500 MHz) δ=9.003 (s, 1H), 8.347-8.335 (dd, J=5.9 Hz, 1H), 8.236-8.220 (dd, J=8.0 Hz, 1H), 7.745-7.690 (m, 2H), 7.555-7.541 (m, 1H), 7.446-7.417 (m, 2H), 7.360-7.315 (m, 2H), 6.876 (s, 1H), 4.728-4.715 (m, 1H), 3.782-3.733 (m, 1H), 3.585-3.355 (m, 3H), 2.390-2.100 (m, 4H), 1.763-1.749 (dd, J=6.6 Hz, 3H); m/z: calcd. for $C_{25}H_{23}ClFN_3O_2$: 489.917; found [M+H⁺]: 490.07; 492.06.

Example 14

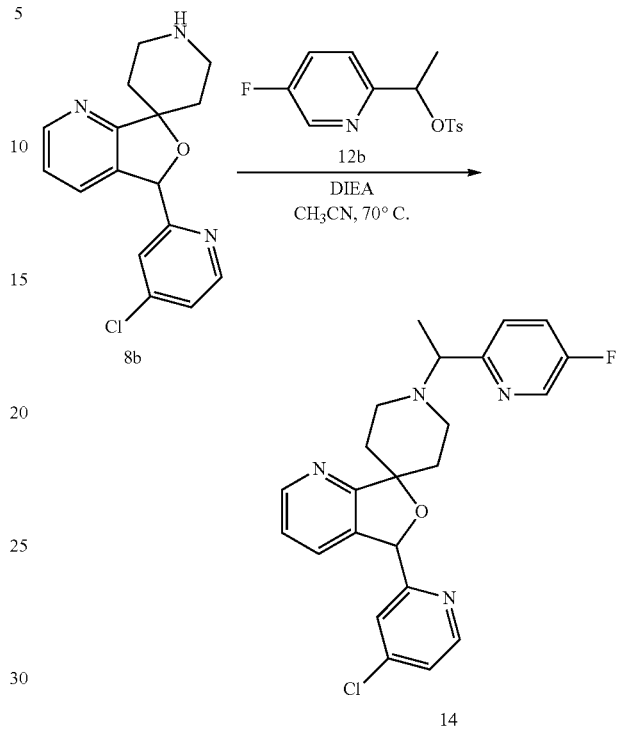

A solution of 8b (20 mg, 0.066 mmol), 12b (23.5 mg, 0.080 mmol), and DIEA (60 mg, 0.464 mmol) in acetonitrile (1 mL) was heated at 70 T for 16 h. After removing the volatiles, the residue was purified on RP-HPLC using 10-70% acetonitrile (0.1% TFA) to give 14 as the TFA salt. $^1$HNMR (acetonitrile-d₃, 500 MHz) δ=8.593-8.588 (dd, J=2.7 Hz, 1H), 8.532-8.522 (dd, 5.2 Hz, 2H), 7.772-7.756 (m, 1H), 7.700-7.666 (m, 1H), 7.617-7.600 (m, 1H), 7.551 (s, 1H), 7.383-7.369 (m, 1H), 7.319-7.294 (m, 1H), 6.269 (s, 1H), 4.670 (m, 1H), 3.804-3.725 (m, 2H), 3.497-3.400 (m, 2H), 2.603-2.408 (m, 2H), 2.120-2.012 (m 2H), 1.953-1.948 (dd, J=2.4 Hz, 3H); m/z: calcd. for $C_{23}H_{22}ClFN_4O$: 424.90; found [M+H⁺]: 425.08; 427.07.

Example 15

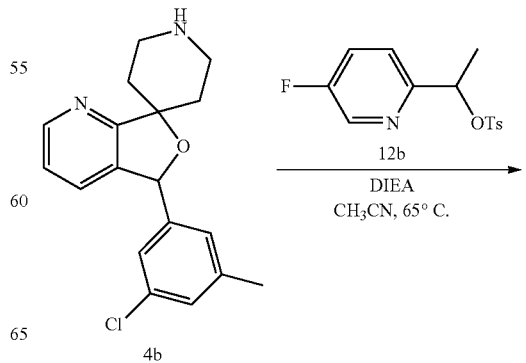

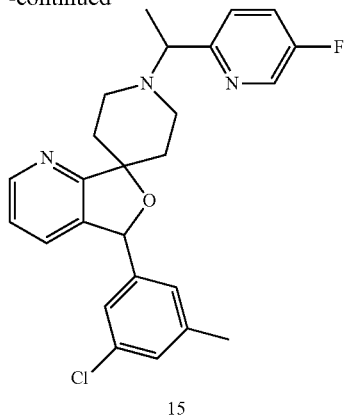

15

A solution of 4b (20 mg, 0.064 mmol), 12b (20.64 mg, 0.070 mmol), and DIEA (24.6 mg, 0.191 mmol) in acetonitrile (2 mL) was heated at 65° C. for 16 h. After removing the volatiles, the residue was purified on RP-HPLC using 10-100% acetonitrile (0.05% TFA) to give 15 as the TFA salt. $^1$HNMR (acetonitrile-$d_3$, 500 MHz) δ=8.567-8.531 (m, 2H), 7.674-7.635 (m, 2H), 7.437-7.422 (m, 1H), 7.285-7.259 (m, 1H), 7.215 (s, 1H), 7.160 (s, 1H), 7.114 (s, 1H), 6.117 (s, 1H), 4.675-4.663 (m, 1H), 3.762-3.705 (m, 1H), 3.522-3.489 (m, 1H), 3.409-3.300 (m, 1H), 3.240-3.187 (m, 1H), 2.733-2.700 (m, 2H), 2.398-2.353 (m 1H), 2.087-1.980 (m, 1H), 1.750-1.736 (dd, J=6.8 Hz, 3H); m/z: calcd. for $C_{25}H_{25}ClFN_3O$: 437.94; found [M+H$^+$]: 438.19; 440.15.

Example 16

To a solution of 2c (0.020 g, 0.064 mmol) in THF (1 mL) was added Et$_3$N (26 mg, 0.256 mmol) and 4-trifluoromethoxyphenylsulfonylchloride (20 mg, 0.077 mmol). The resulting solution was stirred at rt for 1 h. After removing the volatiles, the residue was purified on RP-HPLC using 20-100% acetonitrile (0.1% TFA) to give 16 as the TFA salt. $^1$HNMR (acetonitrile-$d_3$, 500 MHz) δ=8.228-8.214 (dd, J=5.8 Hz, 1H), 7.947-7.930 (dd, J=8.8 Hz, 2H), 7.676-7.662 (dd, J=7.3 Hz, 1H), 7.548-7.530 (dd, J=8.5 Hz, 2H), 7.387-7.337 (m, 3H), 7.286-7.242 (m, 2H), 6.748 (s, 1H), 3.895-3.796 (m, 2H), 2.878-2.823 (m 1H), 2.741-710 (m, 1H), 2.813-2.748 (m, 1H), 2.593-2.480 (m, 1H), 2.382-2.328 (m, 1H); 2.044-1.960; calcd. for $C_{24}H_{20}ClF_3N_2O_5S$: 540.939; found [M+H$^+$]: 541.12; 543.02.

Example 17

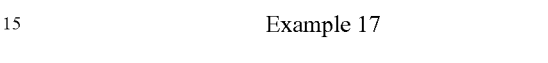

To a solution of 2c (0.020 g, 0.064 mmol) in THF (1 mL) was added Et$_3$N (26 mg, 0.256 mmol) and 2-(5-trifluoromethylpyridyl)sulfonylchloride (189 mg, 10% benzene solution, 0.077 mmol). The resulting solution was stirred at rt for 1 h. After removing the volatiles, the residue was purified on RP-HPLC using 20-100% acetonitrile (0.1% TFA) to give 17 as the TFA salt. $^1$HNMR (acetonitrile-$d_3$, 500 MHz) δ=9.093 (s, 1H), 8.369-8.352 (dd, J=8.3 Hz, 1H), 8.256-8.243 (dd, J=6.8 Hz, 1H), 8.162-8.146 (dd, J=8.3 Hz, 2H), 7.699-7.684 (dd, J=7.7 Hz, 1H), 7.436-7.431 (dd, J=2.6 Hz, 1H), 7.397-7.352 (m, 2H), 7.308-7.250 (m, 2H), 6.780 (s, 1H), 4.003-3.908 (m, 2H), 3.317-3.261 (m, 1H), 3.211-3.155 (m, 1H), 2.766-2.744 (m, 1H), 2.370-2.307 (m, 1H), 2.041-1.997 (m, 2H); m/z: calcd. for $C_{23}H_{19}ClF_3N_3O_4S$: 525.928; found [M+H$^+$]: 526.12; 528.01.

Example 18

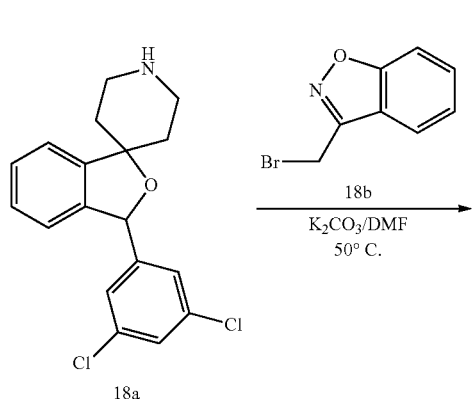

A mixture of 18a (20 mg, 0.060 mmol), 18b (12.7 mg, 0.060 mmol), and potassium carbonate (24.8 mg, 0.18 mmol) in DMF (1 ml) was heated at 50° C. for 2 h. The reaction solution was purified on RP-HPLC using 10-100% acetonitrile (0.05% TFA) to give 18 as the TFA salt. $^1$HNMR (acetonitrile-$d_3$, 500 MHz) δ=8.047-8.031 (dd, J=8.1 Hz, 1H), 7.738-7.723 (m, 2H), 7.503-7.452 (m, 1H), 7.448 (s, 1H), 7.399-7.321 (m, 5H), 7.067-7.052 (dd, J=7.5 Hz, 1H), 6.173 (s, 1H), 4.755 (s, 2H), 3.736-3.701 (m, 2H), 3.550-3.450 (m, 2H), 2.800-2.745 (m, 1H), 2.41'3-2.404 (m, 1H), 2.141-2.110 (m, 1H), 2.036-2.001 (in 1H); m/z: calcd. for $C_{26}H_{22}Cl_2N_2O_2$: 465.37; found [M+H$^+$]: 465.00; 466.94.

Example 19

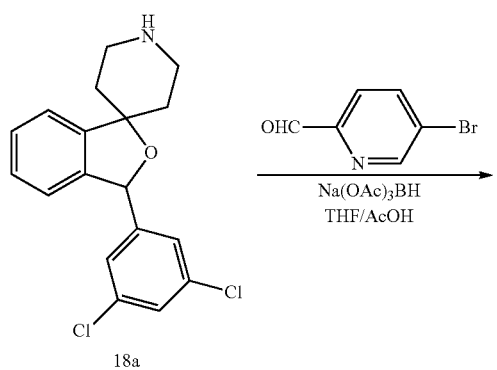

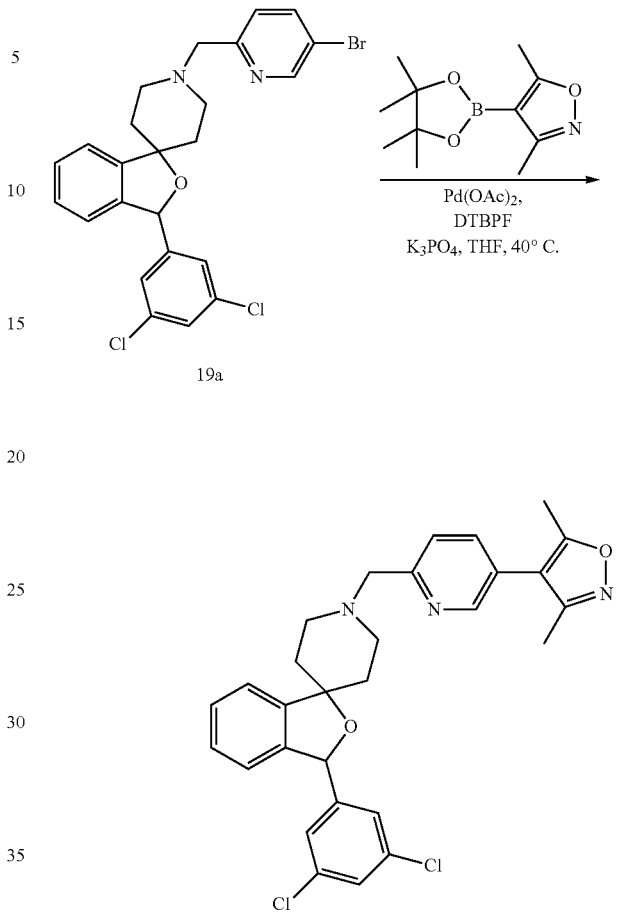

Step 1: To a solution of 18a (300 mg, 0.898 mmol) and 2-formyl-5-bromopyridine (200 mg, 1.077 mmol) in THF (30 mL) and acetic acid (10 mL) was added sodium triacetoxyborohydride (951 mg, 4.49 mmol). The resulting mixture was stirred at rt for 1.5 h, and then quenched with water. After removing the volatiles, the residue was purified on RP-HPLC to give 19a as the TFA salt.

Step 2: A mixture of 19a (50 mg, 0.099 mmol), 3,5-dimethylisoxazole-4-boronic acid pinacol ester (26.5 mg, 0.119 mmol), K$_3$PO$_4$ (0.6 mL, 0.6 mmol, 1M), palladium (II) acetate (2.3 mg, 0.01 mmol) and ligand DTBPF (0.65 mg, 0.01 mmol) in THF (2 mL) was heated at 40° C. under nitrogen for 24 h. After removing the volatiles, the residue was purified on RP-HPLC using 20-70% acetonitrile (0.05% TFA) to give 19 as the TFA salt. $^1$HNMR (acetonitrile-$d_3$, 500 MHz) δ=8.646-8.642 (dd, J=1.7 Hz, 1H), 7.915-7.894 (m, 1H), 7.623-7.607 (m, 1H), 7.455-7.419 (m, 2H), 7.374-7.338 (m, 4H), 7.089-7.074 (dd, J=7.7 Hz, 1H), 6.201 (s, 1H), 4.554 (s, 2H), 3.840-3.804 (m, 2H), 3.641-3.564 (m, 2H), 2.673-2.607 (m, 1H), 2.617-2.607 (m, 1H), 2.435 (s, 3H), 2.175-2.140 (m, 1H), 2.267 (s, 3H), 2.103-2.035 (m, 1H); m/z: calcd. for $C_{29}H_{27}Cl_2N_3O_2$: 520.45; found [M+H$^+$]: 520.03; 521.96.

Example 20

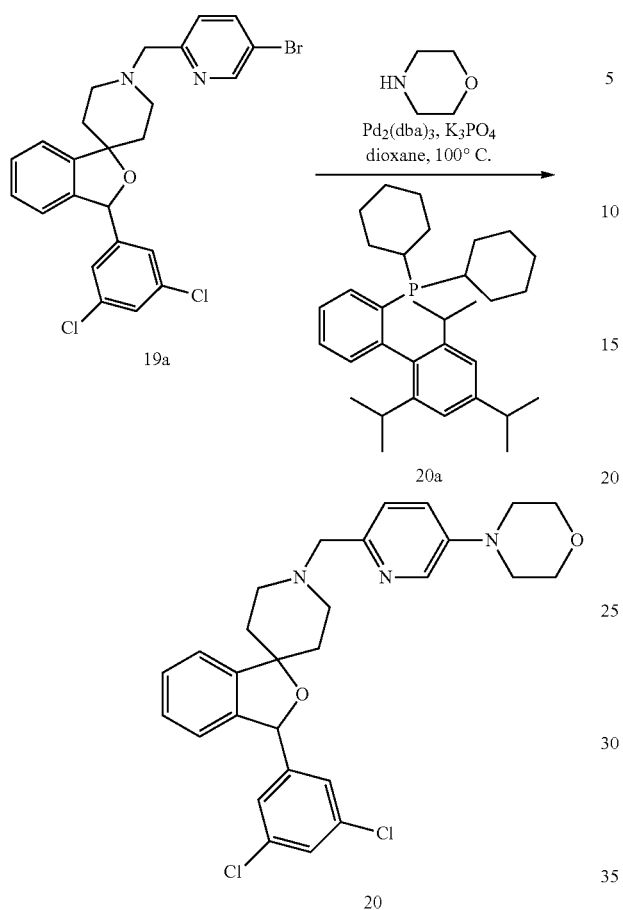

A mixture of 19a (20 mg, 0.040 mmol), morpholine (13.92 mg, 0.16 mmol), K$_3$PO$_4$ (17 mg, 0.080 mmol), Pd$_2$(dba)$_3$ (3.63 mg, 0.004 mmol), and 20a (5.67 mg, 0.012 mmol) in dioxane (1 mL) was heated at 100° C. for 18 h. To the reaction mixture was added water (1 mL) and ethyl acetate (3 mL). The organic phase was separated and concentrated. The resulting residue was purified on RP-HPLC using 10-100% acetonitrile (0.1% formic acid) to give 20 as the formic acid salt. $^1$HNMR (DMSO-d$_6$, 500 MHz) δ ppm 8.17 (d, J=2.4 Hz, 1H); 7.53 (t, J=1.8 Hz, 1H); 7.38 (d, J=1.8 Hz, 2H); 7.31 (m, 4H); 7.23 (dt, J=7.8; 1.2 Hz, 1H); 7.02 (d, J=7.8 Hz, 1H); 6.14 (s, 1H); 3.71 (t, J=4.8 Hz, 4H); 3.53 (s, 2H); 3.30 (m, overlap with H$_2$O, 1H); 3.10 (t, J=4.8 Hz, 4H); 2.79 (m, 1H); 2.73 (m, 1H); 2.39 (m, 1H); 2.17 (m, 1H); 1.83 (m, 1H); 1.83 (m, 1H); 1.65 (m, 1H); m/z for C$_{28}$H$_{29}$Cl$_2$N$_3$O$_2$, calc. 510.45; found [M+H$^+$]: 510.2; 512.2.

Example 21

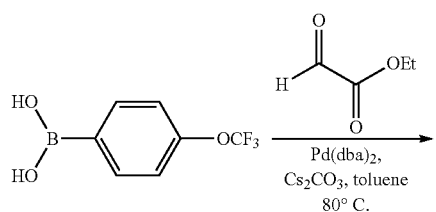

Step 1: A solution of 4-trifluoromethoxyphenylboronic acid (3.12 g, 15.13 mmol), ethyl glyoxalate (2 mL, 10.09 mmol, 50% in toluene), 2-(di-tert-butylphosphino)biphenyl (0.151 g, 0.504 mmol), tris(dibenzylideneacetone)dipalladium (0) (0.115, 0.126), and Cs$_2$CO$_3$ (3.29 g, 10.09 mmol) in toluene (30 mL) was heated at 80° C. under nitrogen for 24 h. The reaction mixture was partitioned between ethyl acetate (200 mL) and water (200 mL). The organic phase was washed with sat. NaHCO$_3$, dried over Na$_2$SO$_4$, and concentrated. The resulting residue was purified on silica gel using 10-40% ethyl acetate/hexanes to give 21a as an oil.

Step 2: Compound 21a (1.07 g, 4.05 mmol) was treated with thionyl chloride (3 mL, 40 mmol) at it for 16 h. After removing the volatiles, the residue was dissolved in ethyl acetate (200 mL) and washed with sat. NaHCO$_3$ (200 mL), dried over Na$_2$SO$_4$, and concentrated to give 21b as light orange oil.

Step 3: To a solution of 21b (1.07 g, 3.79 mmol) in acetonitrile (30 mL) at 0° C. was added 3c (1.142 g, 3.41 mmol) in one portion, and DMA (1.322, 7.57 mmol) dropwise. The resulting solution was stirred at it for 64 h. After removing the volatiles, the residue was dissolved in DCM (200 mL), washed with sat. NaHCO$_3$ (200 mL), dried over Na$_2$SO$_4$, and concentrated. The resulting residue was purified on silica gel using 10-40% ethyl acetate/hexanes to give the more polar mixture of two diastereomers 21c.

Step 4: To a solution of 21c (17 mg, 0.029 mmol) in acetic acid (1 mL) was added hydrochloric acid (11a, 5N), and the resulting solution was heated at 80° C. for 48 h. After removing the volatiles, the residue was purified on RP-HPLC using 20-80% acetonitrile (0.05% TFA) to give 21 as the TFA salt. $^1$HNMR (acetonitrile-d$_3$, 500 MHz) δ=8.554-8.544 (dd, J=4.9 Hz, 1H), 7.743-7.726 (dd, J=8.7 Hz, 2H), 7.542-7.527 (dd, J=7.7 Hz, 1H), 7.463-7.455 (m, 1H), 7.411-7.395 (m, 2H), 7.360-7.310 (m, 3H), 6.200 (s, 1H), 5.079 (s, 1H), 3.840-3.804 (m, 1H), 3.491-3.487 (m, 1H), 3.350-3.251 (m, 2H), 2.781-2.724 (m, 1H), 2.250-2.380 (m, 1H), 2.097-2.062 (m, 2H); calcd. for C$_{26}$H$_{21}$Cl$_2$F$_3$N$_2$O$_4$: 553.357; found [M+H$^+$]: 553.25; 555.21.

Example 22

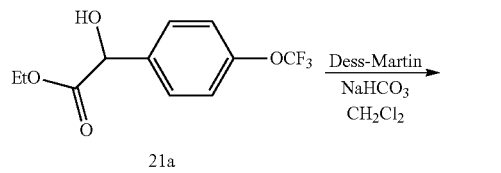

21a

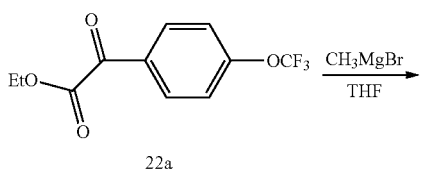

22a

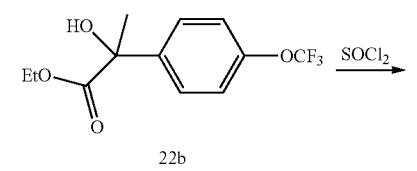

22b

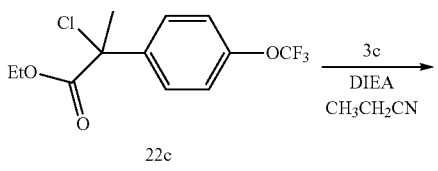

22c

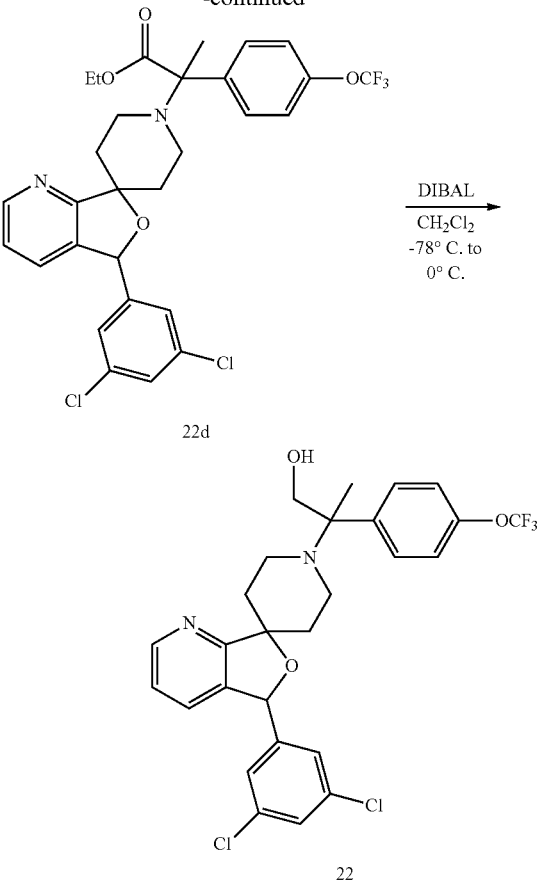

22d

22

Step 1: To a solution of 21a (1.65 g, 6.25 mmol) in DCM (40 mL) at 0° C. was added sodium bicarbonate (0.525 g, 6.25 mmol) and Dess-Martin periodinane (3.97 g, 9.37 mmol). The resulting mixture was stirred at rt for 3 h. After removing the volatiles, the residue was purified on silica gel using 10% ethyl acetate to give 22a.

Step 2: To a solution of 22a (300 mg, 1.144 mmol) in THF (8 mL) at −78° C. was added methyl magnesium bromide (420 mL, 1.259 mmol, 3M). The resulting solution was stirred from −78° C. to rt for 16 h, and then quenched with sat. ammonium chloride (50 mL) before extracting with EtOAc (2×100 mL). The combined organic phases were dried over Na$_2$SO$_4$, and concentrated to give 22b.

Step 3: Compound 22b (70 mg, 0.252 mmol) was treated with thionyl chloride (1 L) at rt for 16 h. The volatiles were evaporated under vacuum to give compound 22c.

Step 4: A solution of 22c, 3c, and DIEA (0.044 mL, 0.25 mmol) in propionitrile (2 mL) was heated at 95° C. for 16 h. The mixture was then purified on RP-HPLC using 10-100% acetonitrile (0.1% TFA). After removing the volatiles, the aqueous phase was basified with sat. NaHCO$_3$ (50 mL), and the mixture was extracted with DCM (2×50 mL). The combined organic phases were dried over Na$_2$SO$_4$, and concentrated under vacuum to give 22d.

Step 5: To a solution of 22d (35 mg, 0.059 mmol) in DCM (10 mL) was added DIBAL-H (0.235 mL, 0.235 mmol, 1M) at −78° C. The resulting solution was stirred at 0° C. for 30 min before quenching with methanol (1 mL), followed by the addition of 10% potassium tartrate (20 mL) for 1 h. The organic phase was dried over Na$_2$SO$_4$, and concentrated. The resulting residue was purified on RP-HPLC using 10-100% acetonitrile (0.1% TFA) to give 22, $^1$HNMR (acetonitrile-d$_3$, 500 MHz), δ=9.56 (broad, 1H), 8.554-8.545 (dd, J=4.7 Hz, 1H), 7.527-7.521 (m, 1H), 7.480-7.431 (m, 2H), 7.382 (s, 2H), 7.322-7.307 (m, 3H), 6.202 (s, 1H), 3.825-3.819 (m, 2H), 2.65-2.56 (m, 2H), 2.38-2.23 (m, 2H), 2.25-2.22 (m, 2H), 1.99-1.97 (m, 2H), 1.958 (s, 3H); m/z: calcd. for C$_{27}$H$_{25}$Cl$_2$F$_3$N$_2$O$_3$: 553.400; found [M+H$^+$]: 553.12, 555.01.

Example 23

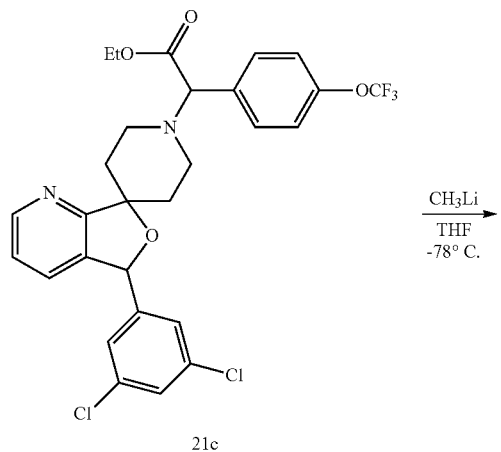

21c

To a solution of 21c (120 mg, 0.206 mmol) in THF (4 mL) at −78° C. was added methyllithium (0.206 mL, 0.619 mmol). The resulting solution was stirred at rt for 16 h. Then the reaction was quenched with sat. NaHCO$_3$, extracted with DCM, dried over Na$_2$SO$_4$, and concentrated. The resulting residue was purified on a TLC plate using 5% MeOH/CH$_2$Cl$_2$ to give 23. $^1$HNMR (chloroform-d, 500 MHz) δ=8.586 (m, 1H), 7.468-7.452 (dd, J=8.1 Hz, 2H), 7.338-7.313 (m, 3H), 7.216-7.167 (m, 4H), 5.997 (s, 1H), 3.580-3.534 (m, 1H), 3.294-3.235 (m, 1H), 2.98-2.85 (m, 2H), 2.58-2.47 (m, 1H), 2.200 (s, 6H), 2.150-2.036 (m, 2H), 1.881-1.631 (m, 2H); m/z: calcd. for C$_{28}$H$_{27}$Cl$_2$F$_3$N$_2$O$_3$: 567.427; found [M+H$^+$]: 567.12, 569.01.

Example 24

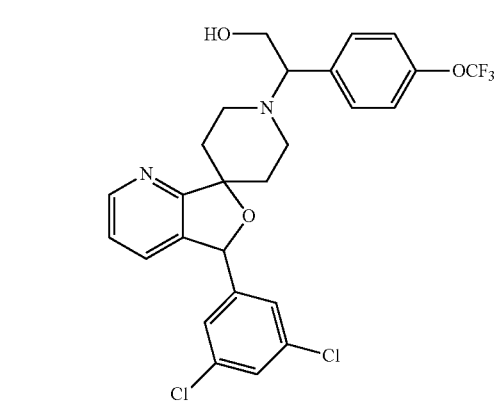

21c

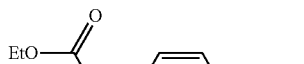

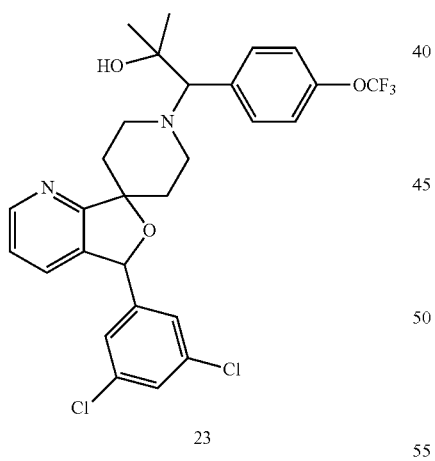

24

To a solution of 21c (50 mg, 0.086 mmol) in DCM (4 mL) was added DIBAL-H (0.258 mL, 0.258 mmol, 1M) at −78° C., and the resulting solution was stirred from −78° C. to rt for 4 h. The reaction was treated with 10% potassium tartrate (20 mL) for 1 h. The organic phase was separated, dried over Na$_2$SO$_4$, and concentrated. The resulting residue was purified on RP-HPLC using 10-100% acetonitrile (0.1% TFA) to give 24 as the TFA salt. $^1$HNMR (acetonitrile-d$_3$, 500 MHz), δ=8.618-8.582 (m, 1H), 7.731-7.599 (m, 3H), 7.498-7.387 (m, 4H), 7.352 (s, 1H), 6.202 (s, 1H), 4.175-4.123 (m, 2H), 3.6 (m, 1H, overlapping with water), 2.73-2.64 (m, 2H), 2.52-2.43 (m, 2H), 2.14-2.08 (m, 2H), 2.02-1.90 (m, 2H); m/z: calcd. for C$_{26}$H$_{23}$Cl$_2$F$_3$N$_2$O$_3$: 539.374; found [M+H$^+$]: 539.17; 541.19.

TABLE 1
Examples 25-55 were prepared according to the procedures of Examples 1, 3, and 4.
| Example | Structure | Mass Spec data |
|---|---|---|
| 25 | 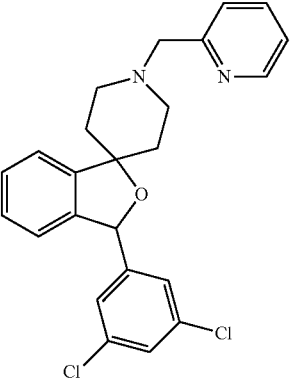 [SMILES: Clc1cc(Cl)cc(C2OC3(CCN(Cc4ccccn4)CC3)c3ccccc32)c1] | m/z for $C_{24}H_{22}Cl_2N_2O$, calc. 425.35; found [M + H$^+$]: 425.01; 426.91 |
| 26 | 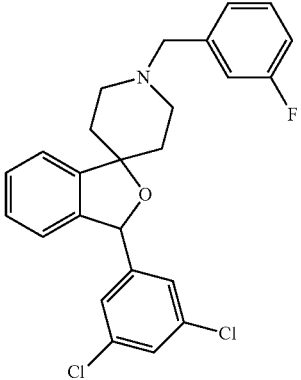 [SMILES: Fc1cccc(CN2CCC3(CC2)OC(c2cc(Cl)cc(Cl)c2)c2ccccc23)c1] | m/z for $C_{25}H_{22}Cl_2FNO$, calc. 442.35; found [M + H$^+$]: 442.01; 443.90 |
| 27 | 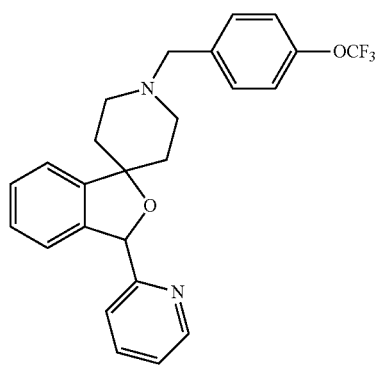 [SMILES: FC(F)(F)Oc1ccc(CN2CCC3(CC2)OC(c2ccccn2)c2ccccc23)cc1] | m/z for $C_{25}H_{23}F_3N_2O_2$, calc. 440.46; found [M + H$^+$]: 440.96 |
| 28 | 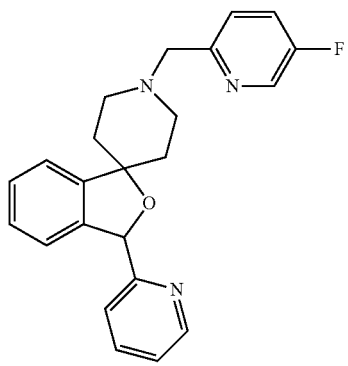 [SMILES: Fc1ccc(CN2CCC3(CC2)OC(c2ccccn2)c2ccccc23)nc1] | m/z for $C_{23}H_{22}FN_3O$, calc. 375.44; found [M + H$^+$]: 376.04 |

TABLE 1-continued
Examples 25-55 were prepared according to the procedures of Examples 1, 3, and 4.
| Example | Structure | Mass Spec data |
|---|---|---|
| 29 | 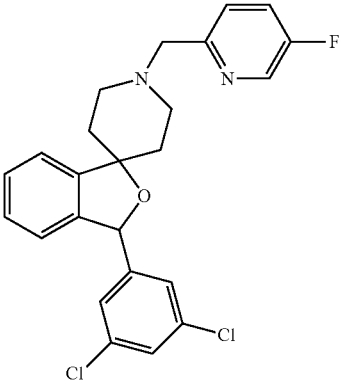 [SMILES: Fc1ccc(CN2CCC3(CC2)OC(c2cc(Cl)cc(Cl)c2)c2ccccc23)nc1] | m/z: calcd. for $C_{24}H_{21}Cl_2N_3O$; 443.34; found [M + H⁺]: 442.95 (100%), 444.87 (70%). |
| 30 | 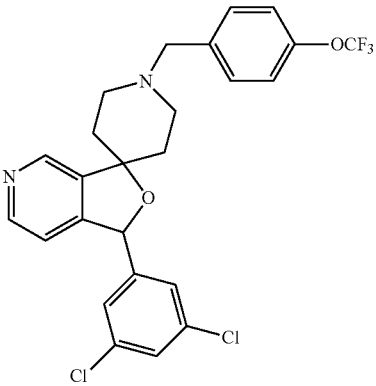 [SMILES: FC(F)(F)Oc1ccc(CN2CCC3(CC2)OC(c2cc(Cl)cc(Cl)c2)c2ccncc23)cc1] | m/z for $C_{25}H_{21}Cl_2F_3N_2O_2$, calc. 509.35; found [M + H⁺]: 508.96; 510.95 |
| 31 | 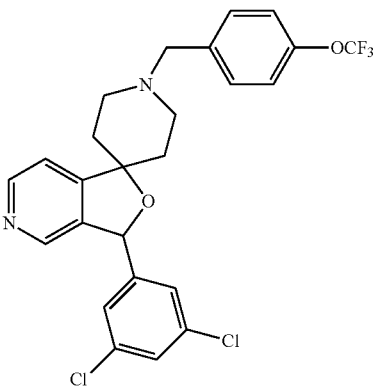 [SMILES: FC(F)(F)Oc1ccc(CN2CCC3(CC2)OC(c2cc(Cl)cc(Cl)c2)c2cnccc23)cc1] | m/z for $C_{25}H_{21}Cl_2F_3N_2O_2$, calc. 509.35; found [M + H⁺]: 508.95; 510.85 |
| 32 | 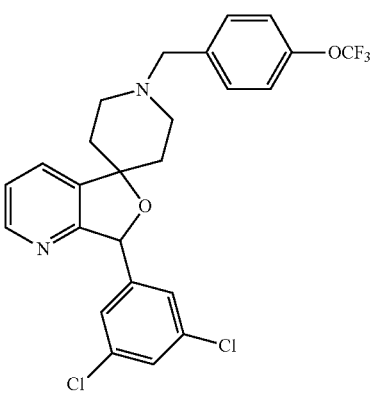 [SMILES: FC(F)(F)Oc1ccc(CN2CCC3(CC2)OC(c2cc(Cl)cc(Cl)c2)c2ncccc23)cc1] | m/z for $C_{25}H_{21}Cl_2F_3N_2O_2$, calc. 509.35; found [M + H⁺]: 508.95; 510.84 |

TABLE 1-continued
Examples 25-55 were prepared according to the procedures of Examples 1, 3, and 4.
| Example | Structure | Mass Spec data |
|---|---|---|
| 33 | 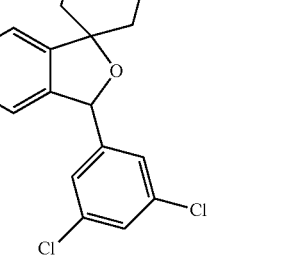 | m/z for $C_{23}H_{20}Cl_2FN_3O$, calc. 444.33; found [M + H$^+$]: 443.97; 445.92 |
| 34 | 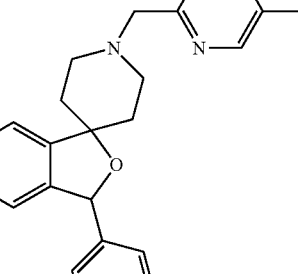 | m/z for $C_{23}H_{20}Cl_2FN_3O$, calc. 444.33; found [M + H$^+$]: 443.96; 445.86 |
| 35 | 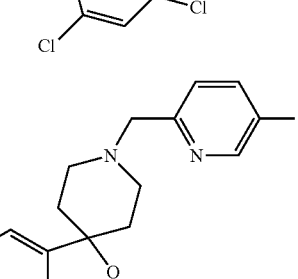 | m/z for $C_{23}H_{20}Cl_2FN_3O$, calc. 444.33; found [M + H$^+$]: 443.96; 445.87 |
| 36 | 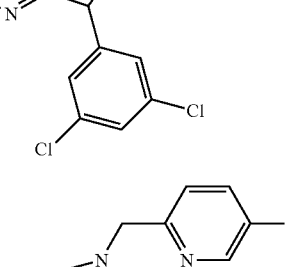 | m/z for $C_{25}H_{21}Cl_2F_3N_2O$, calc. 493.35; found [M + H$^+$]: 492.92; 494.84 |

TABLE 1-continued
Examples 25-55 were prepared according to the procedures of Examples 1, 3, and 4.
| Example | Structure | Mass Spec data |
|---|---|---|
| 37 | 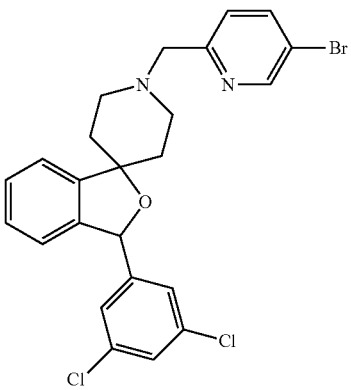 [SMILES: Clc1cc(Cl)cc(C2OC3(CCN(Cc4ccc(Br)cn4)CC3)c3ccccc32)c1] | m/z for $C_{24}H_{21}BrCl_2N_2O$, calc. 504.25; found [M + H$^+$]: 502.92; 504.91; 506.91 |
| 38 | 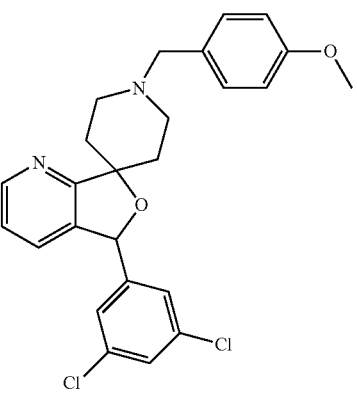 [SMILES: COc1ccc(CN2CCC3(CC2)OC(c2cc(Cl)cc(Cl)c2)c2cccnc23)cc1] | m/z for $C_{25}H_{24}Cl_2N_2O_2$, calc. 455.376; found [M + H$^+$]: 455.21; 457.21 |
| 39 | 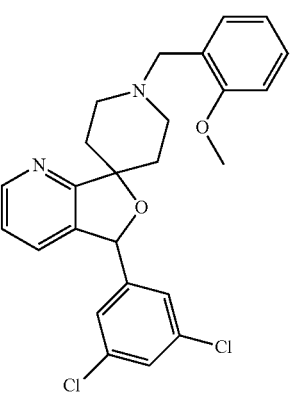 [SMILES: COc1ccccc1CN1CCC2(CC1)OC(c1cc(Cl)cc(Cl)c1)c1cccnc12] | m/z for $C_{25}H_{24}Cl_2N_2O_2$, calc. 455.376; found [M + H$^+$]: 455.16; 457.15 |
| 40 | 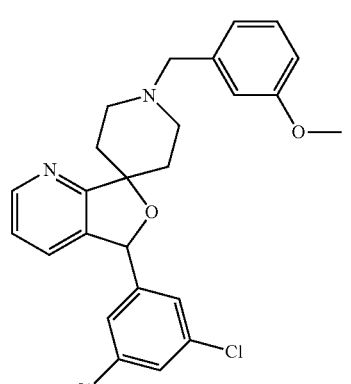 | m/z for $C_{25}H_{24}Cl_2N_2O_2$, calc. 455.376; found [M + H$^+$]: 455.20; 457.16 |

TABLE 1-continued

Examples 25-55 were prepared according to the procedures of Examples 1, 3, and 4.

| Example | Structure | Mass Spec data |
|---|---|---|
| 41 | 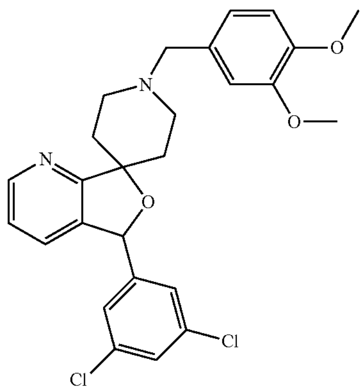 [SMILES: COc1ccc(CN2CCC3(CC2)OC(c2cc(Cl)cc(Cl)c2)c2cccnc23)cc1OC] | m/z for $C_{26}H_{26}Cl_2N_2O_3$, calc. 485.402; found [M + H$^+$]: 485.21; 487.21 |
| 42 | 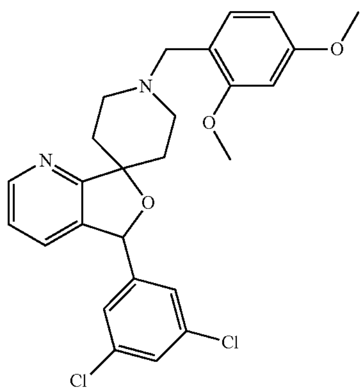 [SMILES: COc1ccc(CN2CCC3(CC2)OC(c2cc(Cl)cc(Cl)c2)c2cccnc23)c(OC)c1] | m/z for $C_{26}H_{26}Cl_2N_2O_3$, calc. 485.402; found [M + H$^+$]: 485.13; 487.09 |
| 43 | 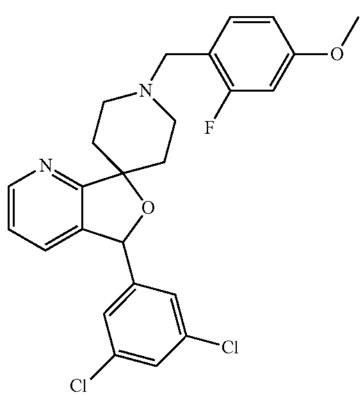 [SMILES: COc1ccc(CN2CCC3(CC2)OC(c2cc(Cl)cc(Cl)c2)c2cccnc23)c(F)c1] | m/z for $C_{25}H_{23}Cl_2FN_2O_2$, calc. 473.367; found [M + H$^+$]: 473.12; 475.04 |
| 44 | 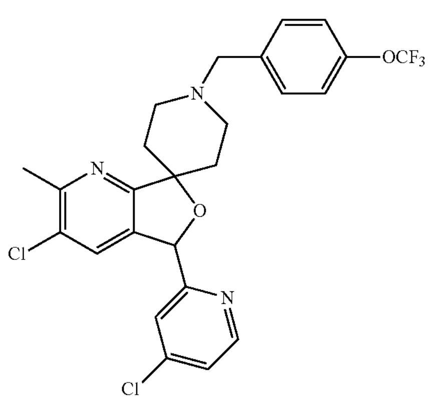 [SMILES: Cc1nc2c(cc1Cl)C(c1cc(Cl)ccn1)OC21CCN(Cc2ccc(OC(F)(F)F)cc2)CC1] | m/z for C25H22Cl2F3N3O2, calc. 524.36; found [M + H$^+$]: 524.04; 526.02 |

TABLE 1-continued
Examples 25-55 were prepared according to the procedures of Examples 1, 3, and 4.
| Example | Structure | Mass Spec data |
|---|---|---|
| 45 | 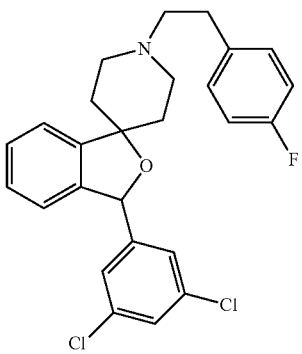 [SMILES: Fc1ccc(CCN2CCC3(CC2)OC(c2cc(Cl)cc(Cl)c2)c2ccccc23)cc1] | m/z for $C_{26}H_{24}Cl_2FNO$, calc. 456.38; found [M + H$^+$]: 456.03; 457.95 |
| 46 | 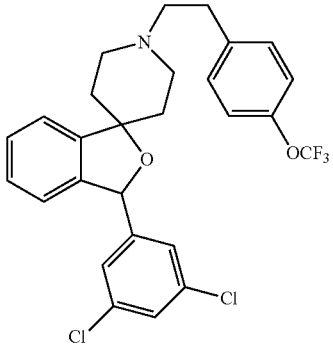 [SMILES: FC(F)(F)Oc1ccc(CCN2CCC3(CC2)OC(c2cc(Cl)cc(Cl)c2)c2ccccc23)cc1] | m/z for $C_{27}H_{24}Cl_2F_3NO_2$, calc. 522.39; found [M + H$^+$]: 522.00; 523.92 |
| 47 | 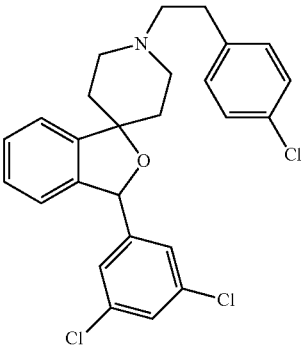 [SMILES: Clc1ccc(CCN2CCC3(CC2)OC(c2cc(Cl)cc(Cl)c2)c2ccccc23)cc1] | m/z for $C_{26}H_{24}Cl_3NO$, calc. 472.83; found [M + H$^+$]: 471.93; 473.94; 475.95 |
| 48 | 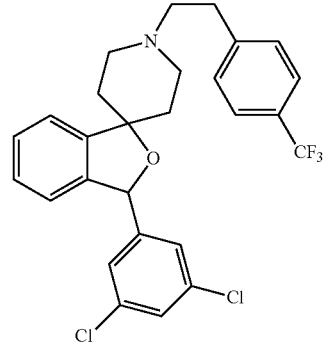 [SMILES: FC(F)(F)c1ccc(CCN2CCC3(CC2)OC(c2cc(Cl)cc(Cl)c2)c2ccccc23)cc1] | m/z for $C_{27}H_{24}Cl_2F_3NO$, calc. 506.39; found [M + H$^+$]: 506.02; 507.96 |

TABLE 1-continued
Examples 25-55 were prepared according to the procedures of Examples 1, 3, and 4.
| Example | Structure | Mass Spec data |
|---|---|---|
| 49 | 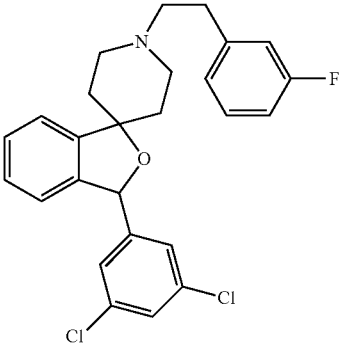 [SMILES: Fc1cccc(CCN2CCC3(CC2)OC(c2cc(Cl)cc(Cl)c2)c2ccccc23)c1] | m/z for $C_{26}H_{24}Cl_2FNO$, calc. 456.38; found [M + H$^+$]: 456.03; 457.97 |
| 50 | 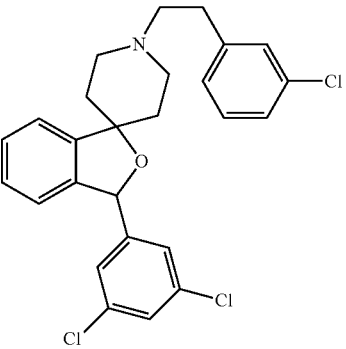 [SMILES: Clc1cccc(CCN2CCC3(CC2)OC(c2cc(Cl)cc(Cl)c2)c2ccccc23)c1] | m/z for $C_{26}H_{24}Cl_3NO$, calc. 472.83; found [M + H$^+$]: 471.93; 473.94; 475.96 |
| 51 | 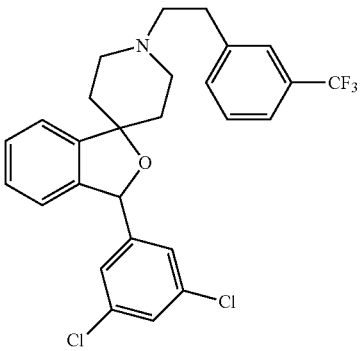 [SMILES: FC(F)(F)c1cccc(CCN2CCC3(CC2)OC(c2cc(Cl)cc(Cl)c2)c2ccccc23)c1] | m/z for $C_{27}H_{24}Cl_2F_3NO$, calc. 506.39; found [M + H$^+$]: 505.97; 507.93 |
| 52 | 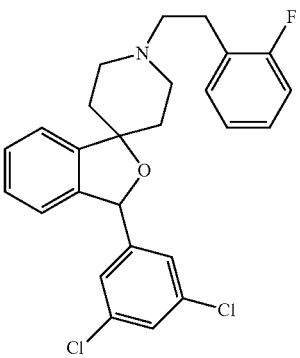 [SMILES: Fc1ccccc1CCN1CCC2(CC1)OC(c1cc(Cl)cc(Cl)c1)c1ccccc12] | m/z for $C_{26}H_{24}Cl_2FNO$, calc. 456.38; found [M + H$^+$]: 455.98; 457.90 |

TABLE 1-continued

Examples 25-55 were prepared according to the procedures of Examples 1, 3, and 4.

| Example | Structure | Mass Spec data |
|---|---|---|
| 53 | 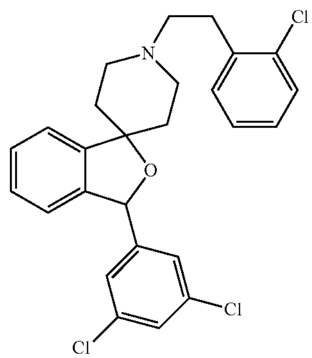 [SMILES: Clc1cc(Cl)cc(C2OC3(CCN(CCc4ccccc4Cl)CC3)c3ccccc32)c1] | m/z for $C_{26}H_{24}Cl_3NO$, calc. 472.83; found [M + H$^+$]: 471.87; 473.87; 475.88 |
| 54 | 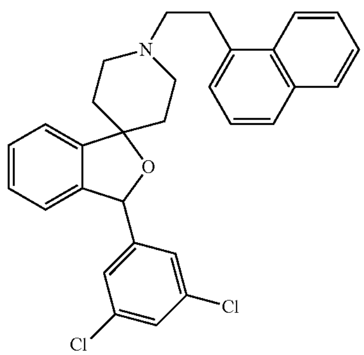 [SMILES: Clc1cc(Cl)cc(C2OC3(CCN(CCc4cccc5ccccc45)CC3)c3ccccc32)c1] | m/z for $C_{30}H_{27}Cl_2NO$, calc. 488.45; found [M + H$^+$]: 488.04; 490.00 |
| 55 | 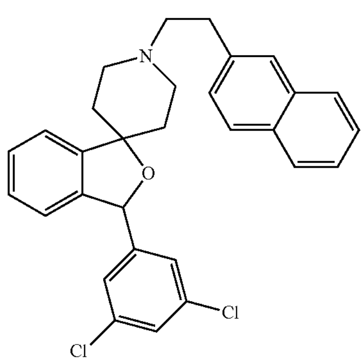 [SMILES: Clc1cc(Cl)cc(C2OC3(CCN(CCc4ccc5ccccc5c4)CC3)c3ccccc32)c1] | m/z for $C_{30}H_{27}Cl_2NO$, calc. 488.45; found [M + H$^+$]: 488.04; 490.00 |

TABLE 2

Examples 56-65 were prepared according to the procedure of Example 19.

| Example | Structure | Mass Spec data |
|---|---|---|
| 56 | 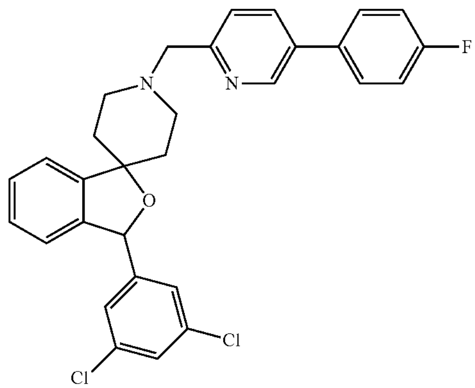 [SMILES: Fc1ccc(-c2ccc(CN3CCC4(CC3)OC(c3cc(Cl)cc(Cl)c3)c3ccccc34)nc2)cc1] | m/z for $C_{30}H_{25}Cl_2FN_2O$, calc. 519.44; found [M + H$^+$]: 519.2; 521.2 |
| 57 | 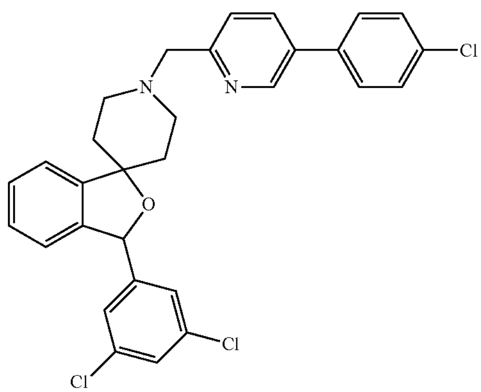 [SMILES: Clc1ccc(-c2ccc(CN3CCC4(CC3)OC(c3cc(Cl)cc(Cl)c3)c3ccccc34)nc2)cc1] | m/z for $C_{30}H_{25}Cl_3N_2O$, calc. 535.89; found [M + H$^+$]: 535.2; 538.2 |
| 58 | 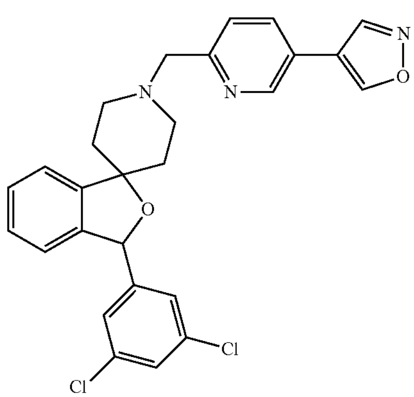 [SMILES: Clc1cc(Cl)cc(C2OC3(CCN(Cc4ccc(-c5cnoc5)cn4)CC3)c3ccccc32)c1] | m/z for $C_{27}H_{23}Cl_2N_3O_2$, calc. 492.40; found [M + H$^+$]: 492.05; 494.05 |
| 59 | 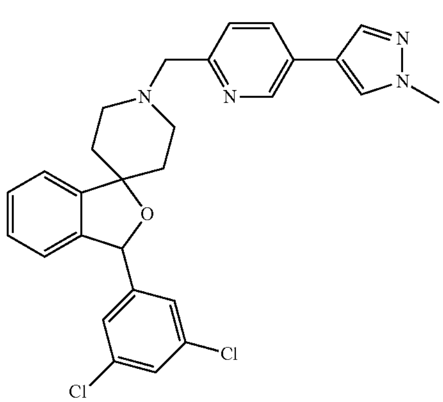 [SMILES: Cn1cc(-c2ccc(CN3CCC4(CC3)OC(c3cc(Cl)cc(Cl)c3)c3ccccc34)nc2)cn1] | m/z for $C_{28}H_{26}Cl_2N_4O$, calc. 505.44; found [M + H$^+$]: 505.10; 507.07 |

TABLE 2-continued
Examples 56-65 were prepared according to the procedure of Example 19.
| Example | Structure | Mass Spec data |
|---|---|---|
| 60 | 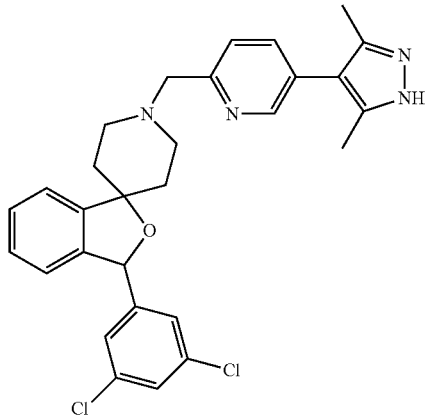 [SMILES: Cc1n[nH]c(C)c1-c1ccc(CN2CCC3(CC2)OC(c2cc(Cl)cc(Cl)c2)c2ccccc23)nc1] | m/z for $C_{29}H_{28}Cl_2N_4O$, calc. 519.46; found [M + H$^+$]: 519.14; 521.11 |
| 61 | 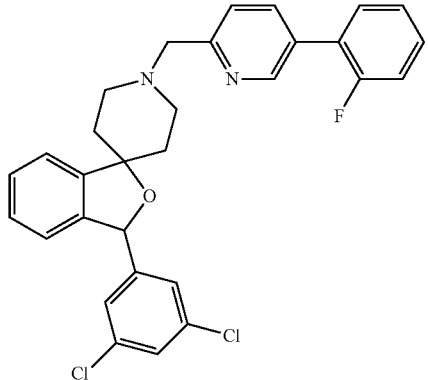 [SMILES: Fc1ccccc1-c1ccc(CN2CCC3(CC2)OC(c2cc(Cl)cc(Cl)c2)c2ccccc23)nc1] | m/z for $C_{30}H_{25}Cl_2FN_2O$, calc. 519.44; found [M + H$^+$]: 519.2; 521.2 |
| 62 | 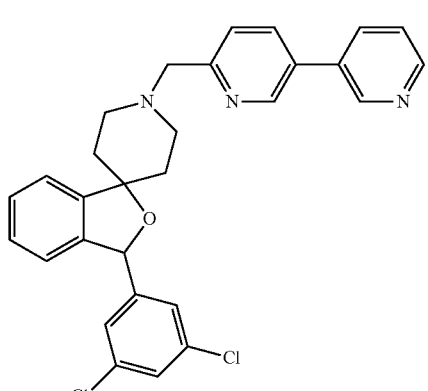 | m/z for $C_{29}H_{25}Cl_2N_3O$, calc. 502.43; found [M + H$^+$]: 502.2; 504.2 |

TABLE 2-continued

Examples 56-65 were prepared according to the procedure of Example 19.

| Example | Structure | Mass Spec data |
| --- | --- | --- |
| 63 | 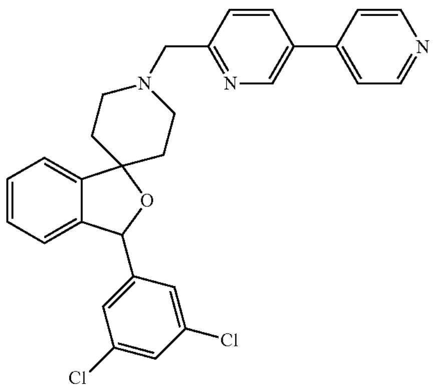 [SMILES: Clc1cc(Cl)cc(C2OC3(CCN(Cc4ccc(-c5ccncc5)cn4)CC3)c3ccccc32)c1] | m/z for $C_{29}H_{25}Cl_2N_3O$, calc. 502.43; found [M + H$^+$]: 502.2; 504.2 |
| 64 | 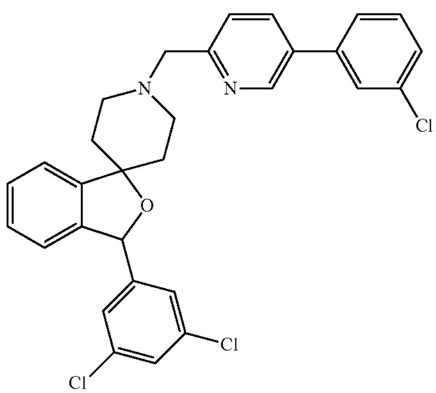 [SMILES: Clc1cccc(-c2ccc(CN3CCC4(CC3)OC(c3cc(Cl)cc(Cl)c3)c3ccccc34)nc2)c1] | m/z for $C_{30}H_{25}Cl_3N_2O$, calc. 535.89; found [M + H$^+$]: 535.1; 538.1 |
| 65 | 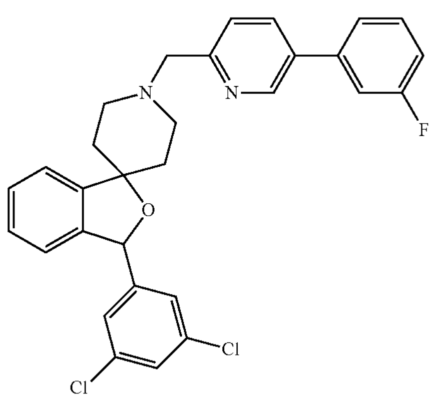 [SMILES: Fc1cccc(-c2ccc(CN3CCC4(CC3)OC(c3cc(Cl)cc(Cl)c3)c3ccccc34)nc2)c1] | m/z for $C_{30}H_{25}Cl_2FN_2O$, calc. 519.44; found [M + H$^+$]: 519.2; 521.2 |

TABLE 3

Examples 66-69 were prepared according to the procedure of Example 20.

| Example | Structure | Mass Spec data |
|---|---|---|
| 66 | 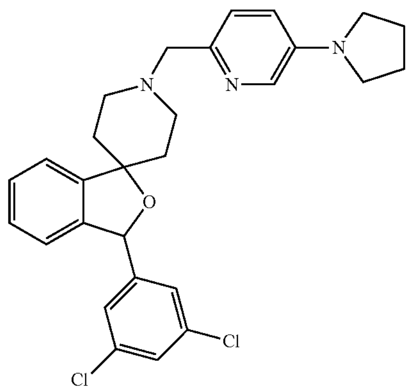 [SMILES: Clc1cc(Cl)cc(C2OC3(CCN(Cc4ccc(N5CCCC5)cn4)CC3)c3ccccc32)c1] | m/z for $C_{28}H_{29}Cl_2N_3O$, calc. 494.46; found [M + H$^+$]: 494.2; 496.2 |
| 67 | 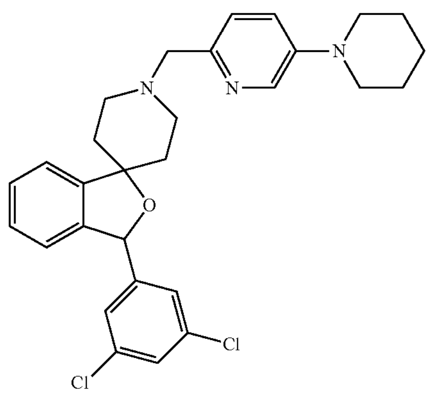 [SMILES: Clc1cc(Cl)cc(C2OC3(CCN(Cc4ccc(N5CCCCC5)cn4)CC3)c3ccccc32)c1] | m/z for $C_{29}H_{31}Cl_2N_3O$, calc. 508.48; found [M + H$^+$]: 508.2; 510.2 |
| 68 | 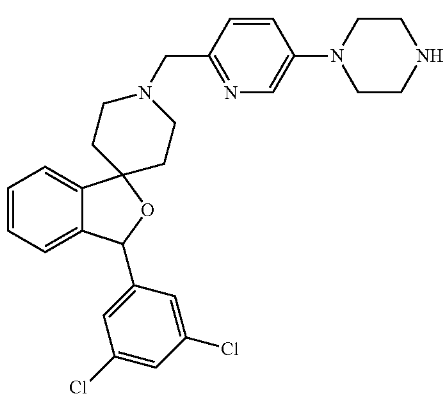 [SMILES: Clc1cc(Cl)cc(C2OC3(CCN(Cc4ccc(N5CCNCC5)cn4)CC3)c3ccccc32)c1] | m/z for $C_{28}H_{30}Cl_2N_4O$, calc. 509.47; found [M + H$^+$]: 509.2; 511.2 |
| 69 | 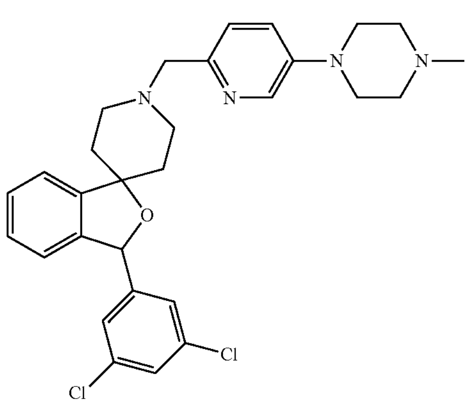 [SMILES: CN1CCN(c2ccc(CN3CCC4(CC3)OC(c3cc(Cl)cc(Cl)c3)c3ccccc34)nc2)CC1] | m/z: calcd. for $C_{29}H_{32}Cl_2N_4O$, calc. 523.47; found [M + H$^+$]: 523.2 (100%); 525.2 (70%). |

TABLE 4

Examples 70-80 were prepared according to the procedure of Example 18.

| Example | Structure | Mass Spec data |
|---------|-----------|----------------|
| 70 | 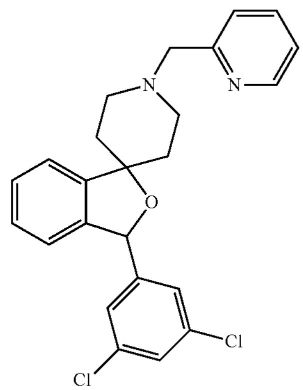 [SMILES: Clc1cc(Cl)cc(C2OC3(CCN(Cc4ccccn4)CC3)c3ccccc32)c1] | m/z for $C_{24}H_{22}Cl_2N_2O$, calc. 425.35; found [M + H$^+$]: 425.01; 426.91 |
| 71 | 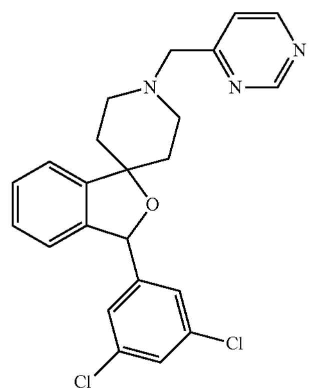 [SMILES: Clc1cc(Cl)cc(C2OC3(CCN(Cc4ccncn4)CC3)c3ccccc32)c1] | m/z for $C_{23}H_{21}Cl_2N_3O$, calc. 426.34; found [M + H$^+$]: 425.99; 427.92 |
| 72 | 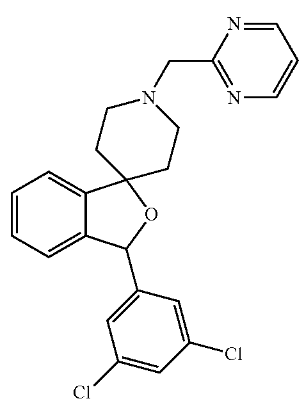 [SMILES: Clc1cc(Cl)cc(C2OC3(CCN(Cc4ncccn4)CC3)c3ccccc32)c1] | m/z for $C_{23}H_{21}Cl_2N_3O$, calc. 426.34; found [M + H$^+$]: 425.98; 427.90 |
| 73 | 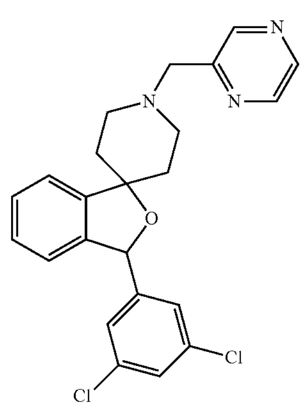 [SMILES: Clc1cc(Cl)cc(C2OC3(CCN(Cc4cnccn4)CC3)c3ccccc32)c1] | m/z for $C_{23}H_{21}Cl_2N_3O$, calc. 426.34; found [M + H$^+$]: 425.99; 427.91 |

TABLE 4-continued
Examples 70-80 were prepared according to the procedure of Example 18.
| Example | Structure | Mass Spec data |
| --- | --- | --- |
| 74 | 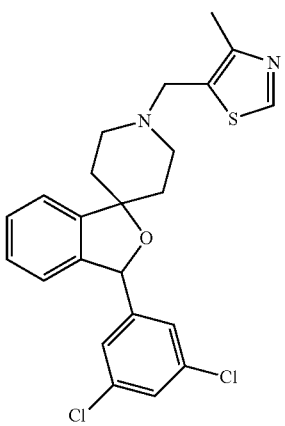 [SMILES: Cc1ncsc1CN1CCC2(CC1)OC(c1cc(Cl)cc(Cl)c1)c1ccccc12] | m/z for $C_{23}H_{22}Cl_2N_2OS$, calc. 445.40; found [M + H$^+$]: 444.94; 446.93 |
| 75 | 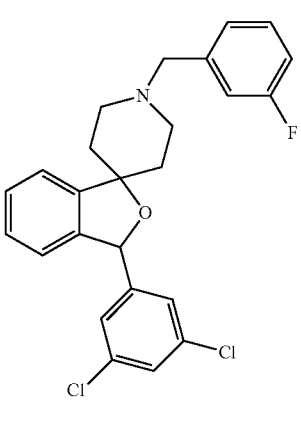 [SMILES: Fc1cccc(CN2CCC3(CC2)OC(c2cc(Cl)cc(Cl)c2)c2ccccc23)c1] | m/z for $C_{25}H_{22}Cl_2FNO$, calc. 442.35; found [M + H$^+$]: 442.01; 443.90 |
| 76 | 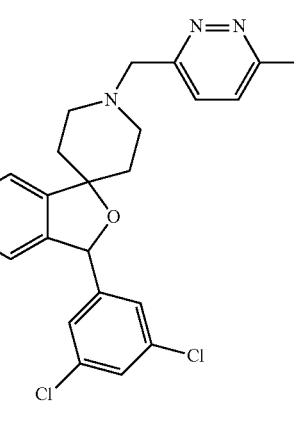 | m/z for $C_{23}H_{20}Cl_3N_3O$, calc. 460.78; found [M + H$^+$]: 459.92; 461.92 |

TABLE 4-continued
Examples 70-80 were prepared according to the procedure of Example 18.
| Example | Structure | Mass Spec data |
|---|---|---|
| 77 | 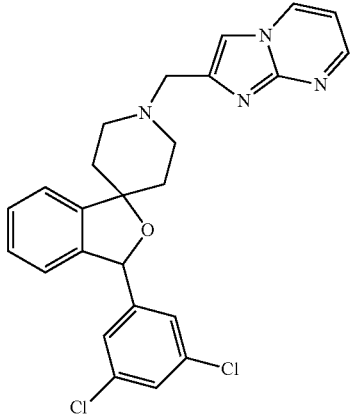 [SMILES: Clc1cc(Cl)cc(C2OC3(CCN(Cc4cn5cccnc5n4)CC3)c3ccccc32)c1] | m/z for $C_{25}H_{22}Cl_2N_4O$, calc. 465.37; found [M + H$^+$]: 465.03; 466.97 |
| 78 | 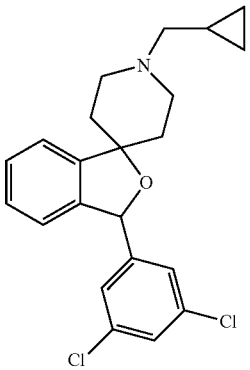 [SMILES: Clc1cc(Cl)cc(C2OC3(CCN(CC4CC4)CC3)c3ccccc32)c1] | m/z for $C_{22}H_{23}Cl_2NO$: cal. 388.33; found [M + H+]: 388.09; 390.07 |
| 79 | 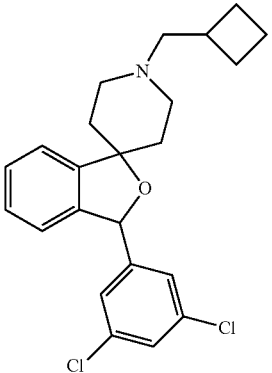 [SMILES: Clc1cc(Cl)cc(C2OC3(CCN(CC4CCC4)CC3)c3ccccc32)c1] | m/z for $C_{23}H_{25}Cl_2NO$: cal. 402.36; found [M + H+]: 402.14; 404.10 |
| 80 | 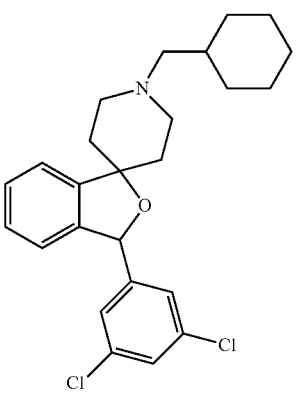 [SMILES: Clc1cc(Cl)cc(C2OC3(CCN(CC4CCCCC4)CC3)c3ccccc32)c1] | m/z for $C_{25}H_{29}Cl_2NO$: cal. 430.41; found [M + H+]: 430.17; 432.15 |

TABLE 5
Examples 81-86 were prepared according to the procedure of Examples 16 and 17.
| Example | Structure | Mass Spec data |
|---|---|---|
| 81 | 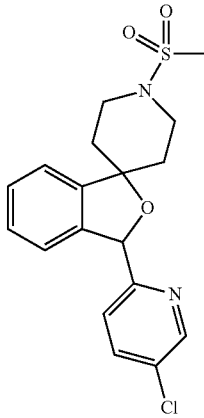 | m/z: calcd. for $C_{24}H_{20}ClF_3N_2O_4S$: 524.94; found [M + H$^+$]: 524.92; 526.90 (33%). |
| 82 | 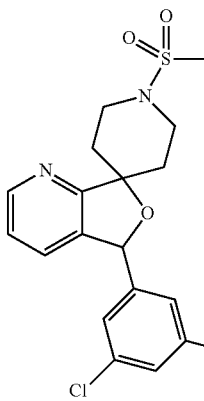 | m/z: calcd. for $C_{24}H_{19}Cl_2F_3N_2O_4S$: 559.38; found [M + H$^+$]: 558.96 (100%), 560.98 (70%). |
| 83 | 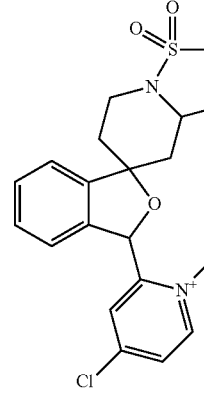 | m/z: calcd. for $C_{24}H_{21}ClF_3N_3O_4S$ : 539.954; found [M + H$^+$]: 555.0539.99 (100%), 541.91 (33%). |

TABLE 5-continued

Examples 81-86 were prepared according to the procedure of Examples 16 and 17.

| Example | Structure | Mass Spec data |
|---|---|---|
| 84 | 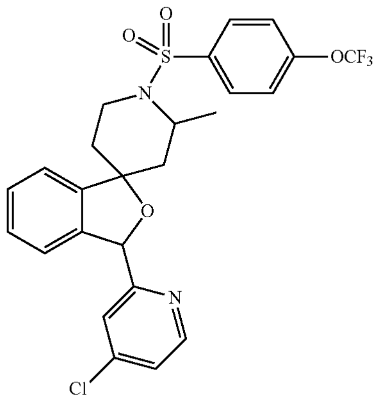 [SMILES: CC1CC2(CCN1S(=O)(=O)c1ccc(OC(F)(F)F)cc1)OC(c1cc(Cl)ccn1)c1ccccc12] | m/z: calcd. for $C_{25}H_{22}ClF_3N_2O_4S$: 538.966; found [M + H⁺]: 539.02 (100%), 540.89 (33%) |
| 85 | 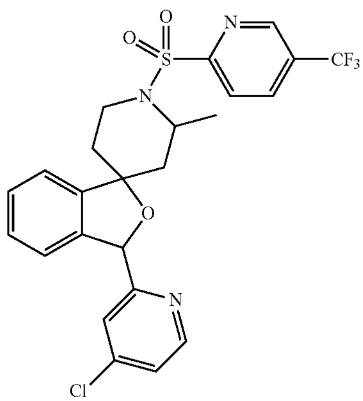 [SMILES: CC1CC2(CCN1S(=O)(=O)c1ccc(C(F)(F)F)cn1)OC(c1cc(Cl)ccn1)c1ccccc12] | m/z: calcd. for $C_{24}H_{21}ClF_3N_3O_3S$: 523.955; found [M + H⁺]: 524.02 (100%), 525.86 (33%). |
| 86 | 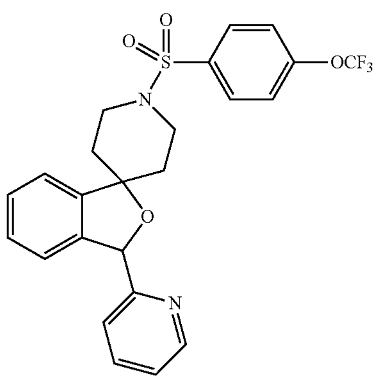 [SMILES: O=S(=O)(c1ccc(OC(F)(F)F)cc1)N1CCC2(CC1)OC(c1ccccn1)c1ccccc12] | m/z: calcd. for $C_{24}H_{21}F_3N_2O_4S$: 490.49; found [M + H⁺]: 490.96. |

The utility of the compounds in accordance with the present invention as inhibitors of prolylcarboxypeptidase (PRCP) enzyme activity may be demonstrated by the following assays:

Biological Example 1

Prolylcarboxypeptidase (PRCP) Enzyme Activity Assay

The potency of compounds of formula I against PrCP was determined by a fluorescence intensity kinetic assay measuring the $IC_{50}$ values of PrCP inhibitor test compounds. Recombinant human and mouse PrCP enzymes from CHO or HEK expression systems (with comparable results for HEK enzymes) were prepared in-house and used in the assay. The assay was run on a Perkin Elmer Envision 2103 plate reader using a 320 nm excitation filter and a 405 emission filter. The assay was performed using a Hamilton Star liquid handling workstation. The assay employed the internally quenched fluorescent substrate (1S)-1-carboxy-5-[(2,4-dinitrophenyl)amino]pentyl N-[(7-methoxy-2-oxo-2H-chromen-4-yl)acetyl]-L-alanyl-L-prolinate prepared in house.

The assay was run in a 384-well microtiter plate at 37° C. with a total volume of 50 uL. Final assay concentrations were 0.13 nM human PrCP (CHO) or 0.09 nM mouse PrCP (CHO) enzyme, 15 uM substrate and varying concentrations of inhibitor in buffer containing 10 mM NaOAc, 100 mM NaCl and 19.5 ug/mL BSA at pH 5.5. The assay also contained 2%

DMSO used to solubilize the substrate and inhibitor Inhibitors were prepared in 100% DMSO and serial diluted (in 100% DMSO) to generate 11 point titration curves. Either 39 uL of human or mouse PrCP enzyme was added to the wells of the assay plate, followed by a 1 uL addition of the serially diluted inhibitor and mixed three times using a 30 uL mix volume. The reaction was initiated by the addition of 10 uL substrate and mixed three times using a 30 uL mix volume. The reactions were monitored continuously over 25 min at 37° C. to obtain initial velocities. IC50 values were calculated by comparing the resulting rates of reaction of the inhibited and control initial velocities. For the more potent compounds, a modified dilution series at a lower concentration range was used to more accurately determine the potency.

The enzymes were diluted in a mixture of 10 mM NaOAc (pH 5.5)/100 mM NaCl buffer containing 25 ug/mL bovine serum albumin that had been warmed to 37° C. in a water bath. The PrCP inhibitor test compounds were plated in 100% DMSO with a highest concentration of 500 uM. There were 12 dilution points for each compound tested including a blank with DMSO only. The test compounds from the source titration plate were transferred into the assay reaction plate at a 1:50 dilution using the Hamilton Star workstation and mixed, resulting in a final concentration for the test compounds in the range of 10,000 to 0.066 nM. Likewise, two control compounds were similarly titrated and included in each assay, with final starting concentrations starting at 10,000 nM and 200 nM, respectively. The reaction was initiated by the addition of 75 uM of the (1S)-1-carboxy-5-[(2,4-dinitrophenyl)amino]pentyl N-[(7-methoxy-2-oxo-2H-chromen-4-yl)acetyl]-L-alanyl-L-prolinate substrate, which was diluted in a mixture of 10 mM NaOAc (pH 5.5)/100 mM NaCl that had been warmed to 37° C. in a water bath, dispensed using the Hamilton Star workstation and mixed. The substrate was solubilized in 100% DMSO prior to dilution into the assay. The final assay concentrations in the 50 uL reactions were 15 uM of (1S)-1-carboxy-5-[(2,4-dinitrophenyl)amino]pentyl N-[(7-methoxy-2-oxo-2H-chromen-4-yl)acetyl]-L-alanyl-L-prolinate substrate, 0.13 nM Human PrCP (CHO) or 0.09 nM Mouse PrCP (CHO), and 2% DMSO.

The compounds of the present invention, including the compounds of Examples 1 to 86, exhibit a PRCP inhibition constant $IC_{50}$ of less than 10 µM. Preferred compounds of the present invention were found to exhibit a PRCP inhibition constant $IC_{50}$ of less than 1 µM. More preferred compounds of the present invention were found to exhibit a PRCP inhibition constant $IC_{50}$ of less than 100 nM.

| Human PRCP Enzyme Inhibition for Selected Compounds | |
| --- | --- |
| Example Number | Human PrCP $IC_{50}$ (nM) |
| 1 | 0.66 |
| 2 | 1.3 |
| 3 | 5.2 |
| 8 | 0.49 |
| 9 | 89 |
| 14 | 9.5 |
| 21 | 65 |
| 69 | 235 |
| 82 | 1.6 |
| 86 | 7.8 |

Examples of Pharmaceutical Compositions

As a specific embodiment of an oral composition of a composition of the present invention, 5 mg of Example 1 is formulated with sufficient finely divided lactose to provide a total amount of 580 to 590 mg to fill a size O hard gelatin capsule.

As another specific embodiment of an oral composition of a compound of the present invention, 2.5 mg of Example 1 is formulated with sufficient finely divided lactose to provide a total amount of 580 to 590 mg to fill a size 0 hard gelatin capsule.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the subject or mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the practices of the present invention. It is intended, therefore, that the invention be limited only by the scope of the claims which follow and that such claims be interpreted as broadly as is reasonable.

What is claimed is:

1. A compound of structural formula I:

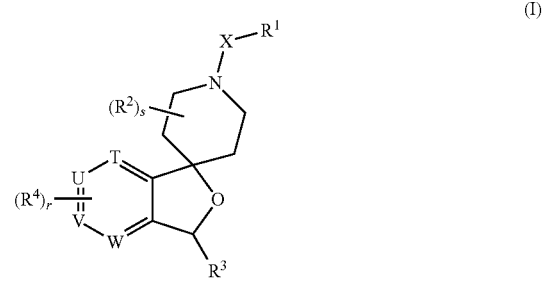

or a pharmaceutically acceptable salt thereof; wherein

T, U, V and W are C or CH;

each X is independently selected from the group consisting of:

(1) —$CH_2$—, (2) —$CH_2CH_2$—, (3) —$SO_2$—, (4) —C(O)—, and (5) —C(O)$CH_2$—, wherein each $CH_2$ is unsubstituted or substituted with one or two substituents selected from $R^a$;

each $R^1$ is independently selected from the group consisting of: pyrrolidine, azabicyclo[2.2.1]heptane, pyridine, pyrazine, pyridazine, pyrimidine, thiophene, benzodioxole, naphthalene, benzofuran, oxazole, thiazole, triazole, benzisoxazole, and imidazopyrimidine, wherein each, cycloheteroalkyl, aryl and heteroaryl is unsubstituted or substituted with one to three groups independently selected from $R^b$:

each $R^2$ is independently selected from the group consisting of:
(1) hydrogen,
(2) —$C_{1-6}$ alkyl,
(3) —$C_{1-6}$ alkoxy,
(4) halogen,
(5) oxo, and
(6) —OH;
each $R^3$ is independently selected from the group consisting of:
(1) —$(CH_2)_m$—$C_{3-7}$cycloalkyl,
(2) —$(CH_2)_m$—$C_{3-7}$cycloalkenyl,
(3) —$(CH_2)_m$—$C_{2-6}$cycloheteroalkyl,
(4) —$(CH_2)_m$—$C_{3-7}$cycloheteroalkenyl,
(5) —$(CH_2)_m$-aryl, and
(6) —$(CH_2)_m$-heteroaryl,
wherein each $CH_2$, cycloalkyl, cycloalkenyl, cycloheteroalkyl, cycloheteroalkenyl, aryl and heteroaryl is unsubstituted or substituted with one, two or three groups independently selected from $R^c$;
each $R^4$ is independently selected from the group consisting of:
(1) hydrogen,
(2) halogen,
(3) —CN,
(4) —$CF_3$,
(5) —$OCF_3$,
(6) —OH,
(7) —$OC_{1-6}$ alkyl, and
(8) —$C_{1-6}$ alkyl,
wherein alkyl is unsubstituted or substituted with one to three substituents selected from the group consisting of: —OH, halogen, —$C_{1-6}$ alkyl, —CN, —$OC_{1-6}$ alkyl, —$CO_2H$, and —$CO_2C_{1-6}$ alkyl;
each $R^a$ is independently selected from the group consisting of:
(1) —$C_{1-6}$ alkyl,
(2) —$(CH_2)_n CO_2H$,
(3) —$(CH_2)_n CO_2 C_{1-6}$ alkyl,
(4) —$(CH_2)_n$—OH,
(5) oxo,
(6) —$(CH_2)_n$—O—$C_{1-6}$ alkyl,
(7) —$(CH_2)_n$—$N(R^d)_2$, and
(8) —$(CH_2)_n$—S—$C_{1-6}$ alkyl,
wherein each $CH_2$, and alkyl is unsubstituted or substituted with one or two groups independently selected from: —OH, —$C_{1-6}$ alkyl, halogen, —CN, —$OC_{1-6}$ alkyl, —$CO_2H$, and —$CO_2C_{1-6}$ alkyl;
each $R^b$ is independently selected from the group consisting of:
(1) hydrogen,
(2) halogen,
(3) —$CF_3$,
(4) —$OCF_3$,
(5) —$OC_{1-6}$ alkyl, and
(6) —$C_{1-6}$ alkyl,
wherein each alkyl is unsubstituted or substituted with one to three substituents selected from the group consisting of: —OH, —$C_{1-6}$ alkyl, halogen, —CN, and —$CO_2C_{1-6}$ alkyl;
each $R^c$ is independently selected from the group consisting of:
(1) hydrogen,
(2) halogen,
(3) —$C_{1-6}$ alkyl,
(4) —CN,
(5) oxo,
(6) —OH,
(7) —$OC_{1-6}$ alkyl,
(8) —$CF_3$, and
(9) —$OCF_3$,
wherein alkyl is unsubstituted or substituted with one to three substituents selected from the group consisting of: —OH, —$C_{1-6}$ alkyl, halogen, —CN, —$OC_{1-6}$ alkyl, —$CO_2H$, and —$CO_2C_{1-6}$ alkyl;
each $R^d$ is independently selected from the group consisting of:
(1) hydrogen, and
(2) —$C_{1-6}$ alkyl;
m is selected from 0, 1, 2, 3 and 4;
n is selected from 0, 1, 2, 3 and 4;
q is selected from 0, 1, 2, 3 and 4;
r is selected from 0, 1, 2, and 3; and
s is selected from 0, 1, 2 and 3.

2. The compound of claim 1 wherein each $R^3$ is independently selected from the group consisting of:
(1) -aryl, and
(2) -heteroaryl,
wherein each aryl and heteroaryl is unsubstituted or substituted with one to three groups independently selected from $R^c$; or a pharmaceutically acceptable salt thereof.

3. The compound of claim 2 wherein each $R^3$ is independently selected from the group consisting of:
(1) -phenyl, and
(2) -pyridine,
wherein each phenyl and pyridine is unsubstituted or substituted with one to three groups independently selected from $R^c$; or a pharmaceutically acceptable salt thereof.

4. The compound of claim 1 wherein each X is independently selected from the group consisting of:
(1) —$CH_2$—,
(2) —$CH_2CH_2$—, and
(3) —$SO_2$—,
wherein each $CH_2$ is unsubstituted or substituted with one or two substituents selected from $R^a$; or a pharmaceutically acceptable salt thereof.

5. The compound of claim 4 wherein each X is independently selected from the group consisting of:
(1) —$CH_2$—, and
(2) —$SO_2$—,
wherein $CH_2$ is unsubstituted or substituted with one or two substituents selected from $R^a$; or a pharmaceutically acceptable salt thereof.

6. The compound of claim 1 wherein each $R^4$ is independently selected from the group consisting of:
(1) hydrogen,
(2) halogen, and
(3) —$C_{1-6}$ alkyl,
wherein alkyl is unsubstituted or substituted with one to three substituents selected from the group consisting of: —OH, halogen, —$C_{1-6}$alkyl, —CN, —$OC_{1-6}$ alkyl, —$CO_2H$, and —$CO_2C_{1-6}$ alkyl; or a pharmaceutically acceptable salt thereof.

7. The compound of claim 6 wherein $R^4$ is hydrogen; or a pharmaceutically acceptable salt thereof.

8. The compound of claim 1 wherein each $R^2$ is independently selected from the group consisting of:
(1) hydrogen,
(2) —$_{1-6}$ alkyl,
(3) oxo, and
(4) —OH;
or a pharmaceutically acceptable salt thereof.

9. The compound of claim 8 wherein $R^2$ is hydrogen; or a pharmaceutically acceptable salt thereof.

10. The compound of claim 1

R¹ is pyridine, wherein pyridine is unsubstituted or substituted with one to three groups independently selected from R$^b$;

or a pharmaceutically acceptable salt thereof.

11. The compound of claim 1 wherein each X is independently selected from the group consisting of:
  (1) —CH$_2$—,
  (2) —CH$_2$CH$_2$—, and
  (3) —SO$_2$—,
wherein each CH$_2$ is unsubstituted or substituted with one or two substituents selected from R$^a$;

each R² is independently selected from the group consisting of:
  (1) hydrogen,
  (2) —C$_{1-6}$ alkyl,
  (3) oxo, and
  (4) —OH;

each R³ is independently selected from the group consisting of:
  (1) -aryl, and
  (2) -heteroaryl,
wherein each aryl and heteroaryl is unsubstituted or substituted with one to three groups independently selected from R$^c$;

each R⁴ is independently selected from the group consisting of:
  (1) hydrogen,
  (2) halogen, and
  (3) —C$_{1-6}$ alkyl,
wherein alkyl is unsubstituted or substituted with one to three substituents selected from the group consisting of: —OH, halogen, —C$_{1-6}$alkyl, —CN, —OC$_{1-6}$ alkyl, —CO$_2$H, and —CO$_2$C$_{1-6}$ alkyl;

or a pharmaceutically acceptable salt thereof.

12. The compound of claim 1 wherein:

each X is independently selected from the group consisting of:
  (1) —CH$_2$—, and
  (2) —SO$_2$—,
wherein CH$_2$ is unsubstituted or substituted with one or two substituents selected from R$^a$;

R¹ is pyridine, wherein pyridine is unsubstituted or substituted with one to three groups independently selected from R$^b$;

R² is hydrogen;

each R³ is independently selected from the group consisting of:
  (1) -phenyl, and
  (2) -pyridine,
wherein each phenyl and pyridine is unsubstituted or substituted with one to three groups independently selected from R$^c$;

R⁴ is hydrogen;

or a pharmaceutically acceptable salt thereof.

13. A compound selected from the group consisting of:

113
-continued
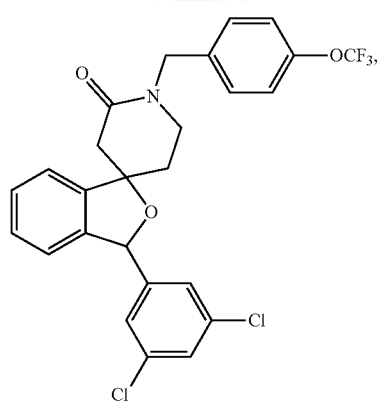
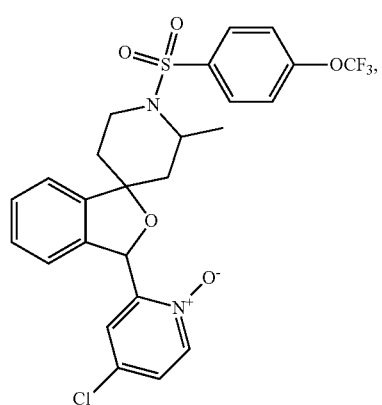
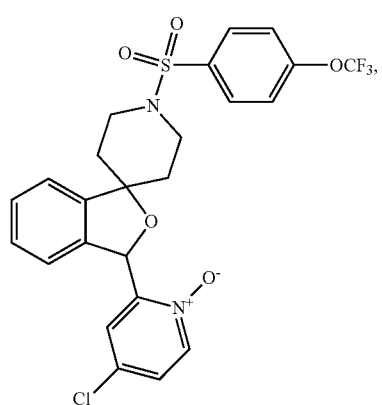
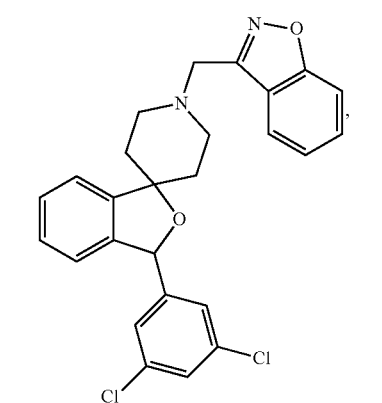
114
-continued
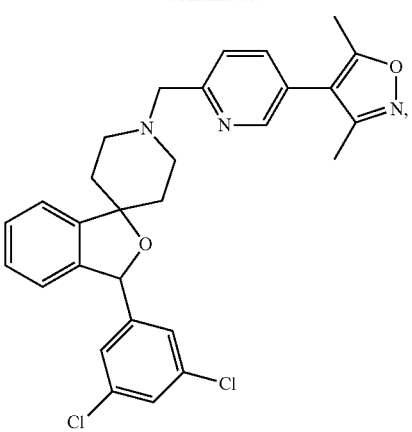
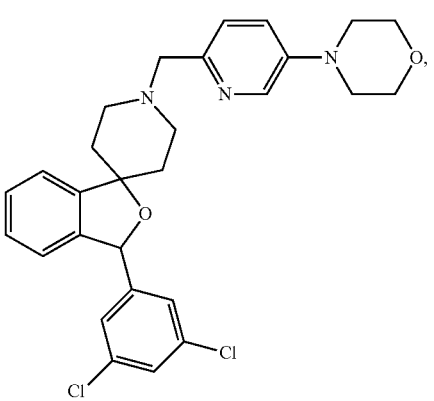
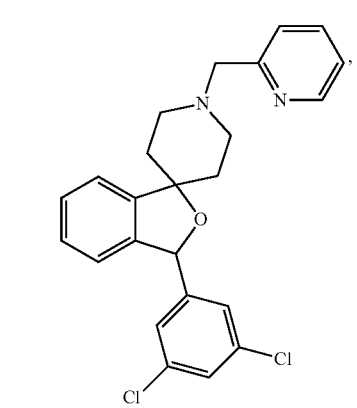
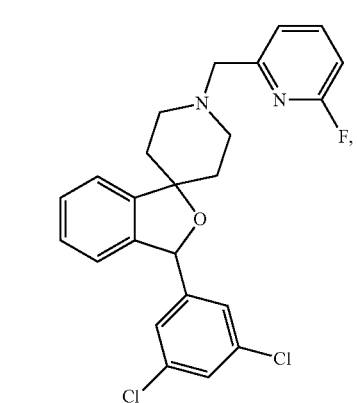

115 -continued
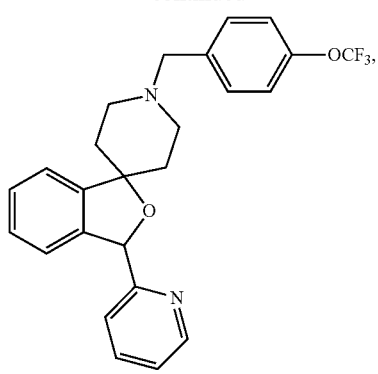
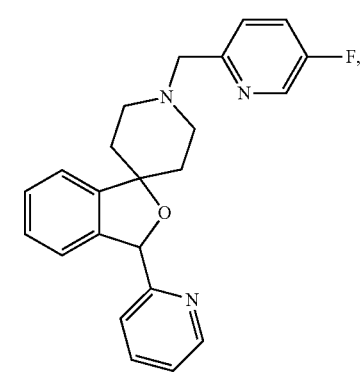
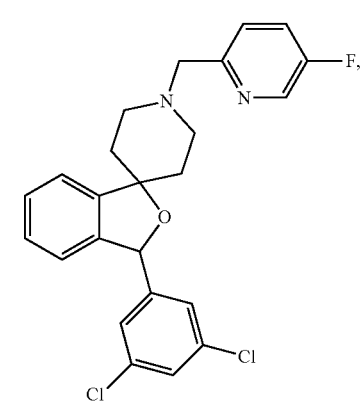
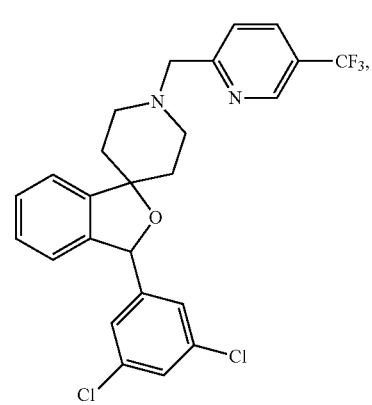
116 -continued
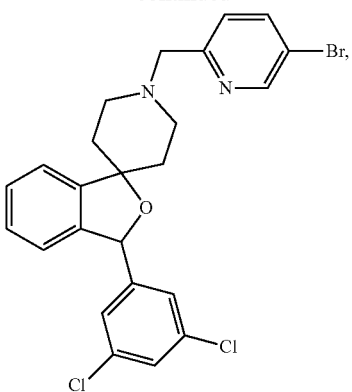
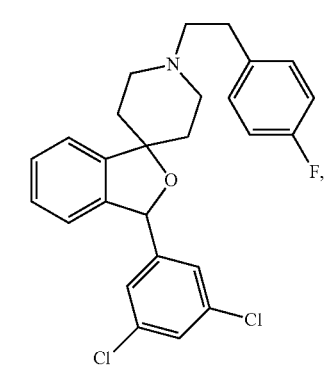
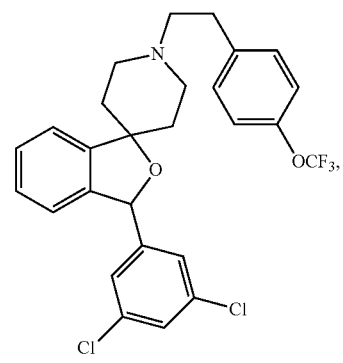
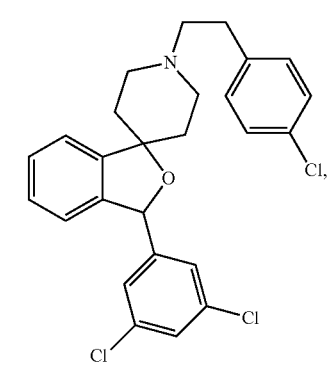

117
-continued
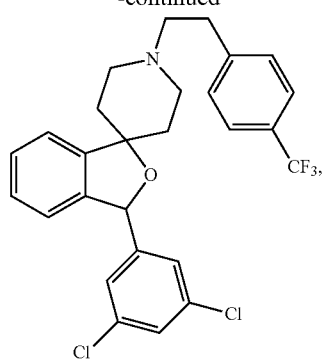
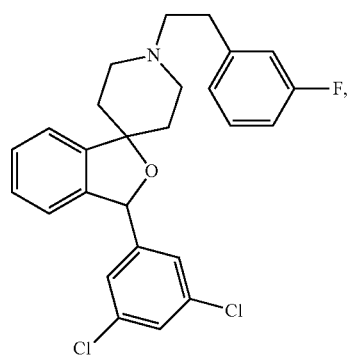
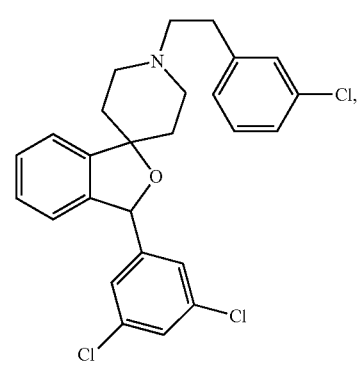
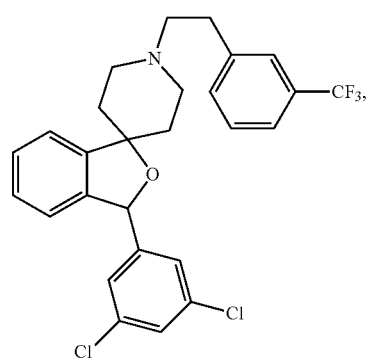
118
-continued
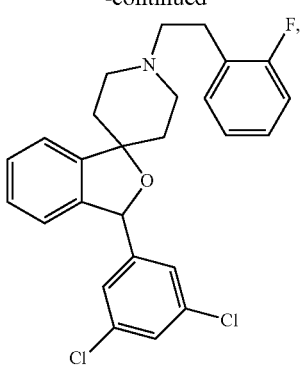
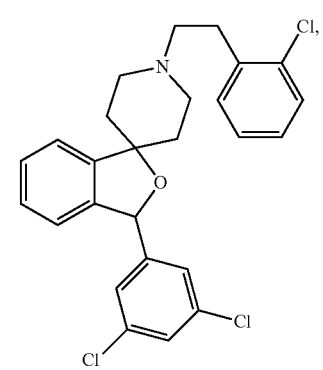
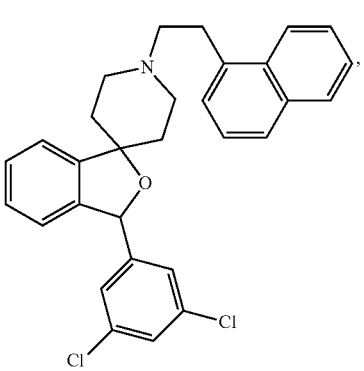
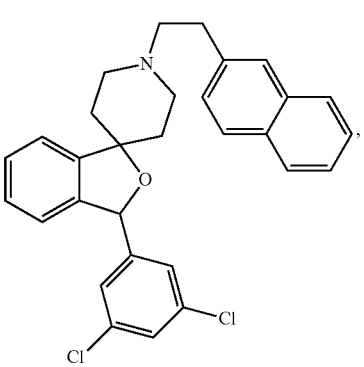

-continued
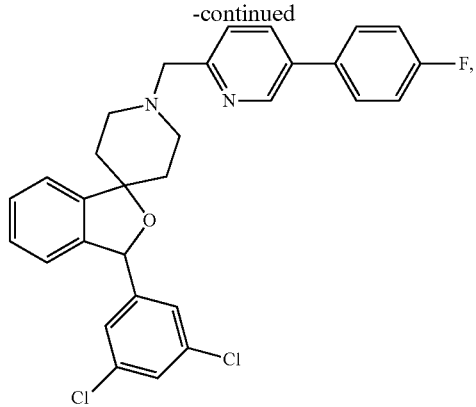
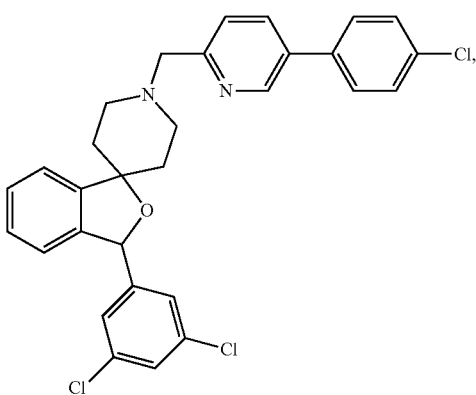
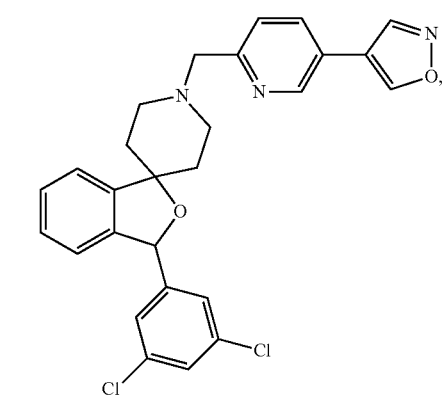
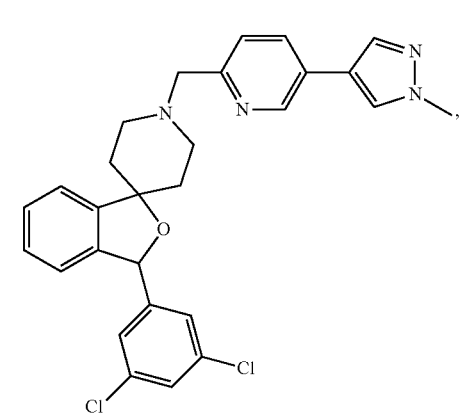
-continued
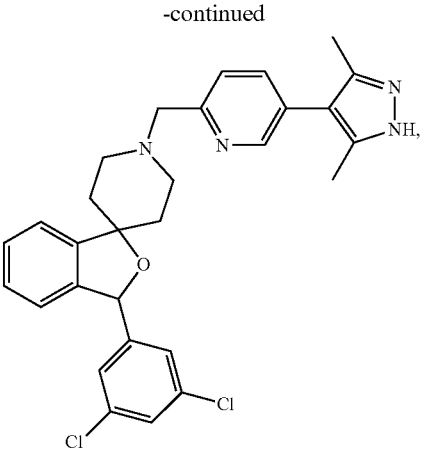
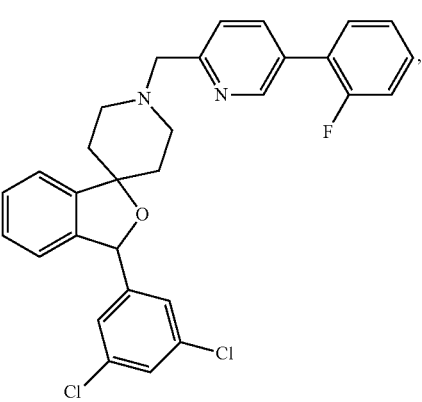
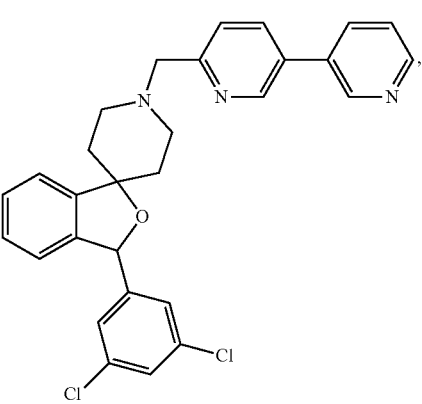
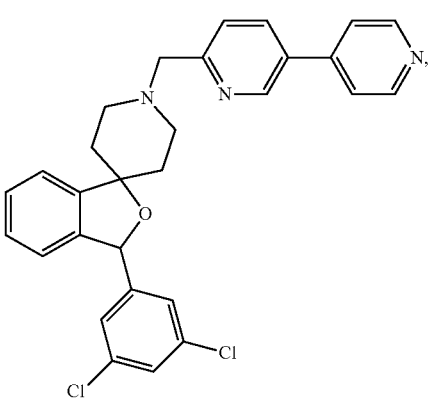

121
-continued
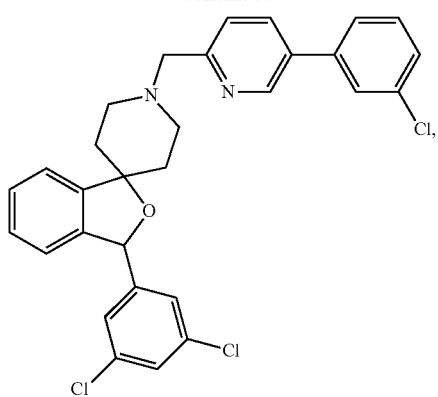
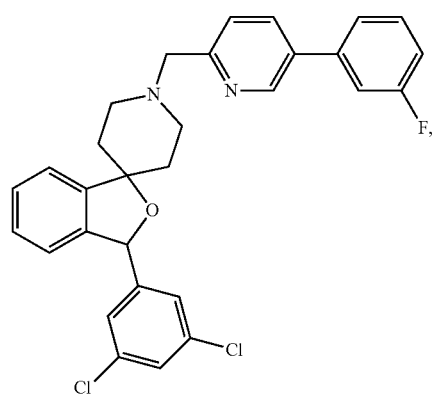
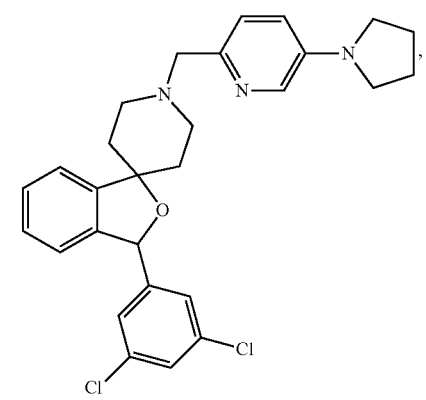
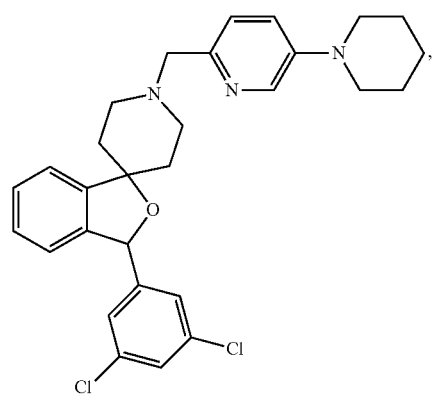
122
-continued
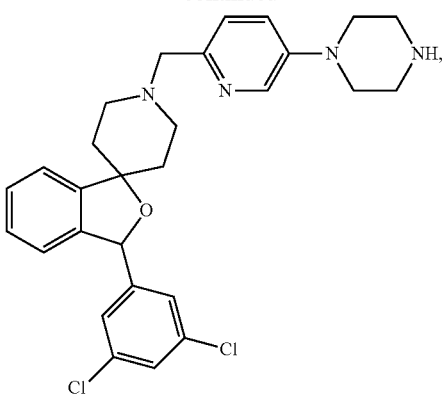
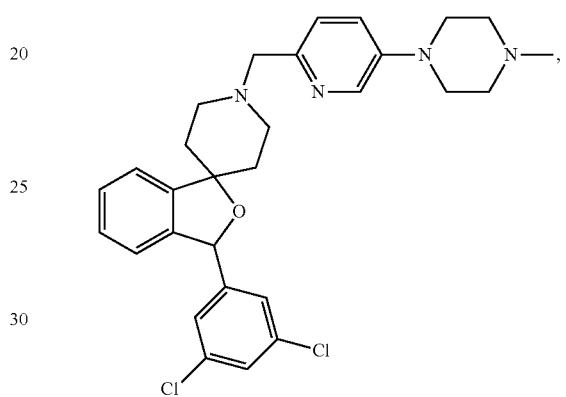
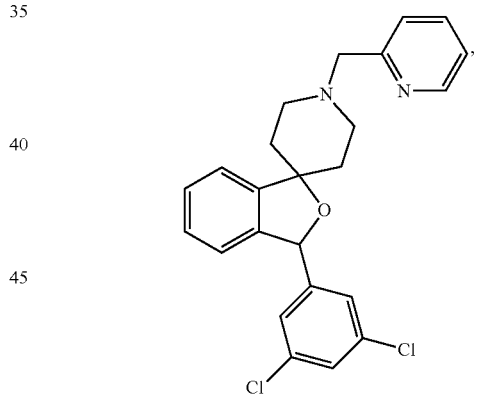
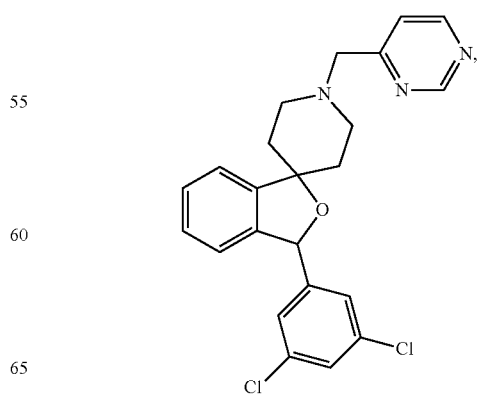

123
-continued
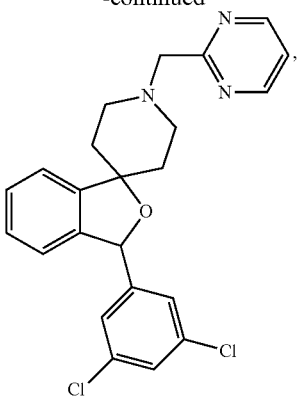
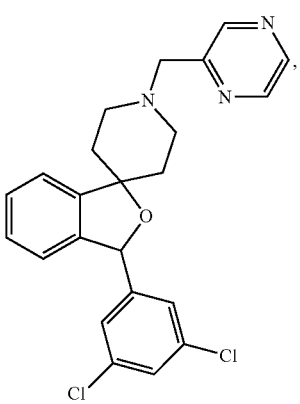
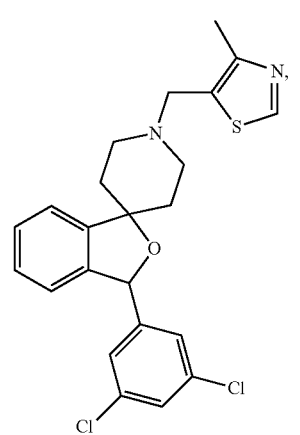
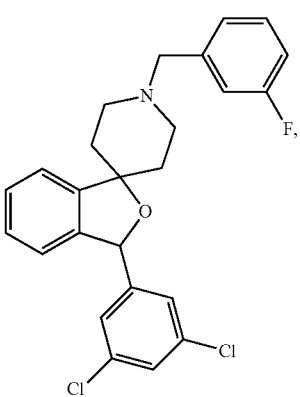
124
-continued
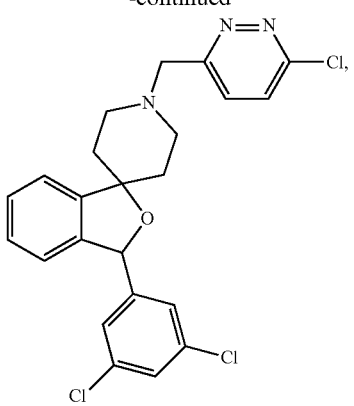
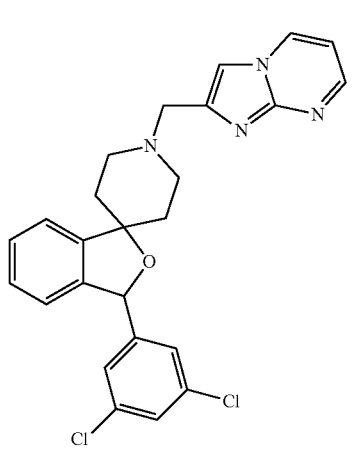
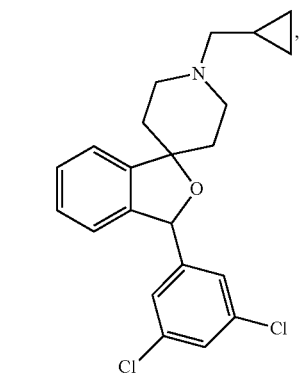
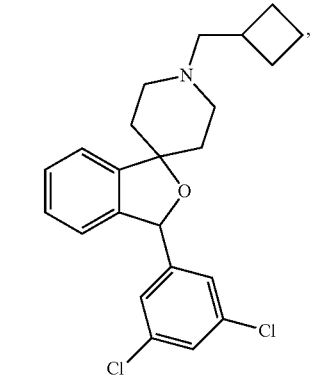

-continued

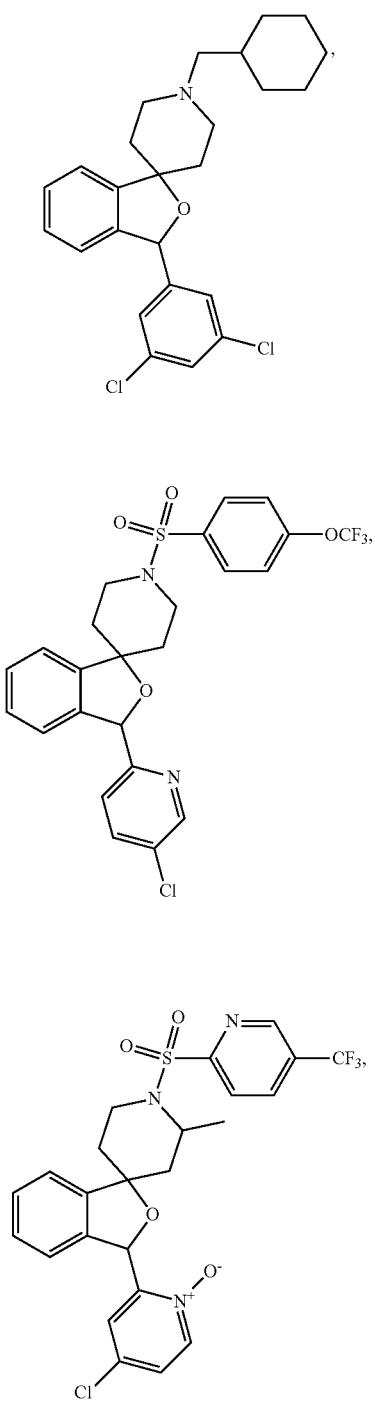

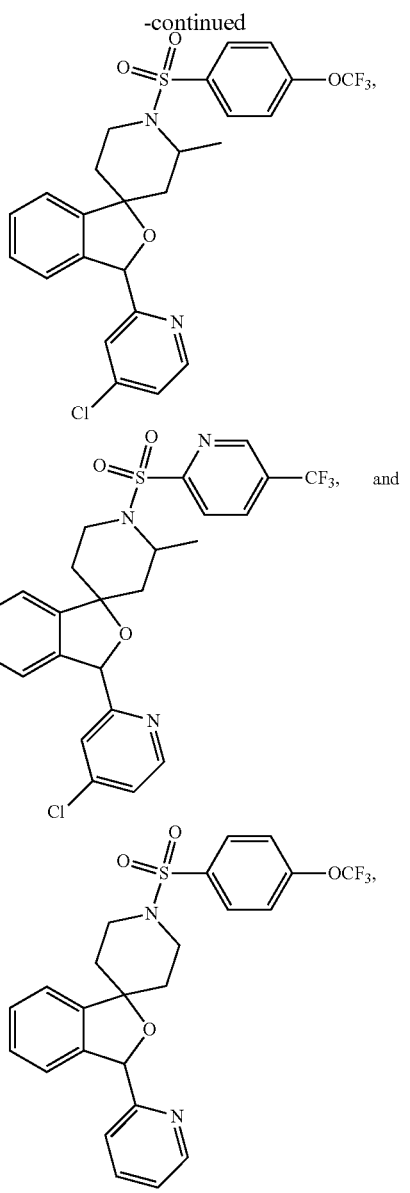

or a pharmaceutically acceptable salt thereof.

14. A pharmaceutical composition comprising a compound of claim 1 in combination with a pharmaceutically acceptable carrier.

15. A composition comprising a compound according to claim 1 and a compound selected from simvastatin, ezetimibe, taranabant and sitagliptin; and a pharmaceutically acceptable carrier.

* * * * *